(12) United States Patent
Burris et al.

(10) Patent No.: US 11,795,162 B2
(45) Date of Patent: Oct. 24, 2023

(54) MODULATORS OF THE ESTROGEN-RELATED RECEPTOR

(71) Applicant: Saint Louis University, St. Louis, MO (US)

(72) Inventors: Thomas Burris, Columbia, IL (US); John K. Walker, St. Louis, MO (US); Carissa S. Hampton, Litchfield, IL (US); Keith McCormick Haynes, St. Louis, MO (US); Kristine Griffett, St. Louis, MO (US); Cyrielle Billon, St. Louis, MO (US); Sadichha Sitaula, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 25 days.

(21) Appl. No.: 16/639,807

(22) PCT Filed: Aug. 17, 2018

(86) PCT No.: PCT/US2018/046840
§ 371 (c)(1),
(2) Date: Feb. 18, 2020

(87) PCT Pub. No.: WO2019/036562
PCT Pub. Date: Feb. 21, 2019

(65) Prior Publication Data
US 2020/0247792 A1    Aug. 6, 2020

Related U.S. Application Data

(60) Provisional application No. 62/547,555, filed on Aug. 18, 2017.

(51) Int. Cl.
| | | |
|---|---|---|
| *C07D 209/42* | (2006.01) | |
| *C07D 413/04* | (2006.01) | |
| *C07D 231/14* | (2006.01) | |
| *C07D 277/56* | (2006.01) | |
| *C07D 277/82* | (2006.01) | |
| *C07D 307/68* | (2006.01) | |
| *C07D 333/38* | (2006.01) | |
| *C07D 401/04* | (2006.01) | |
| *C07D 409/04* | (2006.01) | |
| *C07D 409/12* | (2006.01) | |
| *C07D 417/04* | (2006.01) | |
| *C07F 5/02* | (2006.01) | |

(52) U.S. Cl.
CPC ......... *C07D 413/04* (2013.01); *C07D 209/42* (2013.01); *C07D 231/14* (2013.01); *C07D 277/56* (2013.01); *C07D 277/82* (2013.01); *C07D 307/68* (2013.01); *C07D 333/38* (2013.01); *C07D 401/04* (2013.01); *C07D 409/04* (2013.01); *C07D 409/12* (2013.01); *C07D 417/04* (2013.01); *C07F 5/027* (2013.01)

(58) Field of Classification Search
CPC .. C07D 209/42; C07D 231/14; C07D 277/56; C07D 277/82; C07D 307/68; C07D 333/38; C07D 401/04; C07D 409/04; C07D 409/12; C07D 413/04; C07D 417/04; C07D 417/12
See application file for complete search history.

(56) References Cited

FOREIGN PATENT DOCUMENTS

| FR | 2273543 | * | 1/1976 | ........... A61K 31/495 |
|---|---|---|---|---|
| JP | 50041865 | * | 4/1975 | ........... C07D 271/06 |
| WO | WO 98/01428 | * | 6/1997 | ........... C07D 236/06 |
| WO | WO2004056774 | * | 7/2004 | ........... C07D 213/00 |

OTHER PUBLICATIONS

Jansen, et. al., Journal of the Chemical Society (1961) 405-11. (Year: 1961).*
Russo, et. al., Annali di Chimica (Rome, Italy) (1966), 56(1-2), 87-95. (Year: 1966).*
Veronese, et. al., Journal of Heterocyclic Chemistry (1980), 17(8), 1723-5. (Year: 1980).*
Karady, et. al., Heterocycles (1986), 24(5), 1193-6. (Year: 1986).*
Ong, et. al., Inorganica Chimica Acta (1986), 125(4), 203-6. (Year: 1986).*
Burris, "Estrogen-related receptor (ERR) agonists for treatment of metabolic disorders," Presentation, 2017.
Busch, B. B. et al. Identification of a selective inverse agonist for the orphan nuclear receptor estrogen-related receptor alpha. *Journal of Medicinal Chemistry* 47, 5593-5596, doi: 10.1021/jm049334f (2004).
Chen, F. et al. Identification of two hERR2-related novel nuclear receptors utilizing bioinformatics and inverse PCR. *Gene* 228, 101-109 (1999).
Coward, P., Lee, D., Hull, M. V. & Lehmann, J. M. 4-Hydroxytamoxifen binds to and deactivates the estrogen-related receptor gamma. *Proceedings of the National Academy of Sciences of the United States of America* 98, 8880-8884 (2001).
Evans, R. M. The steroid and thyroid hormone receptor superfamily. *Science* 240, 889-895 (1988).
Giguere, V., Yang, N., Segui, P. & Evans, R. M. Identification of a new class of steroid hormone receptors. *Nature* 331, 91-94, doi:10.1038/331091a0 (1988).
Giguere, V. Orphan nuclear receptors: From gene to function. *Endocrine Reviews* 20, 689-725 (1999).
Giguere, V. Transcriptional control of energy homeostasis by the estrogen-related receptors. *Endocrine Reviews* 29, 677-696, doi:10.1210/er.2008-0017 (2008).
Hampton et al., "Efforts towards the development of new ERRg modulators via structure-based drug design," Poster, American Chemical Society Meeting, Washington, DC, 2017.

(Continued)

*Primary Examiner* — Jeffrey H Murray
(74) *Attorney, Agent, or Firm* — Parker Highlander LLC

(57) ABSTRACT

In one aspect, the present disclosure describes new estrogen receptor-related orphan receptor (EER) inverse agonist compounds. Also described are pharmaceutical formulations, methods of synthesis and uses thereof.

18 Claims, 1 Drawing Sheet

(56) References Cited

OTHER PUBLICATIONS

Hyatt et al., "On the intractability of estrogen-related receptor alpha as a target for activation by small molecules," *J Med Chem.*, 50(26):6722-6724, 2007.

Kim et al., "Identification of Selective ERR Inverse Agonists," *Molecules*, 21:80, pp. 1-16, 2016.

Kliewer, S. A., Lehmann, J. M. & Willson, T. M. Orphan nuclear receptors: Shifting endocrinology into reverse. *Science* 284, 757-760 (1999).

Mangelsdorf, D. J. et al. The Nuclear Receptor Superfamily—the 2nd Decade. *Cell* 83, 835-839 (1995).

Mangelsdorf, D. J. & Evans, R. M. The Rxr Heterodimers and Orphan Receptors. *Cell* 83, 841-850 (1995).

Matsakas, A., Yadav, V., Lorca, S. & Narkar, V. Muscle ERRgamma mitigates Duchenne muscular dystrophy via metabolic and angiogenic reprogramming. *Faseb J* 27, 4004-4016, doi: 10.1096/fj.13-228296 (2013).

Narkar, V. A. et al. Exercise and PGC-1alpha-independent synchronization of type I muscle metabolism and vasculature by ERRgamma. *Cell Metabolism* 13, 283-293, doi:10.1016/j.cmet.2011.01.019(2011).

Omalley, B. W. & Conneely, O. M. Orphan Receptors—In Search of a Unifying Hypothesis for Activation. *Molecular Endocrinology* 6, 1359-1361 (1992).

PCT International Preliminary Report on Patentability issued in International Application No. PCT/US2018/046840, dated Feb. 27, 2020.

PCT International Search Report and Written Opinion issued in International Application No. PCT/US2018/046840, dated Nov. 5, 2018.

PUBCHEM-CID: 1497069, pp. 1-12, Jul. 11, 2005.

PUBCHEM-CID: 3746437, pp. 1-15, Sep. 10, 2005.

Rangwala, S. M. et al. Estrogen-related receptor gamma is a key regulator of muscle mitochondrial activity and oxidative capacity. *The Journal of biological chemistry* 285, 22619-22629, doi:10.1074/jbc.M110.125401 (2010).

Sladek, R., Bader, J. A. & Giguere, V. The orphan nuclear receptor estrogen-related receptor alpha is a transcriptional regulator of the human medium-chain acyl coenzyme A dehydrogenase gene. *Molecular and Cellular Biology* 17, 5400-5409 (1997).

Tremblay, G. B. et al. Diethylstilbestrol regulates trophoblast stem cell differentiation as a ligand of orphan nuclear receptor ERR beta. *Genes & development* 15, 833-838, doi:10.1101/gad.873401 (2001).

Tremblay, G. B., Bergeron, D. & Giguere, V. 4-Hydroxytamoxifen is an isoform-specific inhibitor of orphan estrogen-receptor-related (ERR) nuclear receptors beta and gamma. *Endocrinology* 142, 4572-4575 (2001).

Zuercher, W. J. et al. Identification and structure-activity relationship of phenolic acyl hydrazones as selective agonists for the estrogen-related orphan nuclear receptors ERRbeta and ERRgamma. *Journal of Medicinal Chemistry* 48, 3107-3109, doi:10.1021/jm050161j (2005).

Beal, M. F., "Mitochondria Take Center Stage in Aging and Neurodegeneration," *Annals of Neurology*, 58 (2005): 495-505.

Cho, D-H. et al., "Mitochondrial dynamics in cell death and neurodegeneration," *Cellular and Molecular Life Sciences*, 67 (2010): 3435-3447.

Johri, A. et al., "Mitochondrial Dysfunction in Neurodegenerative Diseases," *Perspectives in Pharmacology*, 342.3 (2012): 619-630.

Lin, M. T. et al., "Mitochondrial dysfunction and oxidative stress in neurodegenerative disease," *Nature*, 443 (2006): 787-795.

Rezin, G. T. et al., "Mitochondrial Dysfunction and Psychiatric Disorders," *Neurochem Res.*, 37 (2009): 1021-1029.

Yan, M. H. et al., "Mitochondrial defects and oxidative stress in Alzheimer disease and Parkinson disease," *Free Radical Biology and Medicine*, 62 (2013): 90-101.

\* cited by examiner

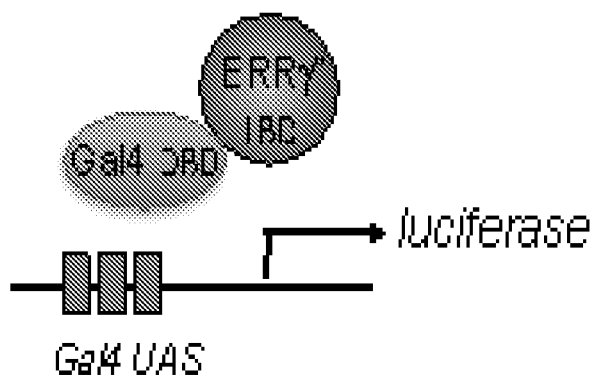

MODULATORS OF THE ESTROGEN-RELATED RECEPTOR

This application is a national phase application under 35 U.S.C. § 371 of International Application No. PCT/US2018/046840, filed Aug. 17, 2018, which claims benefit of priority to U.S. Provisional Application U.S. Ser. No. 62/547,555, filed Aug. 18, 2017, the entire contents of each of which are hereby incorporated by reference.

This invention was made with government support under HIH AR069280-01 awarded by the National institutes of Health. The government has certain rights in the invention.

BACKGROUND

1. Field

This disclosure relates to the fields of medicine, pharmacology, chemistry, and metabolism. In particular, new compounds, compositions, and methods of treatment, relating to estrogen receptor-related orphan receptor gamma are disclosed.

2. Related Art

The nuclear receptor (NR) superfamily constitutes a group of 48 transcription factors in humans, which includes the receptors for steroid hormones, thyroid hormone, lipophilic vitamins, and cholesterol metabolites (Manglesdorf et al., 1995; Evans, R. M., 1988). Approximately half of NRs are classified as orphan receptors since they do not have well characterized ligands (Kliewer et al., 1999; Giguere, V., 1999; Manglesdorf & Evans, 1995; Omalley & Conneely, 1992). Virtually all the NRs that have identified ligands are well-characterized targets for the development of drugs to treat myriad diseases including, diabetes, atherosclerosis, inflammation, and endocrine/reproductive disorders. NRs are proteins composed of multiple domains that provide a range of functions including DNA binding, small molecule ligand binding, and transcriptional regulatory activity (Manglesdorf et al., 1995; Evans, R. M., 1988). NRs function as transcription factors and typically regulate target gene transcription in a ligand-dependent manner. NRs recognize specific DNA response elements in the promoters/enhancers of their cognate target genes where they can respond to ligands by altering their ability to recruit a range of other transcriptional proteins that alter the rate of gene expression. Much about what is known about the mechanism of the ligand-dependent transcriptional regulation by NRs has been revealed by structure-function studies of the carboxy-terminal ligand binding domain (LBD). The LBD is a globular domain composed almost exclusively of α-helices arranged in a three layered "sandwich". NR ligands bind to a ligand binding pocket (LBP) within the interior of this globular domain consistent with the typical hydrophobic character of NR ligands. Agonist binding results in a conformational change that results in formation of a hydrophobic cleft on the surface of the LBD that allows for docking of transcriptional coactivator proteins such as the steroid receptor coactivators (SRCs). Antagonists bind within the LBP, but block the binding of agonist and the resulting conformational change. Certain receptors have constitutive transcriptional activity since the LBD is in an "active" conformation even without an agonist present.

The estrogen receptor-related orphan receptors (ERRs) were the first orphan NRs to be identified. As their name indicates they are quite similar to the estrogen receptors (ERα and ERβ), but do not bind to endogenous ER ligands. Where the ERs function as obligate homodimers, the ERRs (ERRα, ERRβ, and ERRγ) function as monomers and bind to a DNA response element that are quite distinct from that of the ERs (Giguere, V., 2008). ERRα is widely expressed as is ERRγ, but greatest expression is noted in tissues with high energy demand such as the skeletal muscle, heart, adipose tissue, liver, and kidney (Giguere et al., 1988; Chen et al., 1999; Sladek et al., 1997). ERRβ is considerably more restricted in its pattern of expression where low levels of expression are noted in the liver, stomach, skeletal muscle, heart and kidney (Giguere et al., 1988; Chen et al., 1999). Unlike the ERs that require ligand binding to display transcriptional activity, all three ERRs display constitutive transcriptional activity in the absence of any ligand (Giguere, V., 2008).

Muscular dystrophies (MDs) are a group of muscle diseases that cause progressive muscle weakness. MDs are genetic disorders and a number of forms of MD (~30) have been characterized that are caused by mutations in distinct genes. Duchenne muscular dystrophy (DMD) is the most common childhood form of MD, is X-linked, and has an incidence rate of 1 case per 3,600-6,000 newborn males. Individuals with DMD typically die before the age of 25 and there are no effective treatments that directly target the aberrant muscle function. DMD is caused by mutations in the dystrophin gene, which is one of the largest human genes. The dystrophin protein is a cytoplasmic protein and plays a critical role as part of a protein complex (dystrophin-associated protein complex (DAG)) that connects the cytoskeleton of the muscle fiber to the extracellular matrix through the sarcolemma, and mutations severely disrupt dystrophin function lead to DMD.

ERRγ has been suggested to be a putative target for therapeutics to treat DMD. ERRγ target genes that include both metabolic and angiogenic genes are substantially down-regulated in the mdx mouse (DMD mouse model) relative to normal wt mice (Matsakas et al., 2013). Consistent with these alterations in gene expression muscle vasculature, oxidative myofibers and exercise tolerance were decreased in the mdx mice relative to wt mice (Matsakas et al., 2013). Muscle specific overexpression of ERRγ in the mdx mice restored normal function and prevented the development of deficits typical of muscular dystrophy including muscle damage, reduced oxidative capacity, and hypoxia (Matsakas et al., 2013). These data suggest that enhancing ERRγ activity with a synthetic agonist may provide therapeutic utility in the treatment of DMD.

The role of ERRγ in skeletal muscle has significant implications for treatment of metabolic diseases as illustrated by gain and loss of function experiments. Muscle specific overexpression of ERRγ led to phenotypic alterations typically associated with exercise (metabolic and vascular transformation) without exercise training (Narkar et al., 2011). Increased ERRγ activity induced expression of genes associated with fatty acid oxidation and mitochondrial respiration and type I fiber specification (Narkar et al., 2011). These alterations led to increased running endurance in the mice (Narkar et al., 2011). Rangwala et al. reported similar results with overexpression of ERRγ in muscle and additionally, this group also demonstrated that loss of one copy of ERRγ resulted in decreased exercise capacity and mitochondrial function (Rangwala et al., 2010). Furthermore, a synthetic ERRβ/γ agonist increased mitochondrial function in cultured mouse myotubes (Rangwala et al., 2010). Unfortunately, there were no specific ERRγ agonists, or ERRβ/γ agonists for that matter, with in vivo activity to test if these effects could be recapitulated in mice. Clearly, increased skeletal muscle oxidative capacity is associated with improved insulin sensitivity as well as a reduction in obesity. Thus synthetic ERRγ agonists may hold significant utility in the treatment of type 2 diabetes and obesity.

SUMMARY

In accordance with the disclosure, there is provided a compound of the formula:

$$X_1\text{—}Y_1\text{-L-A-}R_1 \tag{I}$$

wherein:
X$_1$ is aryl$_{(C\leq12)}$, heteroaryl$_{(C\leq12)}$, or a substituted version of either of these groups; or -arenediyl$_{(C\leq12)}$-R$_2$, -heteroarenediyl$_{(C\leq12)}$-R$_2$, or a substituted version thereof, wherein:
  R$_2$ is —B(OR')(OR''), —NR$_3$R$_4$, —C(O)OR$_5$, —C(O)NR$_6$R$_7$; wherein:
    R$_3$, R$_4$, R$_6$, and R$_7$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or R$_3$ and R$_4$ or R$_6$ and R$_7$ are taken together and are a divalent amino protecting group;
    R' and R'' are hydrogen, alkyl$_{(C\leq12)}$, cycloalkyl$_{(C\leq12)}$, aryl$_{(C\leq12)}$, aralkyl$_{(C\leq12)}$, or a substituted version of any of these groups; and
    R$_5$ is alkyl$_{(C\leq12)}$, cycloalkyl$_{(C\leq12)}$, aryl$_{(C\leq12)}$, aralkyl$_{(C\leq12)}$, or a substituted version of any of these groups; or
  R$_2$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;
Y$_1$ is heteroarenediyl$_{(C\leq12)}$, substituted heteroarenediyl$_{(C\leq12)}$, heterocycloalkanediyl$_{(C\leq12)}$, or substituted heterocycloalkanediyl$_{(C\leq12)}$;
L is a covalent bond, —C(O)—, —S(O)$_2$—, —NR$_c$—, alkanediyl$_{(C\leq6)}$, or substituted alkanediyl$_{(C\leq6)}$; wherein:
  R$_c$ is hydrogen, alkyl$_{(C\leq8)}$, substituted alkyl$_{(C\leq8)}$, cycloalkyl$_{(C\leq8)}$, substituted cycloalkyl$_{(C\leq8)}$, alkylsulfonyl$_{(C\leq8)}$, substituted alkylsulfonyl$_{(C\leq8)}$;
A is —O—, —S—, —C(O)—, or —S(O)$_2$—, wherein:
  R$_8$ is hydrogen, alkyl$_{(C\leq8)}$, substituted alkyl$_{(C\leq8)}$, cycloalkyl$_{(C\leq8)}$, substituted cycloalkyl$_{(C\leq8)}$, alkylsulfonyl$_{(C\leq8)}$, substituted alkylsulfonyl$_{(C\leq8)}$; or
  R$_8$ and R$_1$ are taken together and are heterocycloalkanediyl$_{(C\leq12)}$, heteroarenediyl$_{(C\leq12)}$, or a substituted version thereof;
  R$_1$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, -alkanediyl$_{(C\leq6)}$-heterocycloalkyl$_{(C\leq12)}$, or a substituted version of any of these groups; or aryl$_{(C\leq12)}$ or substituted aryl$_{(C\leq12)}$, wherein two hydrogen atoms have been replaced with —NR$_a$C(O)NR$_b$—; or R$_1$ is taken together with R$_8$ as described above; wherein:
    R$_a$ and R$_b$ are each independently hydrogen, alkyl$_{(C\leq6)}$, substituted alkyl$_{(C\leq6)}$, cycloalkyl$_{(C\leq6)}$, or substituted cycloalkyl$_{(C\leq6)}$; or R$_1$ is -arenediyl$_{(C\leq12)}$-R$_9$, -heteroarenediyl$_{(C\leq12)}$-R$_9$, or a substituted version thereof, wherein:
  R$_9$ is —B(OR''')(OR''''), —NR$_{10}$R$_{11}$, —C(O)OR$_{12}$, —C(O)NR$_{13}$R$_{14}$; wherein:
    R$_{10}$, R$_{11}$, R$_{13}$, and R$_{14}$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or R$_{10}$ and R$_{11}$ or R$_{13}$ and R$_{14}$ are taken together and are a divalent amino protecting group;
    R''' and R'''' are hydrogen, alkyl$_{(C\leq12)}$, cycloalkyl$_{(C\leq12)}$, aryl$_{(C\leq12)}$, aralkyl$_{(C\leq12)}$, or a substituted version of any of these groups; and
    R$_{12}$ is alkyl$_{(C\leq12)}$, cycloalkyl$_{(C\leq12)}$, aryl$_{(C\leq12)}$, aralkyl$_{(C\leq12)}$, or a substituted version of any of these groups; or
  R$_9$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;
or a pharmaceutically acceptable salt thereof.

In accordance with the disclosure, there is provided a compound of the formula:

$$X_1\text{—}Y_1\text{-L-A-}R_1 \tag{I}$$

wherein:
X$_1$ is aryl$_{(C\leq12)}$, heteroaryl$_{(C\leq12)}$, or a substituted version of either of these groups; or -arenediyl$_{(C\leq12)}$-R$_2$, -heteroarenediyl$_{(C\leq12)}$-R$_2$, or a substituted version thereof, wherein:
  R$_2$ is —B(OR')(OR''), —NR$_3$R$_4$, —C(O)OR$_5$, —C(O)NR$_6$R$_7$, —C(O)R$_{15}$, —SO$_2$R$_{16}$; wherein:
    R$_3$, R$_4$, R$_6$, and R$_7$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or R$_3$ and R$_4$ or R$_6$ and R$_7$ are taken together and are a divalent amino protecting group;
    R' and R'' are hydrogen, alkyl$_{(C\leq12)}$, cycloalkyl$_{(C\leq12)}$, aryl$_{(C\leq12)}$, aralkyl$_{(C\leq12)}$, or a substituted version of any of these groups; and
    R$_5$, R$_{15}$, and R$_{16}$ are each independently alkyl$_{(C\leq12)}$, cycloalkyl$_{(C\leq12)}$, aryl$_{(C\leq12)}$, aralkyl$_{(C\leq12)}$, or a substituted version of any of these groups; or
  R$_2$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;
Y$_1$ is heteroarenediyl$_{(C\leq12)}$, substituted heteroarenediyl$_{(C\leq12)}$, heterocycloalkanediyl$_{(C\leq12)}$, or substituted heterocycloalkanediyl$_{(C\leq12)}$;
L is a covalent bond, —C(O)—, —S(O)$_2$—, —NR$_c$—, alkanediyl$_{(C\leq6)}$, or substituted alkanediyl$_{(C\leq6)}$; wherein:
  R$_c$ is hydrogen, alkyl$_{(C\leq8)}$, substituted alkyl$_{(C\leq8)}$, cycloalkyl$_{(C\leq8)}$, substituted cycloalkyl$_{(C\leq8)}$, alkylsulfonyl$_{(C\leq8)}$, substituted alkylsulfonyl$_{(C\leq8)}$;
A is —O—, —S—, —NR$_8$—, —C(O)—, or —S(O)$_2$—, wherein:
  R$_8$ is hydrogen, alkyl$_{(C\leq8)}$, substituted alkyl$_{(C\leq8)}$, cycloalkyl$_{(C\leq8)}$, substituted cycloalkyl$_{(C\leq8)}$, alkylsulfonyl$_{(C\leq8)}$, substituted alkylsulfonyl$_{(C\leq8)}$; or $R_8$ and $R_1$ are taken together and are heterocycloalkanediyl$_{(C \leq 12)}$, heteroarenediyl$_{(C \leq 12)}$, or a substituted version thereof;

$R_1$ is alkyl$_{(C \leq 12)}$, cycloalkyl$_{(C \leq 12)}$, aryl$_{(C \leq 18)}$, heteroaryl$_{(C \leq 18)}$, heterocycloalkyl$_{(C \leq 12)}$, aralkyl$_{(C \leq 18)}$, heteroaralkyl$_{(C \leq 18)}$, -alkanediyl$_{(C \leq 6)}$-heterocycloalkyl$_{(C \leq 12)}$, or a substituted version of any of these groups; or aryl$_{(C \leq 12)}$ or substituted aryl$_{(C \leq 12)}$, wherein two hydrogen atoms have been replaced with —NR$_a$C(O)NR$_b$—; or R$_1$ is taken together with R$_8$ as described above; wherein:

$R_a$ and $R_b$ are each independently hydrogen, alkyl$_{(C \leq 6)}$, substituted alkyl$_{(C \leq 6)}$, cycloalkyl$_{(C \leq 6)}$, or substituted cycloalkyl$_{(C \leq 6)}$; or $R_1$ is -arenediyl$_{(C \leq 12)}$-R$_9$, -heteroarenediyl$_{(C \leq 12)}$-R$_9$, or a substituted version thereof, wherein:

$R_9$ is —B(OR''')(OR''''), —NR$_{10}$R$_{11}$, —C(O)OR$_{12}$, —C(O)NR$_{13}$R$_{14}$; wherein:

$R_{10}$, $R_{11}$, $R_{13}$, and $R_{14}$ are each independently hydrogen, alkyl$_{(C \leq 12)}$, cycloalkyl$_{(C \leq 12)}$, aryl$_{(C \leq 12)}$, aralkyl$_{(C \leq 12)}$, acyl$_{(C \leq 12)}$, or a substituted version of any of these groups, or a monovalent amino protecting group; or $R_{10}$ and $R_{11}$ or $R_{13}$ and $R_{14}$ are taken together and are a divalent amino protecting group;

R''' and R'''' are hydrogen, alkyl$_{(C \leq 12)}$, cycloalkyl$_{(C \leq 12)}$, aryl$_{(C \leq 12)}$, aralkyl$_{(C \leq 12)}$, or a substituted version of any of these groups; and $R_{12}$ is alkyl$_{(C \leq 12)}$, cycloalkyl$_{(C \leq 12)}$, aryl$_{(C \leq 12)}$, aralkyl$_{(C \leq 12)}$, or a substituted version of any of these groups; or $R_9$ is alkyl$_{(C \leq 12)}$, cycloalkyl$_{(C \leq 12)}$, aryl$_{(C \leq 18)}$, heteroaryl$_{(C \leq 18)}$, heterocycloalkyl$_{(C \leq 12)}$, aralkyl$_{(C \leq 18)}$, heteroaralkyl$_{(C \leq 18)}$, alkoxy$_{(C \leq 12)}$, cycloalkoxy$_{(C \leq 12)}$, aryloxy$_{(C \leq 12)}$, aralkoxy$_{(C \leq 12)}$, or a substituted version of any of these eleven groups;

or a pharmaceutically acceptable salt thereof.

The compound may be further defined as:

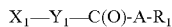

$$X_1-Y_1-C(O)\text{-}A\text{-}R_1 \quad \text{(II)}$$

wherein:

$X_1$ is aryl$_{(C \leq 12)}$, heteroaryl$_{(C \leq 12)}$, or a substituted version of either of these groups; or -arenediyl$_{(C \leq 12)}$-R$_2$, -heteroarenediyl$_{(C \leq 12)}$-R$_2$, or a substituted version thereof, wherein:

$R_2$ is —B(OR')(OR''), —NR$_3$R$_4$, —C(O)OR$_5$, —C(O)NR$_6$R$_7$; wherein:

$R_3$, $R_4$, $R_6$, and $R_7$ are each independently hydrogen, alkyl$_{(C \leq 12)}$, cycloalkyl$_{(C \leq 12)}$, aryl$_{(C \leq 12)}$, aralkyl$_{(C \leq 12)}$, acyl$_{(C \leq 12)}$, or a substituted version of any of these groups, or a monovalent amino protecting group; or $R_3$ and $R_4$ or $R_6$ and $R_7$ are taken together and are a divalent amino protecting group;

R' and R'' are hydrogen, alkyl$_{(C \leq 12)}$, cycloalkyl$_{(C \leq 12)}$, aryl$_{(C \leq 12)}$, aralkyl$_{(C \leq 12)}$, or a substituted version of any of these groups; and $R_5$ is alkyl$_{(C \leq 12)}$, cycloalkyl$_{(C \leq 12)}$, aryl$_{(C \leq 12)}$, aralkyl$_{(C \leq 12)}$, or a substituted version of any of these groups; or $R_2$ is alkyl$_{(C \leq 12)}$, cycloalkyl$_{(C \leq 12)}$, aryl$_{(C \leq 18)}$, heteroaryl$_{(C \leq 18)}$, heterocycloalkyl$_{(C \leq 12)}$, aralkyl$_{(C \leq 18)}$, heteroaralkyl$_{(C \leq 18)}$, alkoxy$_{(C \leq 12)}$, cycloalkoxy$_{(C \leq 12)}$, aryloxy$_{(C \leq 12)}$, aralkoxy$_{(C \leq 12)}$, or a substituted version of any of these eleven groups;

$Y_1$ is heteroarenediyl$_{(C \leq 12)}$ or substituted heteroarenediyl$_{(C \leq 12)}$;

A is —NR$_8$—, wherein:

$R_8$ is hydrogen, alkyl$_{(C \leq 8)}$, substituted alkyl$_{(C \leq 8)}$, cycloalkyl$_{(C \leq 8)}$, or substituted cycloalkyl$_{(C \leq 8)}$; or $R_8$ and $R_1$ are taken together and are heterocycloalkanediyl$_{(C \leq 12)}$, heteroarenediyl$_{(C \leq 12)}$, or a substituted version thereof; and $R_1$ is alkyl$_{(C \leq 12)}$, cycloalkyl$_{(C \leq 12)}$, aryl$_{(C \leq 18)}$, heteroaryl$_{(C \leq 18)}$, heterocycloalkyl$_{(C \leq 12)}$, aralkyl$_{(C \leq 18)}$, heteroaralkyl$_{(C \leq 18)}$, -alkanediyl$_{(C \leq 6)}$-heterocycloalkyl$_{(C \leq 12)}$, or a substituted version of any of these groups; or aryl$_{(C \leq 12)}$ or substituted aryl$_{(C \leq 12)}$, wherein two hydrogen atoms have been replaced with —NR$_a$C(O)NR$_b$—; or R$_1$ is taken together with R$_8$ as described above; wherein:

$R_a$ and $R_b$ are each independently hydrogen, alkyl$_{(C \leq 6)}$, substituted alkyl$_{(C \leq 6)}$, cycloalkyl$_{(C \leq 6)}$, or substituted cycloalkyl$_{(C \leq 6)}$; or $R_1$ is -arenediyl$_{(C \leq 12)}$-R$_9$, -heteroarenediyl$_{(C \leq 12)}$-R$_9$, or a substituted version thereof, wherein:

$R_9$ is —B(OR''')(OR''''), —NR$_{10}$R$_{11}$, —C(O)OR$_{12}$, —C(O)NR$_{13}$R$_{14}$; wherein:

$R_{10}$, $R_{11}$, $R_{13}$, and $R_{14}$ are each independently hydrogen, alkyl$_{(C \leq 12)}$, cycloalkyl$_{(C \leq 12)}$, aryl$_{(C \leq 12)}$, aralkyl$_{(C \leq 12)}$, acyl$_{(C \leq 12)}$, or a substituted version of any of these groups, or a monovalent amino protecting group; or $R_{10}$ and $R_{11}$ or $R_{13}$ and $R_{14}$ are taken together and are a divalent amino protecting group;

R''' and R'''' are hydrogen, alkyl$_{(C \leq 12)}$, cycloalkyl$_{(C \leq 12)}$, aryl$_{(C \leq 12)}$, aralkyl$_{(C \leq 12)}$, or a substituted version of any of these groups; and $R_{12}$ is alkyl$_{(C \leq 12)}$, cycloalkyl$_{(C \leq 12)}$, aryl$_{(C \leq 12)}$, aralkyl$_{(C \leq 12)}$, or a substituted version of any of these groups; or $R_9$ is alkyl$_{(C \leq 12)}$, cycloalkyl$_{(C \leq 12)}$, aryl$_{(C \leq 18)}$, heteroaryl$_{(C \leq 18)}$, heterocycloalkyl$_{(C \leq 12)}$, aralkyl$_{(C \leq 18)}$, heteroaralkyl$_{(C \leq 18)}$, alkoxy$_{(C \leq 12)}$, cycloalkoxy$_{(C \leq 12)}$, aryloxy$_{(C \leq 12)}$, aralkoxy$_{(C \leq 12)}$, or a substituted version of any of these eleven groups;

or a pharmaceutically acceptable salt thereof.

The compound may be further defined as:

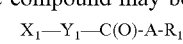

$$X_1-Y_1-C(O)\text{-}A\text{-}R_1 \quad \text{(II)}$$

wherein:

$X_1$ is aryl$_{(C \leq 12)}$, heteroaryl$_{(C \leq 12)}$, or a substituted version of either of these groups; or -arenediyl$_{(C \leq 12)}$-R$_2$, -heteroarenediyl$_{(C \leq 12)}$-R$_2$, or a substituted version thereof, wherein:

$R_2$ is —B(OR')(OR''), —NR$_3$R$_4$, —C(O)OR$_5$, —C(O)NR$_6$R$_7$; wherein:

$R_3$, $R_4$, $R_6$, and $R_7$ are each independently hydrogen, alkyl$_{(C \leq 12)}$, cycloalkyl$_{(C \leq 12)}$, aryl$_{(C \leq 12)}$, aralkyl$_{(C \leq 12)}$, acyl$_{(C \leq 12)}$, or a substituted version of any of these groups, or a monovalent amino protecting group; or $R_3$ and $R_4$ or $R_6$ and $R_7$ are taken together and are a divalent amino protecting group;

R' and R'' are hydrogen, alkyl$_{(C \leq 12)}$, cycloalkyl$_{(C \leq 12)}$, aryl$_{(C \leq 12)}$, aralkyl$_{(C \leq 12)}$, or a substituted version of any of these groups; and $R_5$ is alkyl$_{(C \leq 12)}$, cycloalkyl$_{(C \leq 12)}$, aryl$_{(C \leq 12)}$, aralkyl$_{(C \leq 12)}$, or a substituted version of any of these groups; or $R_2$ is alkyl$_{(C \leq 12)}$, cycloalkyl$_{(C \leq 12)}$, aryl$_{(C \leq 18)}$, heteroaryl$_{(C \leq 8)}$, heterocycloalkyl$_{(C \leq 12)}$, aralkyl$_{(C \leq 18)}$, heteroaralkyl$_{(C \leq 18)}$, alkoxy$_{(C \leq 12)}$, cycloalkoxy$_{(C \leq 12)}$, aryloxy$_{(C \leq 12)}$, aralkoxy$_{(C \leq 12)}$, or a substituted version of any of these eleven groups;

$Y_1$ is heteroarenediyl$_{(C \leq 12)}$ or substituted heteroarenediyl$_{(C \leq 12)}$;

A is —NR$_8$—, wherein:
$R_8$ is hydrogen, alkyl$_{(C \leq 8)}$, substituted alkyl$_{(C \leq 8)}$, cycloalkyl$_{(C \leq 8)}$, or substituted cycloalkyl$_{(C \leq 8)}$; or
$R_8$ and $R_1$ are taken together and are heterocycloalkanediyl$_{(C \leq 12)}$, heteroarenediyl$_{(C \leq 12)}$, or a substituted version thereof;
$R_1$ is aryl$_{(C \leq 18)}$, heteroaryl$_{(C \leq 18)}$, heterocycloalkyl$_{(C \leq 12)}$, aralkyl$_{(C \leq 18)}$, or a substituted version of any of these groups;
or a pharmaceutically acceptable salt thereof.

The compound may be further defined as:

$$X_1\text{—}Y_1\text{—}C(O)\text{-}A\text{-}R_1 \quad (II)$$

wherein:
$X_1$ is aryl$_{(C \leq 12)}$, heteroaryl$_{(C \leq 12)}$, or a substituted version of either of these groups;
$Y_1$ is heteroarenediyl$_{(C \leq 12)}$ or substituted heteroarenediyl$_{(C \leq 12)}$;
A is —NR$_8$—, wherein:
$R_8$ is hydrogen, alkyl$_{(C \leq 8)}$, substituted alkyl$_{(C \leq 8)}$, cycloalkyl$_{(C \leq 8)}$, or substituted cycloalkyl$_{(C \leq 8)}$; or
$R_8$ and $R_1$ are taken together and are heterocycloalkanediyl$_{(C \leq 12)}$, heteroarenediyl$_{(C \leq 12)}$, or a substituted version thereof;
$R_1$ is aryl$_{(C \leq 18)}$, heteroaryl$_{(C \leq 18)}$, heterocycloalkyl$_{(C \leq 12)}$, aralkyl$_{(C \leq 18)}$, or a substituted version of any of these groups;
or a pharmaceutically acceptable salt thereof.

The compounds as defined above may have $Y_1$ as a 4 to 8 membered heteroarenediyl$_{(C \leq 12)}$ or substituted heteroarenediyl$_{(C \leq 12)}$, or $Y_1$ as a 5 membered heteroarenediyl$_{(C \leq 12)}$ or substituted heteroarenediyl$_{(C \leq 12)}$, or $Y_1$ as thiophendiyl or pyrazoldiyl. The compounds as defined above may have $X_1$ as aryl$_{(C \leq 12)}$ or substituted aryl$_{(C \leq 12)}$, $X_1$ as aryl$_{(C \leq 12)}$, $X_1$ as phenyl, methylphenyl, dimethylphenyl, isopropylphenyl, isobutylphenyl, tert-butylphenyl, napthanyl, or indanyl, $X_1$ as substituted aryl$_{(C \leq 12)}$, $X_1$ as chlorophenyl, fluorophenyl, hydroxyphenyl, methoxyphenyl, cyanophenyl, or trifluoromethylphenyl, $X_1$ as hydroxyphenyl, $X_1$ as heteroaryl$_{(C \leq 12)}$ or substituted heteroaryl$_{(C \leq 12)}$, $X_1$ as heteroaryl$_{(C \leq 12)}$, $X_1$ as indolyl, thiophenyl, or pyridinyl, $X_1$ as arenediyl$_{(C \leq 12)}$R$_2$, such as where the arenediyl$_{(C \leq 12)}$ is phendiyl, wherein $R_2$ is alkoxy$_{(C \leq 12)}$ or isopropoxy, or wherein $R_2$ is NR$_3$R$_4$, $R_3$ is a monovalent amino protecting group, and/or wherein $R_4$ is hydrogen. $R_2$ may also be B(OR')(OR"), such as R' is hydrogen, and/or wherein R" is hydrogen. $R_2$ may also be C(O)R$_{15}$, wherein $R_{15}$ may be alkyl$_{(C \leq 12)}$ or substituted alkyl$_{(C \leq 12)}$, such as trifluoromethyl. $R_2$ may also be SO$_2$R$_{16}$, wherein $R_{16}$ is alkyl$_{(C \leq 12)}$ or substituted alkyl$_{(C \leq 12)}$, such as methyl.

The compounds as defined above may have A as —NR$_8$—, such as where $R_8$ is hydrogen. In this embodiment, $R_1$ and $R_8$ may be taken together and are heterocycloalkanediyl$_{(C \leq 12)}$ or substituted heterocycloalkanediyl$_{(C \leq 12)}$.

The compounds as defined above may have $R_1$ as aryl$_{(C \leq 12)}$ or substituted aryl$_{(C \leq 12)}$, such as phenyl, methylphenyl, or napthanyl, or chlorophenyl, fluorophenyl, or hydroxyphenyl. $R_1$ may be heteroaryl$_{(C \leq 12)}$ or substituted heteroaryl$_{(C \leq 12)}$, such as pyridinyl. $R_1$ may be arenediyl$_{(C \leq 12)}$-R$_9$, such as wherein the arenediyl$_{(C \leq 12)}$ is phendiyl, and/or $R_9$ is alkoxy$_{(C \leq 12)}$ or isopropoxy.

More particularly, the compound according to the above formulas and descriptions may be further defined as

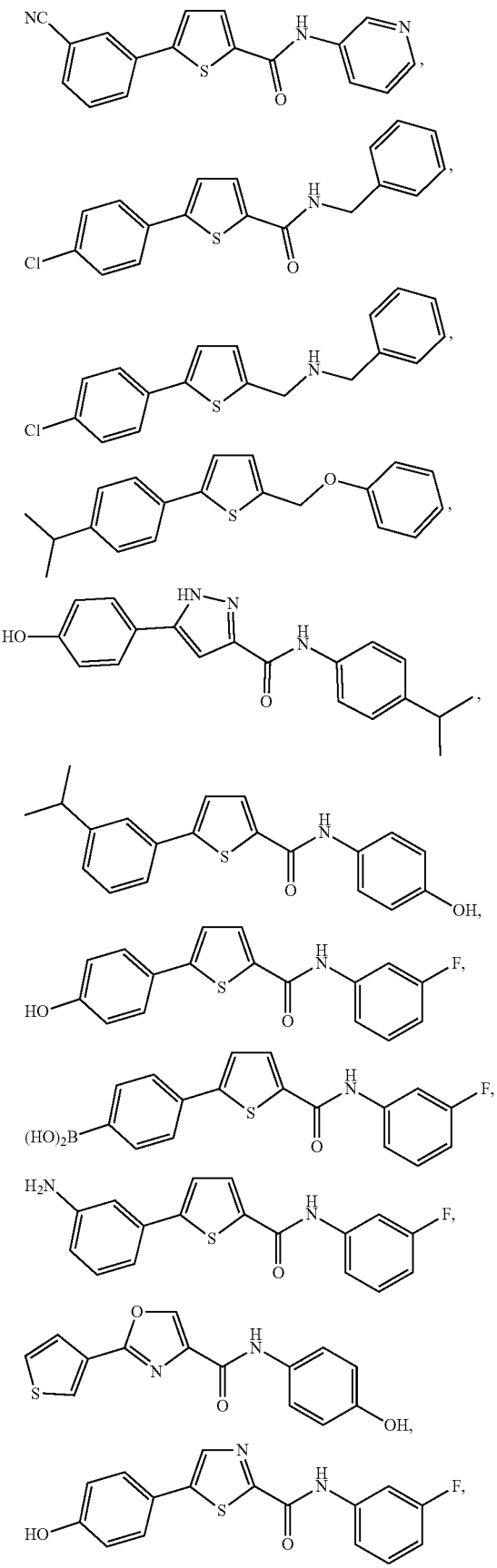

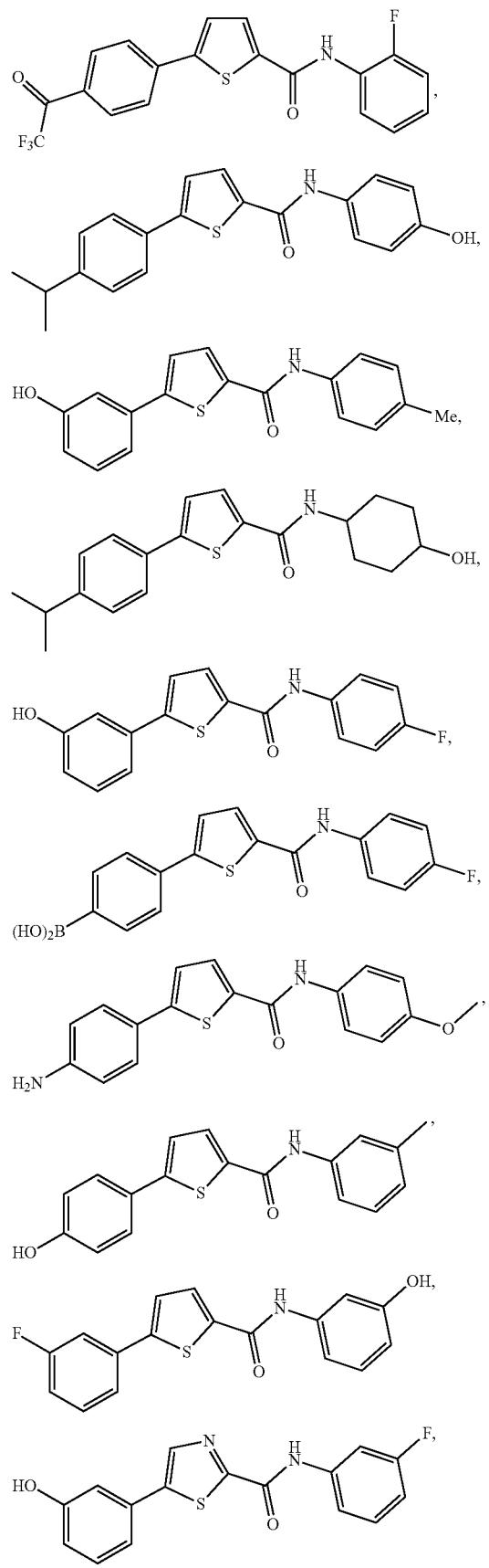
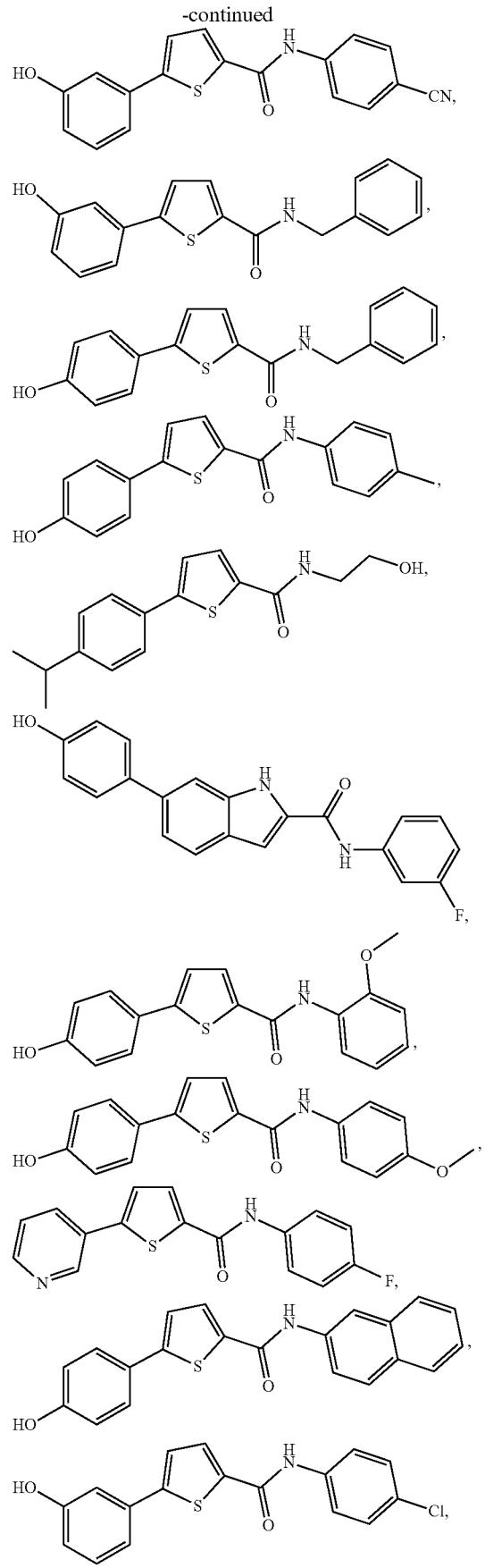

-continued
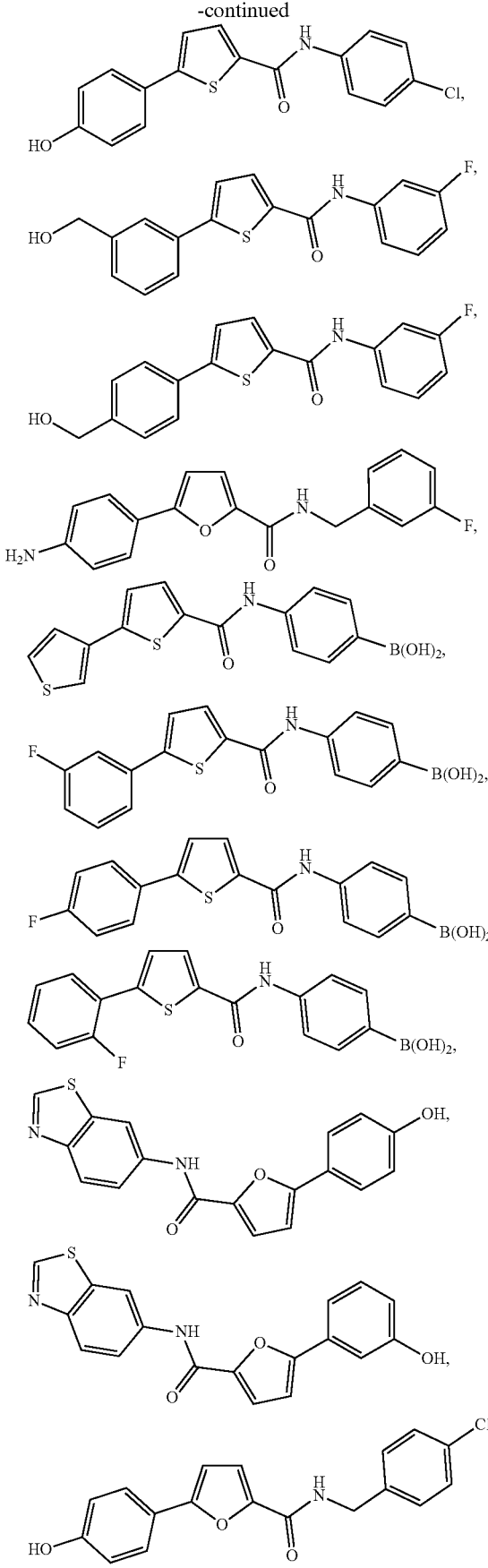
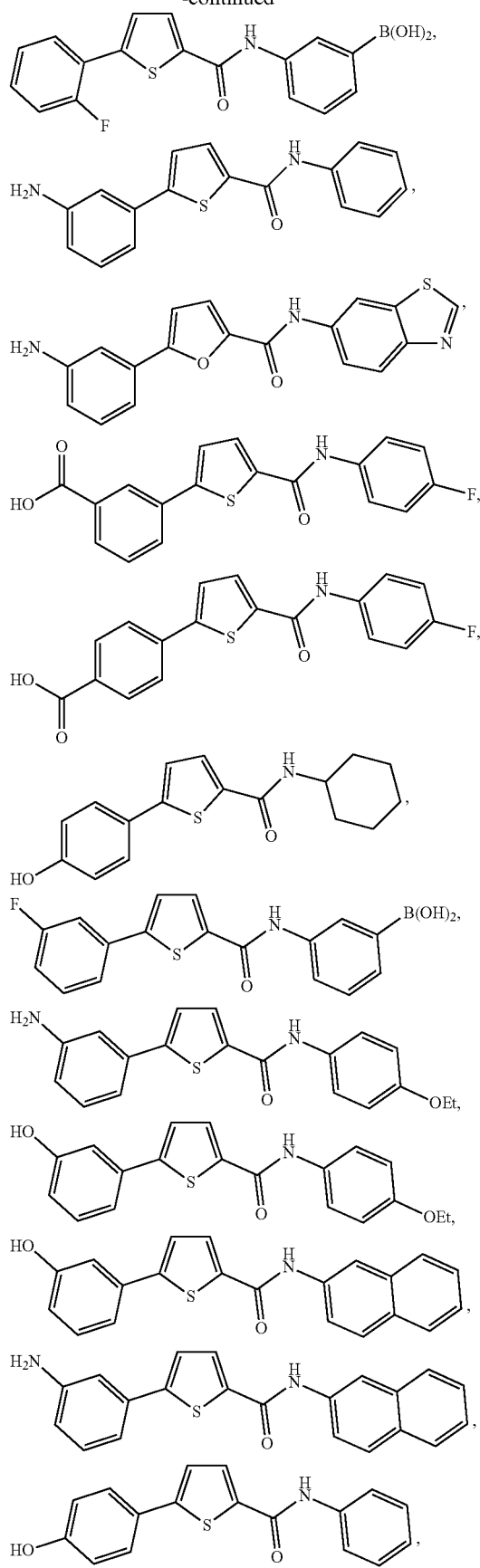

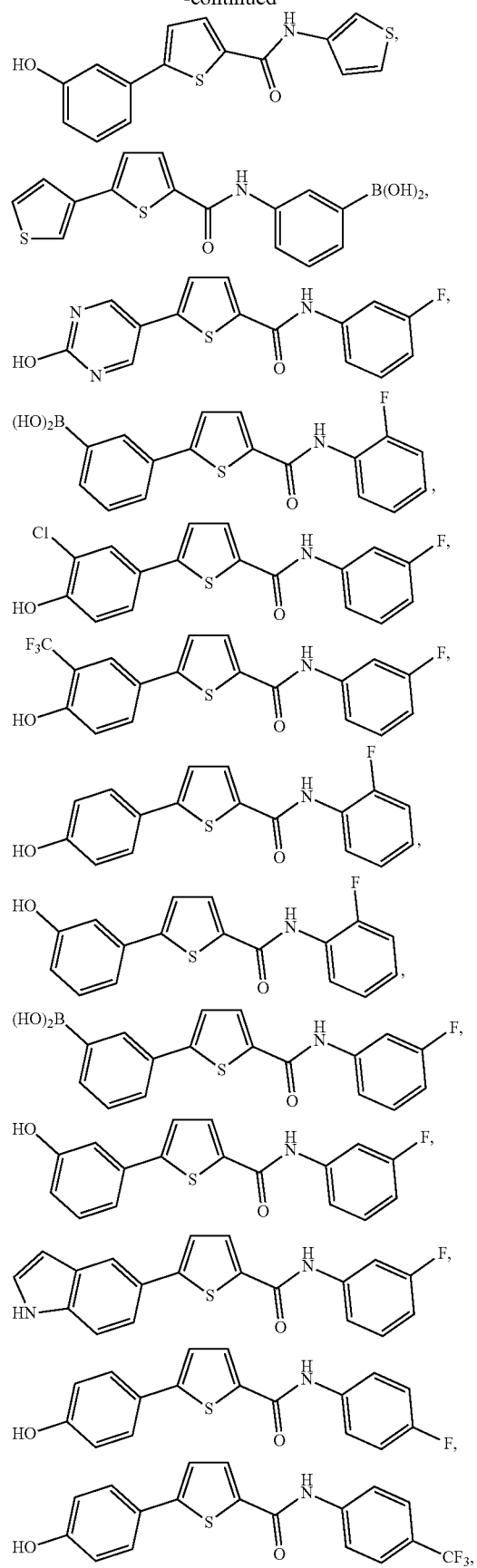
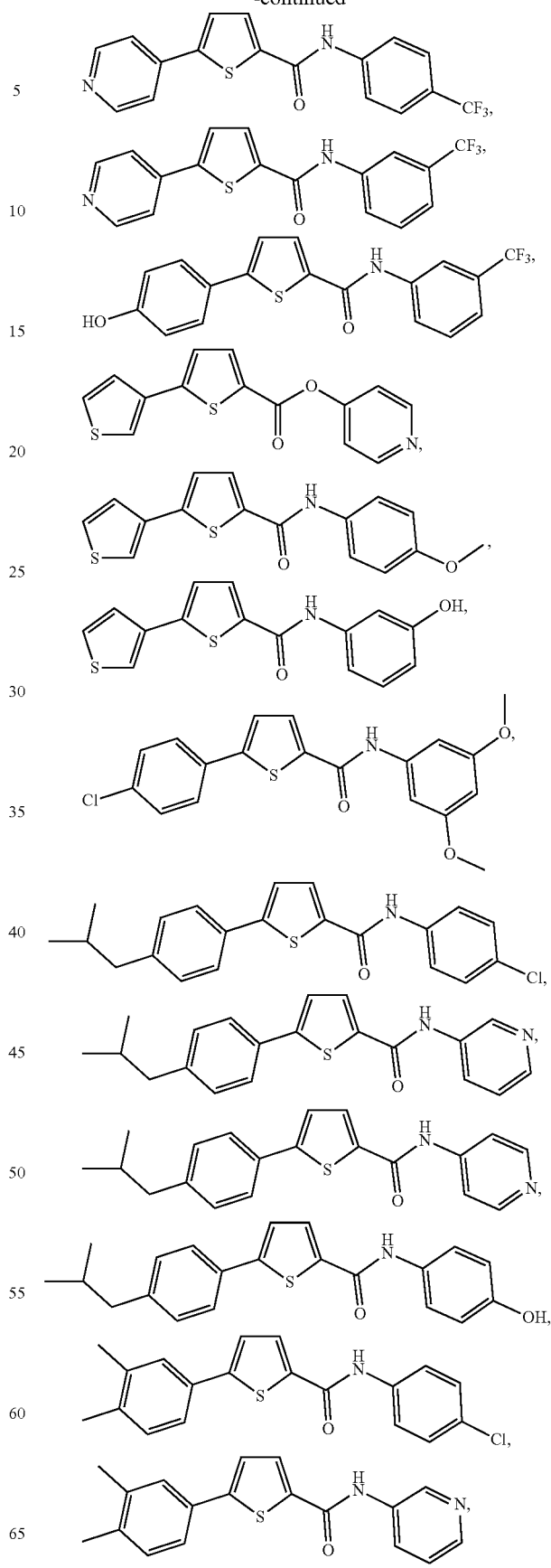

-continued
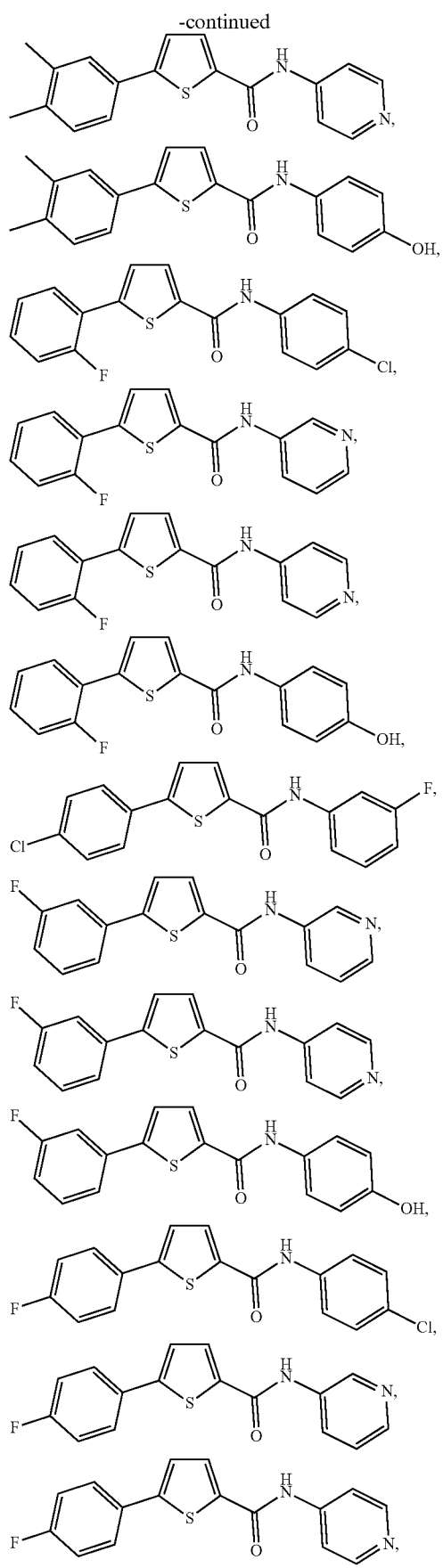
-continued
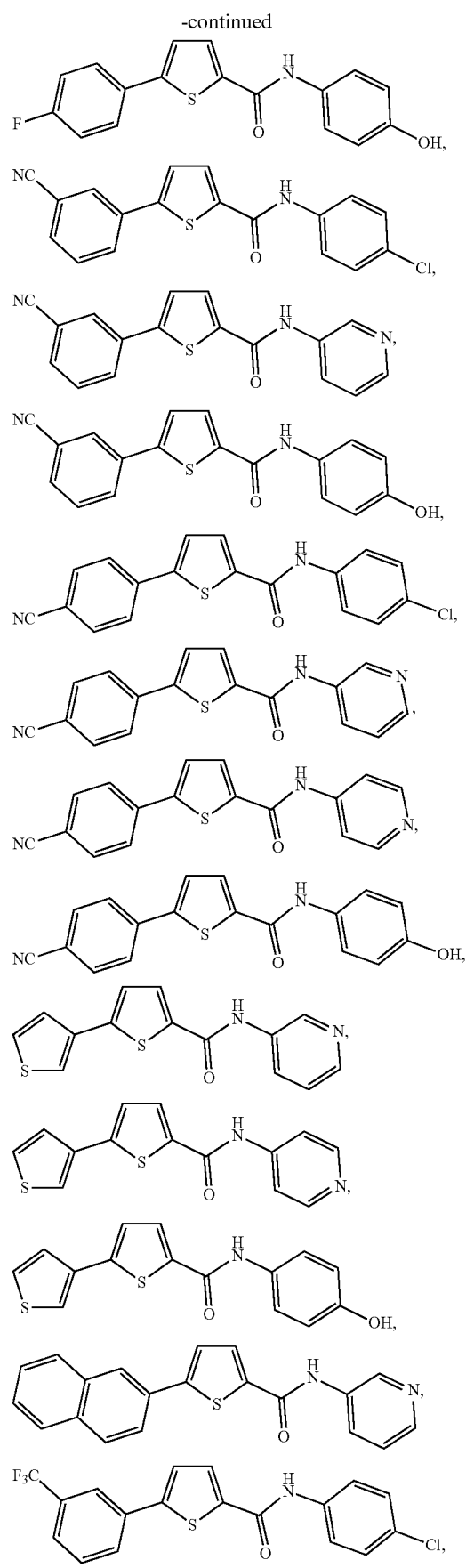

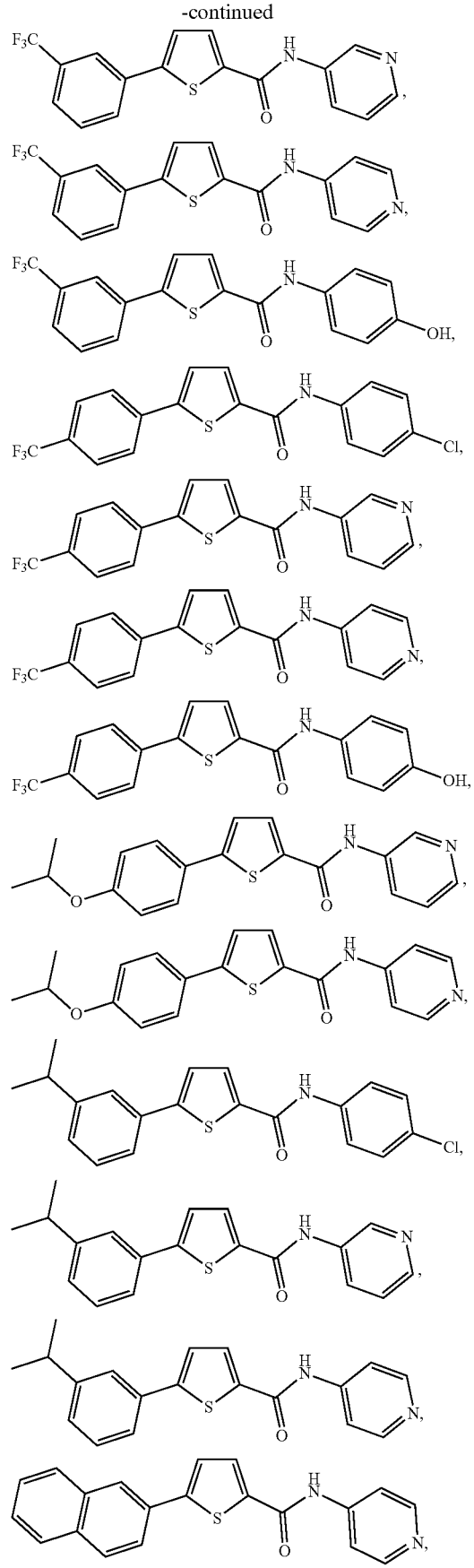
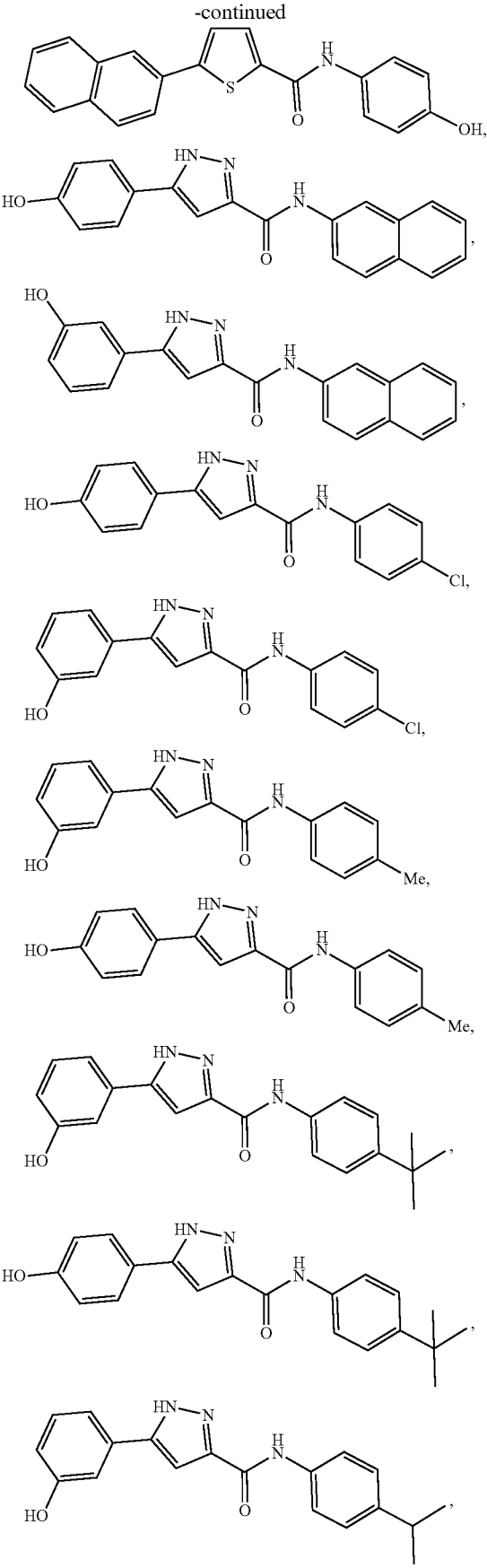

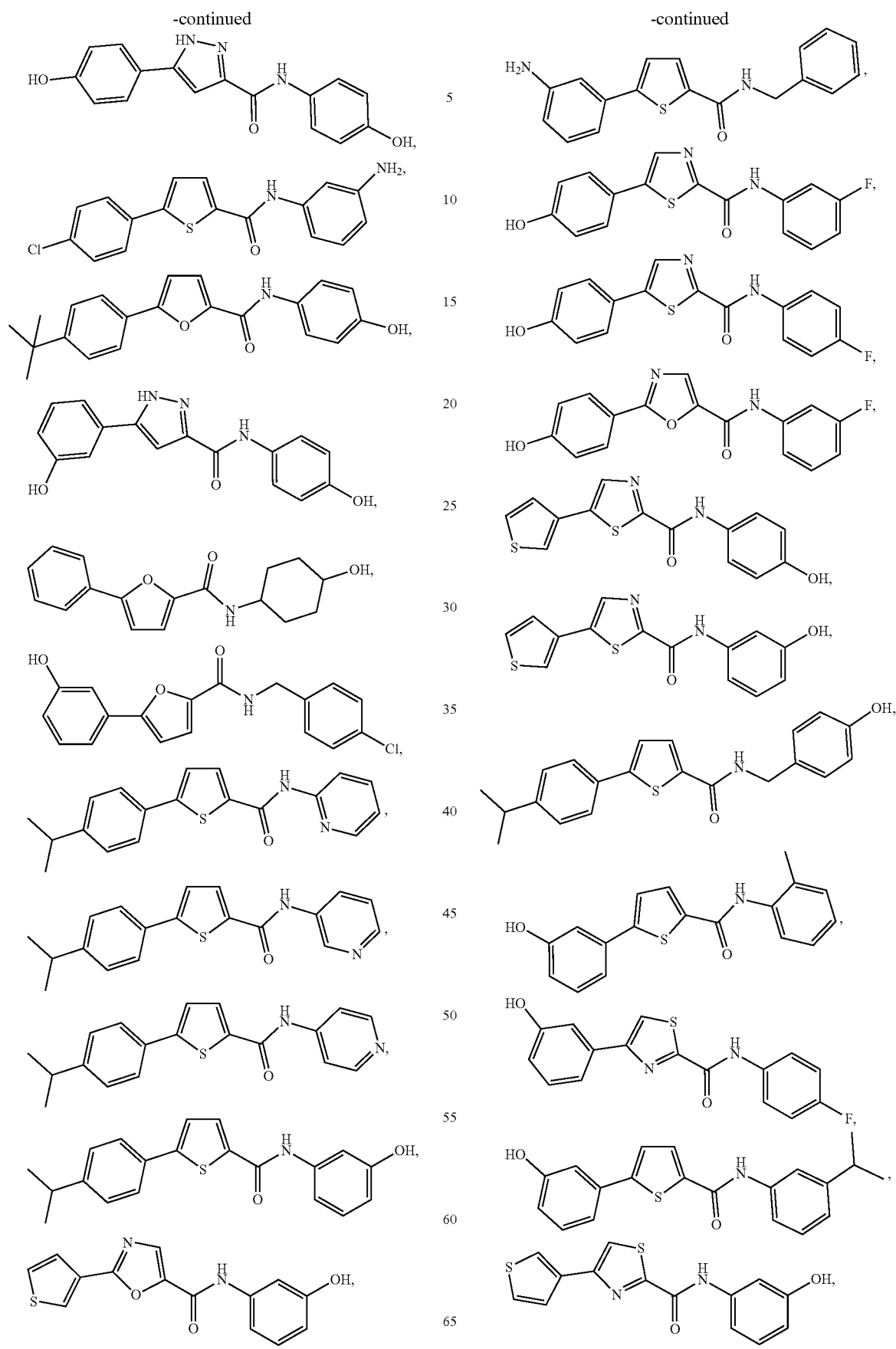

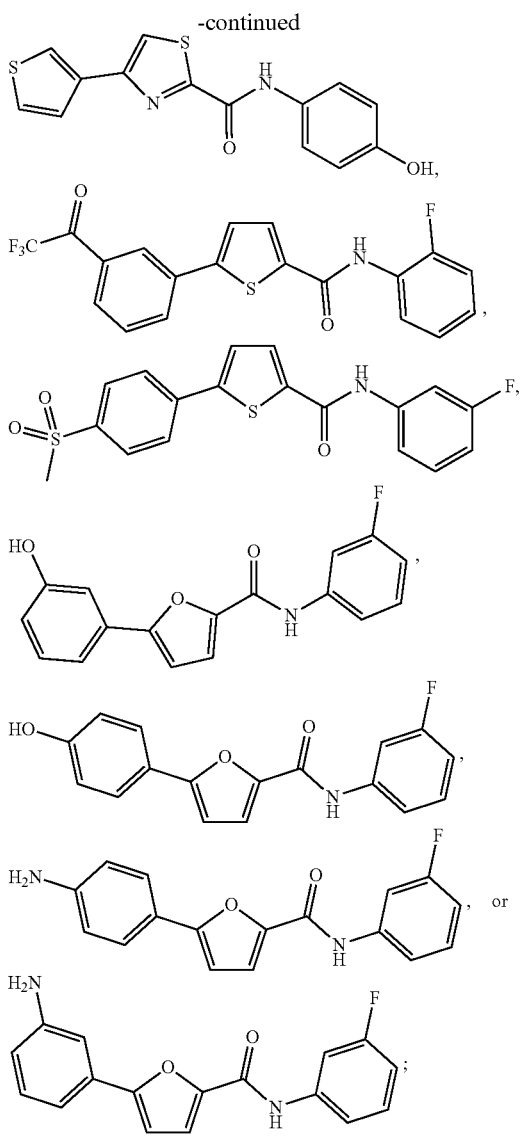

or a pharmaceutically acceptable salt thereof.

In another embodiment, there is provide a pharmaceutical composition comprising (a) a compound as defined above; and (b) an excipient. The pharmaceutical composition may be formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. The pharmaceutical composition may be formulated as a unit dose.

In yet another embodiment, there is provided a method of treating a metabolic disease or disorder in a patient comprising administering to the patient in need thereof a therapeutically effective amount of a compound or composition as defined above. The disease or disorder may be obesity, diabetes, a muscular dystrophy, non-alcoholic fatty liver disease. Alternatively, the disease or disorder may be a neurological disease or disorder. The method may further comprise a second therapy. The patient may be a mammal, such as a human. The method may comprise administering the compound once, such as two or more times.

It is contemplated that any method or composition described herein can be implemented with respect to any other method or composition described herein. For example, a compound synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

FIG. 1 shows the assay format for this FIGURE is the Gal4-DNA binding domain (DBD); ERRγ ligand binding domain (LBD) chimeric receptor cotransfection assay.

DESCRIPTION OF ILLUSTRATIVE EMBODIMENTS

Although endogenous ligands for the ERs have shown no activity at the ERRs, some synthetic ligands have been demonstrated to modulate the activity of both the ERs and ERRs. Diethylstilbesterol, a synthetic ER agonist, has been demonstrated to function as an inverse agonist/antagonist for all three ERRs (Tremblay et al., 2001a). Tamoxifen, a synthetic ER antagonist, functions as an inverse agonist for ERR and ERRγ, but displays no activity at ERRα (Coward et al., 2001; Tremblay et al., 2001b). Additionally, a few ERR selective ligands have been identified: XCT790 an ERRα selective inverse agonist (Busch et al., 2004) and GSK4716 an ERRβ/γ selective agonist (Zuercher et al., 2005). There are currently few selective ERR compounds that have been identified in the literature.

Thus, the goal of this research project is to develop a variety of synthetic ERRγ ligands, including α-, β- and γ-specific ligands, as well as pan-binding ligands, with sufficient pharmacokinetic properties so as to permit use in vivo. As indicated in the results presented herein, the inventors have indeed developed a number of ERR inverse agonists with varying ranges of activity. These and other aspects of the disclosure are set out in detail below.

I. COMPOUNDS AND FORMULATIONS THEREOF

A. Compounds

The compounds provided by the present disclosure are shown, for example, above in the summary section and in the examples and claims below. They may be made using standard methods using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein. Compounds described herein can be found in the Table below or in Example 3.

TABLE 1

Table of the Compounds

| Compound # | Structure |
|---|---|
| 1 | [structure] |
| 2 | [structure] |
| 3 | [structure] |
| 4 | [structure] |
| 5 | [structure] |
| 6 | [structure] |
| 7 | [structure] |
| 8 | [structure] |
| 9 | [structure] |
| 10 | [structure] |
| 11 | [structure] |
| 12 | [structure] |
| 13 | [structure] |
| 14 | [structure] |
| 15 | [structure] |
| 16 | [structure] |

TABLE 1-continued

Table of the Compounds

| Compound # | Structure |
|---|---|
| 17 | 4-(HO)₂B-phenyl-thiophene-2-carboxamide with N-(4-fluorophenyl) |
| 18 | 4-H₂N-phenyl-thiophene-2-carboxamide with N-(4-methoxyphenyl) |
| 19 | 4-HO-phenyl-thiophene-2-carboxamide with N-(3-methylphenyl) |
| 20 | 3-F-phenyl-thiophene-2-carboxamide with N-(3-hydroxyphenyl) |
| 21 | 3-HO-phenyl-thiazole-2-carboxamide with N-(3-fluorophenyl) |
| 22 | 3-HO-phenyl-thiophene-2-carboxamide with N-(4-cyanophenyl) |
| 23 | 3-HO-phenyl-thiophene-2-carboxamide with N-benzyl |
| 24 | 4-HO-phenyl-thiophene-2-carboxamide with N-benzyl |
| 25 | 4-HO-phenyl-thiophene-2-carboxamide with N-(4-methylphenyl) |
| 26 | 4-isopropyl-phenyl-thiophene-2-carboxamide with N-(2-hydroxyethyl) |
| 27 | 6-(4-hydroxyphenyl)-1H-indole-2-carboxamide with N-(3-fluorophenyl) |
| 28 | 4-HO-phenyl-thiophene-2-carboxamide with N-(2-methoxyphenyl) |
| 29 | 4-HO-phenyl-thiophene-2-carboxamide with N-(4-methoxyphenyl) |
| 30 | pyridin-3-yl-thiophene-2-carboxamide with N-(4-fluorophenyl) |
| 31 | 4-HO-phenyl-thiophene-2-carboxamide with N-(naphthalen-2-yl) |
| 32 | 3-HO-phenyl-thiophene-2-carboxamide with N-(4-chlorophenyl) |

TABLE 1-continued
Table of the Compounds
| Compound # | Structure |
|---|---|
| 33 | 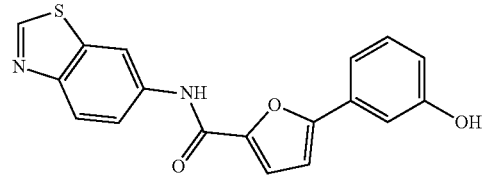 |
| 34 | 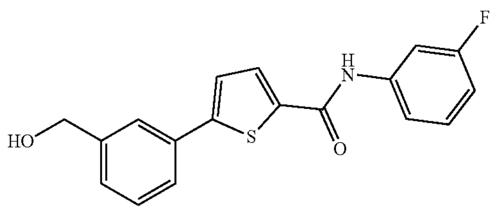 [SMILES: O=C(Nc1cccc(F)c1)c1ccc(-c2cccc(CO)c2)s1] |
| 35 | 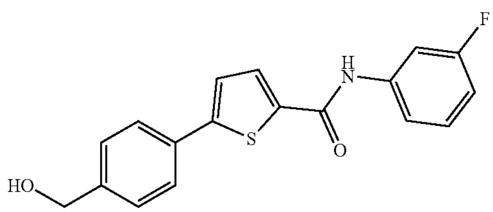 [SMILES: O=C(Nc1cccc(F)c1)c1ccc(-c2ccc(CO)cc2)s1] |
| 36 | 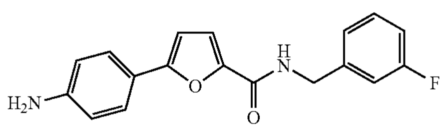 [SMILES: Nc1ccc(-c2ccc(C(=O)NCc3cccc(F)c3)o2)cc1] |
| 37 | 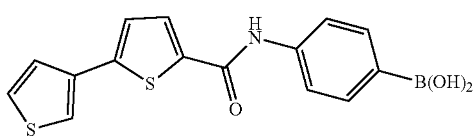 [SMILES: O=C(Nc1ccc(B(O)O)cc1)c1ccc(-c2ccsc2)s1] |
| 38 | 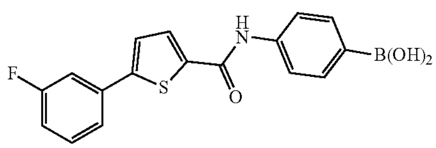 [SMILES: O=C(Nc1ccc(B(O)O)cc1)c1ccc(-c2cccc(F)c2)s1] |
| 39 | 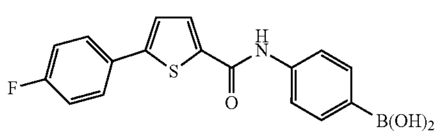 [SMILES: O=C(Nc1ccc(B(O)O)cc1)c1ccc(-c2ccc(F)cc2)s1] |
| 40 | 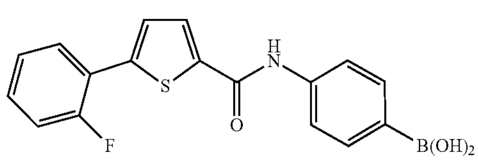 [SMILES: O=C(Nc1ccc(B(O)O)cc1)c1ccc(-c2ccccc2F)s1] |
| 41 | 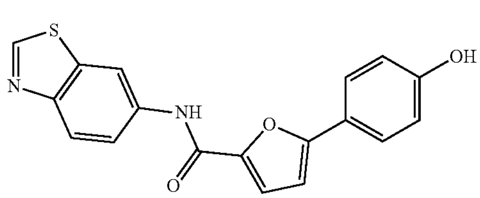 [SMILES: O=C(Nc1ccc2ncsc2c1)c1ccc(-c2ccc(O)cc2)o1] |
| 42 | 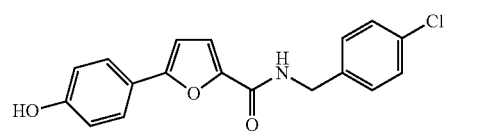 [SMILES: O=C(NCc1ccc(Cl)cc1)c1ccc(-c2ccc(O)cc2)o1] |
| 43 | |
| 44 | |
| 45 | |
| 46 | |
| 47 | |
| 48 | |
| 49 | |

TABLE 1-continued
Table of the Compounds
| Compound # | Structure |
|---|---|
| 50 | 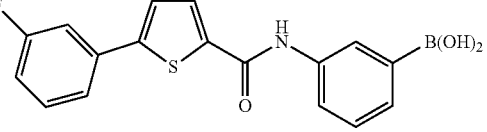 |
| 51 | 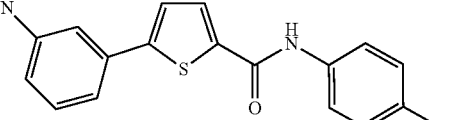 |
| 52 | 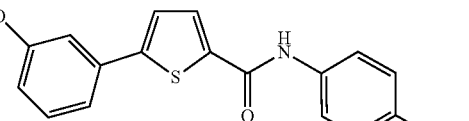 |
| 53 | 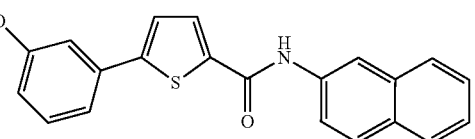 |
| 54 | 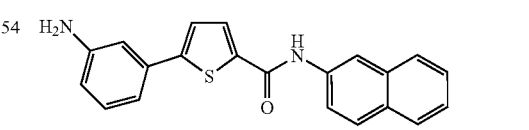 |
| 55 | 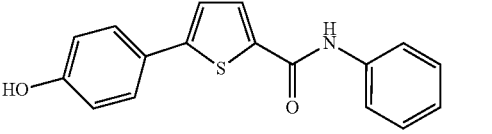 [SMILES: O=C(Nc1ccccc1)c1ccc(-c2ccc(O)cc2)s1] |
| 56 | 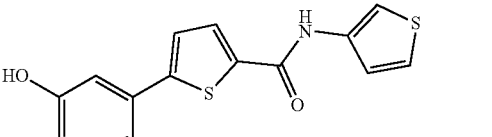 |
| 57 | 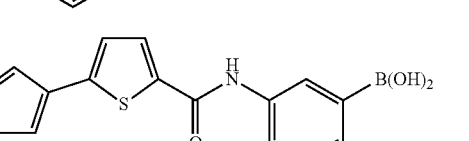 |
| 58 | 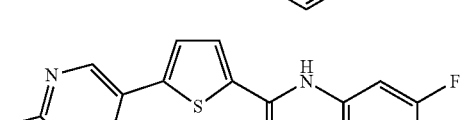 |
| 59 | 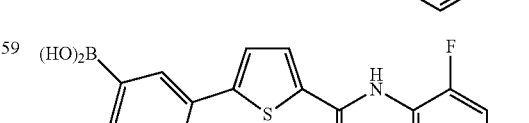 |
| 60 | 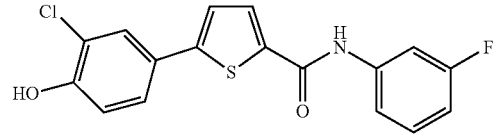 [SMILES: O=C(Nc1cccc(F)c1)c1ccc(-c2ccc(O)c(C(F)(F)F)c2)s1] |
| 61 | 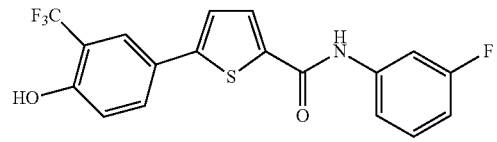 |
| 62 | 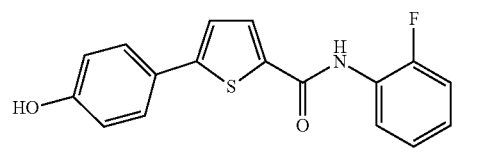 [SMILES: O=C(Nc1ccccc1F)c1ccc(-c2ccc(O)cc2)s1] |
| 63 | 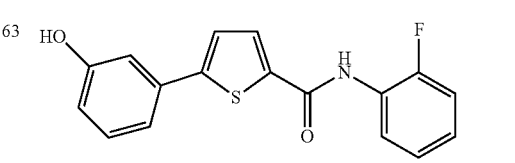 |
| 64 | 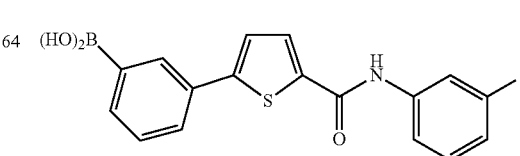 |
| 65 | 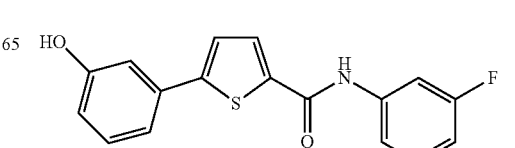 |
| 66 | 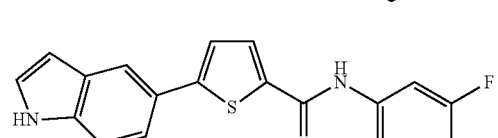 |
| 67 | 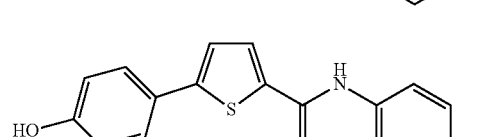 |
| 68 | 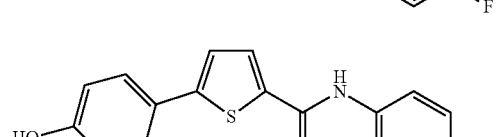 |

TABLE 1-continued

Table of the Compounds

| Compound # | Structure |
|---|---|
| 69 | 5-(pyridin-4-yl)-N-(4-(trifluoromethyl)phenyl)thiophene-2-carboxamide |
| 70 | 5-(pyridin-4-yl)-N-(3-(trifluoromethyl)phenyl)thiophene-2-carboxamide |
| 71 | 5-(4-hydroxyphenyl)-N-(3-(trifluoromethyl)phenyl)thiophene-2-carboxamide |
| 72 | pyridin-4-yl 2,3'-bithiophene-5-carboxylate |
| 73 | N-(4-methoxyphenyl)-2,3'-bithiophene-5-carboxamide |
| 74 | N-(3-hydroxyphenyl)-2,3'-bithiophene-5-carboxamide |
| 75 | 5-(4-chlorophenyl)-N-(3,5-dimethoxyphenyl)thiophene-2-carboxamide |
| 76 | N-(4-chlorophenyl)-5-(4-isobutylphenyl)thiophene-2-carboxamide |
| 77 | 5-(4-isobutylphenyl)-N-(pyridin-3-yl)thiophene-2-carboxamide |
| 78 | 5-(4-isobutylphenyl)-N-(pyridin-4-yl)thiophene-2-carboxamide |
| 79 | N-(4-hydroxyphenyl)-5-(4-isobutylphenyl)thiophene-2-carboxamide |
| 80 | N-(4-chlorophenyl)-5-(3,4-dimethylphenyl)thiophene-2-carboxamide |
| 81 | 5-(3,4-dimethylphenyl)-N-(pyridin-3-yl)thiophene-2-carboxamide |
| 82 | 5-(3,4-dimethylphenyl)-N-(pyridin-4-yl)thiophene-2-carboxamide |
| 83 | 5-(3,4-dimethylphenyl)-N-(4-hydroxyphenyl)thiophene-2-carboxamide |
| 84 | N-(4-chlorophenyl)-5-(2-fluorophenyl)thiophene-2-carboxamide |
| 85 | 5-(2-fluorophenyl)-N-(pyridin-3-yl)thiophene-2-carboxamide |
| 86 | 5-(2-fluorophenyl)-N-(pyridin-4-yl)thiophene-2-carboxamide |
| 87 | 5-(2-fluorophenyl)-N-(4-hydroxyphenyl)thiophene-2-carboxamide |
| 88 | 5-(4-chlorophenyl)-N-(3-fluorophenyl)thiophene-2-carboxamide |

TABLE 1-continued

Table of the Compounds

| Compound # | Structure |
|---|---|
| 89 | 3-fluorophenyl-thiophene-2-carboxamide-N-(pyridin-3-yl) |
| 90 | 3-fluorophenyl-thiophene-2-carboxamide-N-(pyridin-4-yl) |
| 91 | 3-fluorophenyl-thiophene-2-carboxamide-N-(4-hydroxyphenyl) |
| 92 | 4-fluorophenyl-thiophene-2-carboxamide-N-(4-chlorophenyl) |
| 93 | 4-fluorophenyl-thiophene-2-carboxamide-N-(pyridin-3-yl) |
| 94 | 4-fluorophenyl-thiophene-2-carboxamide-N-(pyridin-4-yl) |
| 95 | 4-fluorophenyl-thiophene-2-carboxamide-N-(4-hydroxyphenyl) |
| 96 | 3-cyanophenyl-thiophene-2-carboxamide-N-(4-chlorophenyl) |
| 97 | 3-cyanophenyl-thiophene-2-carboxamide-N-(pyridin-3-yl) |
| 98 | 3-cyanophenyl-thiophene-2-carboxamide-N-(4-hydroxyphenyl) |
| 99 | 4-cyanophenyl-thiophene-2-carboxamide-N-(4-chlorophenyl) |
| 100 | 4-cyanophenyl-thiophene-2-carboxamide-N-(pyridin-3-yl) |
| 101 | 4-cyanophenyl-thiophene-2-carboxamide-N-(pyridin-4-yl) |
| 102 | 4-cyanophenyl-thiophene-2-carboxamide-N-(4-hydroxyphenyl) |
| 103 | 3-thienyl-thiophene-2-carboxamide-N-(pyridin-3-yl) |
| 104 | 3-thienyl-thiophene-2-carboxamide-N-(pyridin-4-yl) |
| 105 | 3-thienyl-thiophene-2-carboxamide-N-(4-hydroxyphenyl) |
| 106 | naphthalen-2-yl-thiophene-2-carboxamide-N-(pyridin-3-yl) |
| 107 | 3-trifluoromethylphenyl-thiophene-2-carboxamide-N-(4-chlorophenyl) |
| 108 | 3-trifluoromethylphenyl-thiophene-2-carboxamide-N-(pyridin-3-yl) |

TABLE 1-continued

Table of the Compounds

| Compound # | Structure |
|---|---|
| 109 | 3-(trifluoromethyl)phenyl-thiophene-2-carboxamide-N-(pyridin-4-yl) |
| 110 | 3-(trifluoromethyl)phenyl-thiophene-2-carboxamide-N-(4-hydroxyphenyl) |
| 111 | 4-(trifluoromethyl)phenyl-thiophene-2-carboxamide-N-(4-chlorophenyl) |
| 112 | 4-(trifluoromethyl)phenyl-thiophene-2-carboxamide-N-(pyridin-3-yl) |
| 113 | 4-(trifluoromethyl)phenyl-thiophene-2-carboxamide-N-(pyridin-4-yl) |
| 114 | 4-(trifluoromethyl)phenyl-thiophene-2-carboxamide-N-(4-hydroxyphenyl) |
| 115 | 4-isopropoxyphenyl-thiophene-2-carboxamide-N-(pyridin-3-yl) |
| 116 | 4-isopropoxyphenyl-thiophene-2-carboxamide-N-(pyridin-4-yl) |
| 117 | 3-isopropylphenyl-thiophene-2-carboxamide-N-(4-chlorophenyl) |
| 118 | 3-isopropylphenyl-thiophene-2-carboxamide-N-(pyridin-3-yl) |
| 119 | 3-isopropylphenyl-thiophene-2-carboxamide-N-(pyridin-4-yl) |
| 120 | naphthalen-2-yl-thiophene-2-carboxamide-N-(pyridin-4-yl) |
| 121 | naphthalen-2-yl-thiophene-2-carboxamide-N-(4-hydroxyphenyl) |
| 122 | 5-(4-hydroxyphenyl)-1H-pyrazole-3-carboxamide-N-(naphthalen-2-yl) |
| 123 | 5-(3-hydroxyphenyl)-1H-pyrazole-3-carboxamide-N-(naphthalen-2-yl) |
| 124 | 5-(4-hydroxyphenyl)-1H-pyrazole-3-carboxamide-N-(4-chlorophenyl) |
| 125 | 5-(3-hydroxyphenyl)-1H-pyrazole-3-carboxamide-N-(4-chlorophenyl) |
| 126 | 5-(3-hydroxyphenyl)-1H-pyrazole-3-carboxamide-N-(4-methylphenyl) |
| 127 | 5-(4-hydroxyphenyl)-1H-pyrazole-3-carboxamide-N-(4-methylphenyl) |

TABLE 1-continued

Table of the Compounds

| Compound # | Structure |
|---|---|
| 128 | 3-hydroxyphenyl-1H-pyrazole-3-carboxamide N-(4-tert-butylphenyl) |
| 129 | 4-hydroxyphenyl-1H-pyrazole-3-carboxamide N-(4-tert-butylphenyl) |
| 130 | 3-hydroxyphenyl-1H-pyrazole-3-carboxamide N-(4-isopropylphenyl) |
| 131 | 4-hydroxyphenyl-1H-pyrazole-3-carboxamide N-(4-hydroxyphenyl) |
| 132 | 5-(4-chlorophenyl)thiophene-2-carboxamide N-(3-aminophenyl) |
| 133 | 5-(4-tert-butylphenyl)furan-2-carboxamide N-(4-hydroxyphenyl) |
| 134 | 3-hydroxyphenyl-1H-pyrazole-3-carboxamide N-(4-hydroxyphenyl) |
| 135 | 5-phenylfuran-2-carboxamide N-(4-hydroxycyclohexyl) |
| 136 | 5-(3-hydroxyphenyl)furan-2-carboxamide N-(4-chlorobenzyl) |
| 137 | 5-(4-isopropylphenyl)thiophene-2-carboxamide N-(2-pyridyl) |
| 138 | 5-(4-isopropylphenyl)thiophene-2-carboxamide N-(3-pyridyl) |
| 139 | 5-(4-isopropylphenyl)thiophene-2-carboxamide N-(4-pyridyl) |
| 140 | 5-(4-isopropylphenyl)thiophene-2-carboxamide N-(3-hydroxyphenyl) |
| 141 | 2-(3-thienyl)oxazole-5-carboxamide N-(3-hydroxyphenyl) |
| 142 | 5-(3-aminophenyl)thiophene-2-carboxamide N-benzyl |
| 143 | 5-(4-hydroxyphenyl)thiazole-2-carboxamide N-(3-fluorophenyl) |
| 144 | 5-(4-hydroxyphenyl)thiazole-2-carboxamide N-(4-fluorophenyl) |
| 145 | 5-(4-hydroxyphenyl)oxazole-5-carboxamide N-(3-fluorophenyl) |
| 146 | 5-(3-thienyl)thiazole-2-carboxamide N-(4-hydroxyphenyl) |

TABLE 1-continued

Table of the Compounds

| Compound # | Structure |
|---|---|
| 147 | 5-(thiophen-3-yl)-N-(3-hydroxyphenyl)thiazole-2-carboxamide |
| 148 | 5-(4-isopropylphenyl)-N-(4-hydroxybenzyl)thiophene-2-carboxamide |
| 149 | 5-(3-hydroxyphenyl)-N-(2-methylphenyl)thiophene-2-carboxamide |
| 150 | 4-(3-hydroxyphenyl)-N-(4-fluorophenyl)thiazole-2-carboxamide |
| 151 | 5-(3-hydroxyphenyl)-N-(3-isopropylphenyl)thiophene-2-carboxamide |
| 152 | 4-(thiophen-3-yl)-N-(3-hydroxyphenyl)thiazole-2-carboxamide |
| 153 | 4-(thiophen-3-yl)-N-(4-hydroxyphenyl)thiazole-2-carboxamide |
| 154 | 5-(3-(trifluoroacetyl)phenyl)-N-(2-fluorophenyl)thiophene-2-carboxamide |
| 155 | 5-(4-(methylsulfonyl)phenyl)-N-(3-fluorophenyl)thiophene-2-carboxamide |
| 156 | 5-(3-hydroxyphenyl)-N-(3-fluorophenyl)furan-2-carboxamide |
| 157 | 5-(4-hydroxyphenyl)-N-(3-fluorophenyl)furan-2-carboxamide |
| 158 | 5-(4-aminophenyl)-N-(3-fluorophenyl)furan-2-carboxamide |
| 159 | 5-(3-aminophenyl)-N-(3-fluorophenyl)furan-2-carboxamide |

The compounds described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the (S) or the (R) configuration.

Chemical formulas used to represent the compounds described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The compounds described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The compounds described herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in Handbook of Pharmaceutical Salts: Properties, and Use (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the compounds described herein are within the scope of the disclosure. It will also be appreciated by those skilled in organic chemistry that many organic compounds can exist in more than one crystalline form. For example, crystalline form may vary from solvate to solvate. Thus, all crystalline forms of the compounds described herein are within the scope of the present disclosure.

B. Formulations

In some embodiments of the present disclosure, the compounds are included a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the compounds described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. METABOLIC DISEASES

Metabolic diseases include those caused by a wide range of metabolic defects, with varying manifestations. For example, obesity and diabetes are metabolic disorders that may be linked, or be found separately. Muscle wasting diseases, including various forms of muscular dystrophy, also are consider disorders with metabolic bases. Some of these conditions are described below.

A. Diabetes

Diabetes mellitus, often simply referred to as diabetes, is a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger).

There are three main types of diabetes:
- Type 1 diabetes: results from the body's failure to produce insulin, and presently requires the person to inject insulin. (Also referred to as insulin-dependent diabetes mellitus, IDDM for short, and juvenile diabetes.)
- Type 2 diabetes: results from insulin resistance, a condition in which cells fail to use insulin properly, and eventually combines with an absolute insulin deficiency. (Formerly referred to as non-insulin-dependent diabetes mellitus, NIDDM for short, and adult-onset diabetes.)

Gestational diabetes: is when pregnant women, who have never had diabetes before, have a high blood glucose level during pregnancy. It may precede development of type 2 diabetes mellitus.

Other forms of diabetes mellitus include congenital diabetes, which is due to genetic defects of insulin secretion, cystic fibrosis-related diabetes, steroid diabetes induced by high doses of glucocorticoids, and several forms of monogenic diabetes.

All forms of diabetes have been treatable since insulin became available in 1921, and type 2 diabetes may be controlled with medications. Both type 1 and 2 are chronic conditions that usually cannot be cured. Pancreas transplants have been tried with limited success in type 1 diabetes; gastric bypass surgery has been successful in many with morbid obesity and type 2 diabetes. Gestational diabetes usually resolves after delivery. Diabetes without proper treatments can cause many complications. Acute complications include hypoglycemia, diabetic ketoacidosis, or nonketotic hyperosmolar coma. Serious long-term complications include cardiovascular disease, chronic renal failure, retinal damage. Adequate treatment of diabetes is thus important, as well as blood pressure control and lifestyle factors such as smoking cessation and maintaining a healthy body weight.

Diabetes is a huge health burden, costing an estimated $174 billion in 2007. In the United States alone more than 23 million people, 8% of the population are diabetic; an additional 32% of adults are at risk with pre-diabetes, either impaired oral glucose tolerance or abnormally high fasting glucose (NIDDK, ADA statistics). This adds up to a staggeringly large proportion of the U.S. adult population with abnormal glucose metabolism. Worldwide, 230 million are affected by diabetes and the number is expected to double over the next 20 years. Currently, type 1 diabetes accounts for only 5% of the total. As obesity has become epidemic, type 2 diabetes has increased at an alarming rate. In spite of these daunting numbers, statistics also reveal that interventions that improve glycemic control reduce negative health consequences.

Most cases of diabetes mellitus fall into three broad categories: type 1, type 2, and gestational diabetes. A few other types are described. The term diabetes, without qualification, usually refers to diabetes mellitus. The rare disease diabetes insipidus has similar symptoms as diabetes mellitus, but without disturbances in the sugar metabolism.

The term "type 1 diabetes" has replaced several former terms, including childhood-onset diabetes, juvenile diabetes, and insulin-dependent diabetes mellitus (IDDM). Likewise, the term "type 2 diabetes" has replaced several former terms, including adult-onset diabetes, obesity-related diabetes, and non-insulin-dependent diabetes mellitus (NIDDM). Beyond these two types, there is no agreed-upon standard nomenclature. Various sources have defined "type 3 diabetes" as: gestational diabetes, insulin-resistant type 1 diabetes (or "double diabetes"), type 2 diabetes which has progressed to require injected insulin, and latent autoimmune diabetes of adults (or LADA or "type 1.5" diabetes).

Type 1 diabetes mellitus is characterized by loss of the insulin-producing beta cells of the islets of Langerhans in the pancreas leading to insulin deficiency. This type of diabetes can be further classified as immune-mediated or idiopathic. The majority of type 1 diabetes is of the immune-mediated nature, where β-cell loss is a T-cell mediated autoimmune attack. There is no known preventive measure against type 1 diabetes, which causes approximately 10% of diabetes mellitus cases in North America and Europe. Most affected people are otherwise healthy and of a healthy weight when onset occurs. Sensitivity and responsiveness to insulin are usually normal, especially in the early stages. Type 1 diabetes can affect children or adults but was traditionally termed "juvenile diabetes" because it represents a majority of the diabetes cases in children.

Type 2 diabetes mellitus is characterized by insulin resistance which may be combined with relatively reduced insulin secretion. The defective responsiveness of body tissues to insulin has an array of possible causes with obesity as a major factor. Diabetes mellitus occurrences linked to single gene mutations are known as maturity onset diabetes of the young or MODY and are classified separately. Type 2 diabetes is the most common type. In the early stage of type 2 diabetes, the predominant abnormality is reduced insulin sensitivity. At this stage hyperglycemia can be reversed by a variety of measures and medications that improve insulin sensitivity or reduce glucose production by the liver.

Gestational diabetes mellitus (GDM) resembles type 2 diabetes in several respects, involving a combination of relatively inadequate insulin secretion and responsiveness. It occurs in about 2%-5% of all pregnancies and may improve or disappear after delivery. Gestational diabetes is fully treatable but requires careful medical supervision throughout the pregnancy. About 20%-50% of affected women develop type 2 diabetes later in life. Even though it may be transient, untreated gestational diabetes can damage the health of the fetus or mother. Risks to the baby include macrosomia (high birth weight), congenital cardiac and central nervous system anomalies, and skeletal muscle malformations. Increased fetal insulin may inhibit fetal surfactant production and cause respiratory distress syndrome. Hyperbilirubinemia may result from red blood cell destruction. In severe cases, perinatal death may occur, most commonly as a result of poor placental perfusion due to vascular impairment. Labor induction may be indicated with decreased placental function. A cesarean section may be performed if there is marked fetal distress or an increased risk of injury associated with macrosomia, such as shoulder dystocia.

Some cases of diabetes are caused by the body's tissue receptors not responding to insulin (even when insulin levels are normal, which is what separates it from type 2 diabetes); this form is very uncommon. Genetic mutations (autosomal or mitochondrial) can lead to defects in beta cell function. Abnormal insulin action may also have been genetically determined in some cases. Any disease that causes extensive damage to the pancreas may lead to diabetes (for example, chronic pancreatitis and cystic fibrosis). Diseases associated with excessive secretion of insulin-antagonistic hormones can cause diabetes (which is typically resolved once the hormone excess is removed). Many drugs impair insulin secretion and some toxins damage pancreatic β-cells. The ICD-10 (1992) diagnostic entity, malnutrition-related diabetes mellitus (MRDM or MMDM, ICD-10 code E12), was deprecated by the World Health Organization when the current taxonomy was introduced in 1999.

B. Obesity

Another aspect of the present disclosure concerns new methods and compounds for the treatment and prevention of obesity. Obesity is a medical condition in which excess body fat has accumulated to the extent that it may have an adverse effect on health. It is typically defined by body mass index (BMI) and may be further evaluated in terms of fat distribution via the waist hip ratio and total cardiovascular risk factors. BMI is related to both percentage body fat and total body fat.

BMI is calculated by dividing the subject's mass by the square of his or her height (in metric units: kilograms/meters$^2$). The definitions established by the World Health Organization (WHO) in 1997 and published in 2000 are listed below:

| BMI | Classification |
|---|---|
| <18.5 | underweight |
| 18.5-24.9 | normal weight |
| 25.0-29.9 | overweight |
| 30.0-34.9 | class I obesity |
| 35.0-39.9 | class II obesity |
| ≥40.0 | class III obesity |

Obesity increases the risk of many physical and mental conditions. These comorbidities are most commonly shown in metabolic syndrome, a combination of medical disorders which includes: diabetes mellitus type 2, high blood pressure, high blood cholesterol, and high triglyceride levels.

A substantial body of research supports an association between obesity and a chronic, "smoldering" inflammatory state. Obesity is associated with overproduction of inflammatory cytokines and chronic activation of inflammatory signaling pathways, including the NF-kB pathway (Hotamisligil, 2006). Chronic inflammation in adipose tissue is linked with the development of insulin resistance in skeletal muscle (Guilherme et al., 2008). Chronic activation of the NF-κB pathway has been shown to induce insulin resistance and NF-κB inhibition has been proposed as a therapeutic strategy for the treatment of Type 2 diabetes (Arkan et al., 2005; Shoelson et al., 2006).

In a fashion analogous to the development of insulin resistance, obesity has been associated with the development of resistance to the action of leptin. Leptin, a peptide hormone, has complex biological effects but one important site of action is the mediobasal hypothalamus. This structure of the brain is known to exert control over feeding behavior and energy homeostasis. Recently, oxidative stress and activation of the NF-κB pathway in the hypothalamus were shown to be linked to hypothalamic insulin and leptin resistance (Zhang et al., 2008). Activation of the antioxidant transcription factor Nrf2 is known to inhibit NF-κB activity, and Nrf2 activation by a semisynthetic triterpenoid has been reported to inhibit the development of obesity in mice fed on a high-fat diet (Shin et al., 2009).

C. Muscular Dystrophies

Muscular dystrophy (MD) is a group of muscle diseases that results in increasing weakening and breakdown of skeletal muscles over time. The disorders differ in which muscles are primarily affected, the degree of weakness, how fast they worsen, and when symptoms begin. Many people will eventually become unable to walk. Some types are also associated with problems in other organs.

There are nine main categories of muscular dystrophy that contain more than thirty specific types. The most common type is Duchenne muscular dystrophy (DMD) which typically affects males beginning around the age of four. Other types include Becker muscular dystrophy, facioscapulohumeral muscular dystrophy, and myotonic dystrophy. They are due to mutations in genes that are involved in making muscle proteins. This can occur due to either inheriting the defect from one's parents or the mutation occurring during early development. Disorders may be X-linked recessive, autosomal recessive, or autosomal dominant. Diagnosis often involves blood tests and genetic testing.

Duchenne muscular dystrophy (DMD) is a recessive X-linked form of muscular dystrophy, affecting around 1 in 5000 boys, which results in muscle degeneration and premature death. The disorder is caused by a mutation in the gene dystrophin, located on the human X chromosome, which codes for the protein dystrophin. Dystrophin is an important component within muscle tissue that provides structural stability to the dystroglycan complex (DGC) of the cell membrane. While both sexes can carry the mutation, females are rarely affected with the skeletal muscle form of the disease.

Mutations vary in nature and frequency. Large genetic deletions are found in about 60-70% of cases, large duplications are found in about 10% of cases, and point mutants or other small changes account for about 15-30% of cases. Bladen et al. (2015), who examined some 7000 mutations, catalogued a total of 5,682 large mutations (80% of total mutations), of which 4,894 (86%) were deletions (1 exon or larger) and 784 (14%) were duplications (1 exon or larger). There were 1,445 small mutations (smaller than 1 exon, 20% of all mutations), of which 358 (25%) were small deletions and 132 (9%) small insertions, while 199 (14%) affected the splice sites. Point mutations totaled 756 (52% of small mutations) with 726 (50%) nonsense mutations and 30 (2%) missense mutations. Finally, 22 (0.3%) mid-intronic mutations were observed. In addition, mutations were identified within the database that would potentially benefit from novel genetic therapies for DMD including stop codon read-through therapies (10% of total mutations) and exon skipping therapy (80% of deletions and 55% of total mutations).

Symptoms usually appear in boys between the ages of 2 and 3 and may be visible in early infancy. Even though symptoms do not appear until early infancy, laboratory testing can identify children who carry the active mutation at birth. Progressive proximal muscle weakness of the legs and pelvis associated with loss of muscle mass is observed first. Eventually this weakness spreads to the arms, neck, and other areas. Early signs may include pseudohypertrophy (enlargement of calf and deltoid muscles), low endurance, and difficulties in standing unaided or inability to ascend staircases. As the condition progresses, muscle tissue experiences wasting and is eventually replaced by fat and fibrotic tissue (fibrosis). By age 10, braces may be required to aid in walking but most patients are wheelchair dependent by age 12. Later symptoms may include abnormal bone development that lead to skeletal deformities, including curvature of the spine. Due to progressive deterioration of muscle, loss of movement occurs, eventually leading to paralysis. Intellectual impairment may or may not be present but if present, does not progressively worsen as the child ages. The average life expectancy for males afflicted with DMD is around 25.

The main symptom of Duchenne muscular dystrophy, a progressive neuromuscular disorder, is muscle weakness associated with muscle wasting with the voluntary muscles being first affected, especially those of the hips, pelvic area, thighs, shoulders, and calves. Muscle weakness also occurs later, in the arms, neck, and other areas. Calves are often enlarged. Symptoms usually appear before age 6 and may appear in early infancy. Other physical symptoms are:

Awkward manner of walking, stepping, or running (patients tend to walk on their forefeet, because of an increased calf muscle tone. Also, toe walking is a compensatory adaptation to knee extensor weakness.)

Frequent falls

Fatigue

Difficulty with motor skills (running, hopping, jumping)

Lumbar hyperlordosis, possibly leading to shortening of the hip-flexor muscles. This has an effect on overall posture and a manner of walking, stepping, or running.

Muscle contractures of Achilles tendon and hamstrings impair functionality because the muscle fibers shorten and fibrose in connective tissue Progressive difficulty walking Muscle fiber deformities Pseudohypertrophy (enlarging) of tongue and calf muscles. The muscle tissue is eventually replaced by fat and connective tissue, hence the term pseudohypertrophy.

Higher risk of neurobehavioral disorders (e.g., ADHD), learning disorders (dyslexia), and non-progressive weaknesses in specific cognitive skills (in particular short-term verbal memory), which are believed to be the result of absent or dysfunctional dystrophin in the brain.

Eventual loss of ability to walk (usually by the age of 12)

Skeletal deformities (including scoliosis in some cases)

Trouble getting up from lying or sitting position

The condition can often be observed clinically from the moment the patient takes his first steps, and the ability to walk usually completely disintegrates between the time the boy is 9 to 12 years of age. Most men affected with DMD become essentially "paralyzed from the neck down" by the age of 21. Muscle wasting begins in the legs and pelvis, then progresses to the muscles of the shoulders and neck, followed by loss of arm muscles and respiratory muscles. Calf muscle enlargement (pseudohypertrophy) is quite obvious. Cardiomyopathy particularly (dilated cardiomyopathy) is common, but the development of congestive heart failure or arrhythmia (irregular heartbeat) is only occasional.

A positive Gowers' sign reflects the more severe impairment of the lower extremities muscles. The child helps himself to get up with upper extremities: first by rising to stand on his arms and knees, and then "walking" his hands up his legs to stand upright. Affected children usually tire more easily and have less overall strength than their peers. Creatine kinase (CPK-MM) levels in the bloodstream are extremely high. An electromyography (EMG) shows that weakness is caused by destruction of muscle tissue rather than by damage to nerves. Genetic testing can reveal genetic errors in the Xp21 gene. A muscle biopsy (immunohistochemistry or immunoblotting) or genetic test (blood test) confirms the absence of dystrophin, although improvements in genetic testing often make this unnecessary.

Abnormal heart muscle (cardiomyopathy)

Congestive heart failure or irregular heart rhythm (arrhythmia)

Deformities of the chest and back (scoliosis)

Enlarged muscles of the calves, buttocks, and shoulders (around age 4 or 5). These muscles are eventually replaced by fat and connective tissue (pseudohypertrophy).

Loss of muscle mass (atrophy)

Muscle contractures in the heels, legs

Muscle deformities

Respiratory disorders, including pneumonia and swallowing with food or fluid passing into the lungs (in late stages of the disease)

Duchenne muscular dystrophy (DMD) is caused by a mutation of the dystrophin gene at locus Xp21, located on the short arm of the X chromosome. Dystrophin is responsible for connecting the cytoskeleton of each muscle fiber to the underlying basal lamina (extracellular matrix), through a protein complex containing many subunits. The absence of dystrophin permits excess calcium to penetrate the sarcolemma (the cell membrane). Alterations in calcium and signaling pathways cause water to enter into the mitochondria, which then burst.

In skeletal muscle dystrophy, mitochondrial dysfunction gives rise to an amplification of stress-induced cytosolic calcium signals and an amplification of stress-induced reactive-oxygen species (ROS) production. In a complex cascading process that involves several pathways and is not clearly understood, increased oxidative stress within the cell damages the sarcolemma and eventually results in the death of the cell. Muscle fibers undergo necrosis and are ultimately replaced with adipose and connective tissue.

DMD is inherited in an X-linked recessive pattern. Females will typically be carriers for the disease while males will be affected. Typically, a female carrier will be unaware they carry a mutation until they have an affected son. The son of a carrier mother has a 50% chance of inheriting the defective gene from his mother. The daughter of a carrier mother has a 50% chance of being a carrier and a 50% chance of having two normal copies of the gene. In all cases, an unaffected father will either pass a normal Y to his son or a normal X to his daughter. Female carriers of an X-linked recessive condition, such as DMD, can show symptoms depending on their pattern of X-inactivation.

Duchenne muscular dystrophy has an incidence of 1 in 5000 male infants. Mutations within the dystrophin gene can either be inherited or occur spontaneously during germline transmission.

Genetic counseling is advised for people with a family history of the disorder. Duchenne muscular dystrophy can be detected with about 95% accuracy by genetic studies performed during pregnancy. Muscle biopsies may also be used.

There is no current cure for DMD, and an ongoing medical need has been recognized by regulatory authorities. Phase 1-2a trials with exon skipping treatment for certain mutations have halted decline and produced small clinical improvements in walking. Treatment is generally aimed at controlling the onset of symptoms to maximize the quality of life, and include the following:

Corticosteroids such as prednisolone and deflazacort increase energy and strength and defer severity of some symptoms.

Randomised control trials have shown that beta-2-agonists increase muscle strength but do not modify disease progression. Follow-up time for most RCTs on beta2-agonists is only around 12 months and hence results cannot be extrapolated beyond that time frame.

Mild, non jarring physical activity such as swimming is encouraged. Inactivity (such as bed rest) can worsen the muscle disease.

Physical therapy is helpful to maintain muscle strength, flexibility, and function.

Orthopedic appliances (such as braces and wheelchairs) may improve mobility and the ability for self-care. Form-fitting removable leg braces that hold the ankle in place during sleep can defer the onset of contractures.

Appropriate respiratory support as the disease progresses is important.

Comprehensive multi-disciplinary care standards/guidelines for DMD have been developed by the Centers for Disease Control and Prevention (CDC), and were published in two parts in The Lancet Neurology in 2010. To download the two articles in PDF format, go to the TREAT-NMD website.

D. Non-Alcoholic Fatty Liver Disease

Non-alcoholic fatty liver disease (NAFLD) is one of the types of fatty liver which occurs when fat is deposited (steatosis) in the liver due to causes other than excessive alcohol use. Non-alcoholic steatohepatitis (NASH) is the most extreme form of NAFLD. NAFLD is the most common liver disorder in developed countries.

NAFLD is related to insulin resistance and the metabolic syndrome and may respond to treatments originally developed for other insulin-resistant states (e.g., diabetes mellitus type 2) such as weight loss, metformin, and thiazolidinediones. Up to 80% of obese people have the disease. NASH is regarded as a major cause of cirrhosis of the liver of unknown cause. Most people have a good outcome if the condition is caught in its early stages.

About 12 to 25% of people in the United States has NAFLD. While NASH affects between 2 and 5% of people in the United States.

Most people with NAFLD have few or no symptoms. Patients may complain of fatigue, malaise, and dull right-upper-quadrant abdominal discomfort. Mild jaundice may be noticed although this is rare. More commonly NAFLD is diagnosed following abnormal liver function tests during routine blood tests. By definition, alcohol consumption of over 20 g/day (about 25 ml/day of net ethanol) excludes the condition.

NAFLD is associated with insulin resistance and metabolic syndrome (obesity, combined hyperlipidemia, diabetes mellitus (type II), and high blood pressure). Soft drinks have been linked to NAFLD due to high concentrations of fructose, which may be present either in high-fructose corn syrup or, in similar quantities, as a metabolite of sucrose. The quantity of fructose delivered by soft drinks may cause increased deposition of fat in the abdomen.

Native American men have a high prevalence of non-alcoholic fatty liver disease. Two genetic mutations for this susceptibility have been identified, and these mutations provided clues to the mechanism of NASH and related diseases.

Polymorphisms (genetic variations) in the single-nucleotide polymorphisms (SNPs) T455C and C482T in APOC3 are associated with fatty liver disease, insulin resistance, and possibly hypertriglyceridemia. 95 healthy Asian Indian men and 163 healthy non-Asian Indian men around New Haven, Conn. were genotyped for polymorphisms in those SNPs. 20% homogeneous wild both loci. Carriers of T-455C, C-482T, or both (not additive) had a 30% increase in fasting plasma apolipoprotein C3, 60% increase in fasting plasma triglyceride and retinal fatty acid ester, and 46% reduction in plasma triglyceride clearance. Prevalence of non-alcoholic fatty liver disease was 38% in carriers, 0% wild (normal). Subjects with fatty liver disease had marked insulin resistance.

NAFLD can also be caused by some medications (drug-induced illness), such as Amiodarone, Antiviral drugs (nucleoside analogues), Aspirin rarely as part of Reye's syndrome in children, Corticosteroids, Methotrexate, Tamoxifen and Tetracycline.

NAFLD is considered to cover a spectrum of disease activity. This spectrum begins as fatty accumulation in the liver (hepatic steatosis). A liver can remain fatty without disturbing liver function, but by varying mechanisms and possible insults to the liver may also progress to become non-alcoholic steatohepatitis (NASH), a state in which steatosis is combined with inflammation and fibrosis (steatohepatitis). NASH is a progressive disease: over a 10-year period, up to 20% of patients with NASH will develop cirrhosis of the liver, and 10% will suffer death related to liver disease. Cigarette smoking is not associated with an increased risk of developing NASH.

The exact cause of NAFLD is still unknown. However, both obesity and insulin resistance probably play a strong role in the disease process. The exact reasons and mechanisms by which the disease progresses from one stage to the next are not known. One debated mechanism proposes a "second hit", or further injury, enough to cause change that leads from hepatic steatosis to hepatic inflammation. Oxidative stress, hormonal imbalances, and mitochondrial abnormalities are potential causes for this "second hit" phenomenon.

Common findings are elevated liver enzymes and a liver ultrasound showing steatosis. An ultrasound may also be used to exclude gallstone problems (cholelithiasis). A liver biopsy (tissue examination) is the only test widely accepted as definitively distinguishing NASH from other forms of liver disease and can be used to assess the severity of the inflammation and resultant fibrosis.

Non-invasive diagnostic tests have been developed, such as FibroTest, that estimates liver fibrosis, and SteatoTest, that estimates steatosis, however their use has not been widely adopted. Apoptosis has been indicated as a potential mechanism of hepatocyte injury as caspase-cleaved cytokeratin 18 (M30-Apoptosense ELISA) in serum/plasma is often elevated in patients with NASH and tests based on these parameters have been developed; however, as the role of oncotic necrosis has yet to be examined it is unknown to what degree apoptosis acts as the predominant form of injury.

It has been suggested that in cases involving overweight patients whose blood tests do not improve on losing weight and exercising that a further search of other underlying causes is undertaken. This would also apply to those with fatty liver who are very young or not overweight or insulin-resistant. In addition those whose physical appearance indicates the possibility of a congenital syndrome, have a family history of liver disease, have abnormalities in other organs, and those that present with moderate to advanced fibrosis or cirrhosis.

No pharmacological treatment has received approval as of 2015. Some studies suggest diet, exercise, and antiglycemic drugs may alter the course of the disease. General recommendations include improving metabolic risk factors and reducing alcohol intake. While many treatments appear to improve biochemical markers such as alanine transaminase levels, most have not been shown to reverse histological abnormalities or reduce clinical endpoints. Bariatric surgery may also be effective.

Insulin sensitizers (metformin and thiazolidinediones) are commonly used for insulin resistance in those with NAFLD. Improvements in liver biochemistry and histology in patients with NAFLD through treatment with statins have been observed in numerous cases, although these studies were carried out on a relatively small sample of patients. Statins have also been recommended for use in treating dyslipidemia for patients with NAFLD. Treatment with pentoxifylline has demonstrated improvements in the histological appearance of fatty liver tissue under the microscope in many small trials.

The percentage of people with non-alcoholic fatty liver disease ranges from 9 to 36.9% in different parts of the world. Approximately 20% of the United States population have non-alcoholic fatty liver, and the number of people affected is increasing. This means about 75 to 100 million people in the United States are affected. The rates of non-alcoholic fatty liver disease is higher in Hispanics, which can be attributed to high rates of obesity and type 2 diabetes in Hispanic populations. Non-alcoholic fatty liver disease is also more common among men than women in all age groups until age 60, where the prevalence between sex equalize. This is due to the protective nature of estrogen. Fatty liver and NASH occur all ages, with the highest rates in the 40- to 49-year-old age group. It is the most common liver abnormality in children ages 2 to 19.

III. NEUROLOGICAL DISORDERS

The term "neurodegenerative disease or disorder" and "neurological disorders" encompass a disease or disorder in which the peripheral nervous system or the central nervous system is principally involved. The compounds, compositions, and methods provided herein may be used in the treatment of neurological or neurodegenerative diseases and disorders. As used herein, the terms "neurodegenerative disease", "neurodegenerative disorder", "neurological disease", and "neurological disorder" are used interchangeably.

Examples of neurological disorders or diseases include, but are not limited to chronic neurological diseases such as diabetic peripheral neuropathy (including third nerve palsy, mononeuropathy, mononeuropathy multiplex, diabetic amyotrophy, autonomic neuropathy and thoracoabdominal neuropathy), Alzheimer's disease, age-related memory loss, senility, age-related dementia, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis ("MS"), synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoffs related dementia (alcohol induced dementia), Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia). Other conditions also included within the methods of the present invention include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica, and frontal lobe dementia. Also other neurodegenerative disorders resulting from cerebral ischemia or infarction including embolic occlusion and thrombotic occlusion as well as intracranial hemorrhage of any type (including, but not limited to, epidural, subdural, subarachnoid, and intracerebral), and intracranial and intravertebral lesions (including, but not limited to, contusion, penetration, shear, compression, and laceration). Thus, the term also encompasses acute neurodegenerative disorders such as those involving stroke, traumatic brain injury, schizophrenia, peripheral nerve damage, hypoglycemia, spinal cord injury, epilepsy, and anoxia and hypoxia.

In some embodiments, the neurodegenerative disorder is amyloidosis. Amyloidosis is observed in Alzheimer's Disease, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis. In preferred embodiments, the neurodegenerative disorder treated and/or prevented using the methods and compositions of the disclosure is Alzheimer's disease.

IV. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the compounds described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 mL of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate regulatory agencies for the safety of pharmaceutical agents.

B. Methods of Treatment

In particular, the compositions that may be used in treating a metabolic condition in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., slowing, stopping, reducing or eliminating one or more symptoms or underlying causes of disease). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms and other drugs being administered concurrently. In some embodiments, amount of the compounds used is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the compounds may be more efficacious and thus a smaller dose is required to achieve a similar effect. Such a dose is typically administered once a day for a few weeks or until sufficient achieve clinical benefit.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, family history, and the like).

C. Combination Therapies

It is envisioned that the compounds described herein may be used in combination therapies with one or more additional therapies or a compound which mitigates one or more of the side effects experienced by the patient. It is common in the field of medicine to combine therapeutic modalities. The following is a general discussion of therapies that may be used in conjunction with the therapies of the present disclosure.

To treat diseases or disorders using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the compounds described herein may precede or follow the other treatment by intervals ranging from minutes to weeks. One would generally ensure that a significant period of time did not expire between the times of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| | | | | | | |
|---|---|---|---|---|---|---|
| A/B/A | B/A/B | B/B/A | A/A/B | B/A/A | A/B/B | B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are also contemplated. A discussion of other potential therapies that may be used combination with the compounds of the present disclosure is presented elsewhere in this document.

V. CHEMISTRY BACKGROUND

In some aspects, the compounds of this disclosure can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein. The synthetic method described herein may be used to produce preparative scale amounts of the compounds described herein.

B. Chemical Definitions

When used in the context of a chemical group: "hydrogen" means H; "hydroxy" means —OH; "oxo" means =O; "carbonyl" means —C(=O)—; "carboxy" means —C(=O) OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; "hydrazine" means —NHNH$_2$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "hydroxysulfonyl" means —SO$_3$H, "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⹀" represents a single bond or a double bond. Thus, the formula

covers, for example,

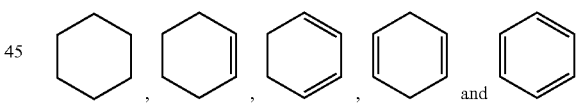

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ⌇ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂" means a single bond where the group attached to the thick end of the wedge is "out of the page." The symbol "⦀" means a single bond where the group attached to the thick end of the wedge is "into the page". The symbol " ∼ " means a single bond where the geometry around a double bond [e.g., either (E) or (Z)] is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula

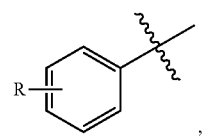

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula

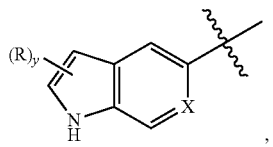

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "Cn" defines the maximum number (n) of carbon atoms that can be in the group/class, with the minimum number as small as possible for the group/class in question, e.g., it is understood that the minimum number of carbon atoms in the group "alkenyl$_{(C \leq 8)}$" or the class "alkene$_{(C \leq 8)}$" is two. Compare with "alkoxy$_{(C \leq 10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula HR, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The following groups are non-limiting examples of substituted alkyl groups: CH₂OH, —CH₂Cl, —CF₃, —CH₂CN, CH₂C(O)OH, —CH₂C(O)OCH₃, —CH₂C(O)NH₂, —CH₂C(O)CH₃, —CH₂OCH₃, —CH₂OC(O)CH₃, CH₂NH₂, —CH₂N(CH₃)₂, and CH₂CH₂Cl. The term "haloalkyl" is a subset of substituted alkyl, in which the hydrogen atom replacement is limited to halo (i.e., —F, —Cl, —Br, or I) such that no other atoms aside from carbon, hydrogen and halogen are present. The group, —CH₂Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH₂F, —CF₃, and —CH₂CF₃ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH₂)₂ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

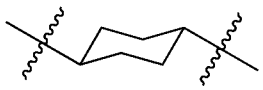 [SMILES: *C1CCC(*)CC1]

is a non-limiting example of cycloalkanediyl group. A "cycloalkane" refers to the class of compounds having the formula HR, wherein R is cycloalkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂,—C(O)NH₂, —C(O)NHCH₃, —C(O)N(CH₃)₂, —OC(O)CH₃, —NHC(O)CH₃, —S(O)₂OH, or —S(O)₂NH₂.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH₂ (vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH₃)CH₂—, —CH=CHCH₂—, and —CH₂CH=CHCH₂— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula HR, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups CH=CHF, —CH=CHCl and CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH₃, and —CH₂C≡CCH₃ are non-limiting examples of alkynyl groups. An "alkyne" refers to the class of compounds having the formula HR, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aryl" when used without the "substituted" modifier refers to a monovalent unsaturated aromatic group with an aromatic carbon atom as the point of attachment, said carbon atom forming part of a one or more aromatic ring structure, wherein the ring atoms are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl or fused or unfused cycloalkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term arenediyl does not preclude the presence of one or more alkyl or fused or unfused cycloalkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include

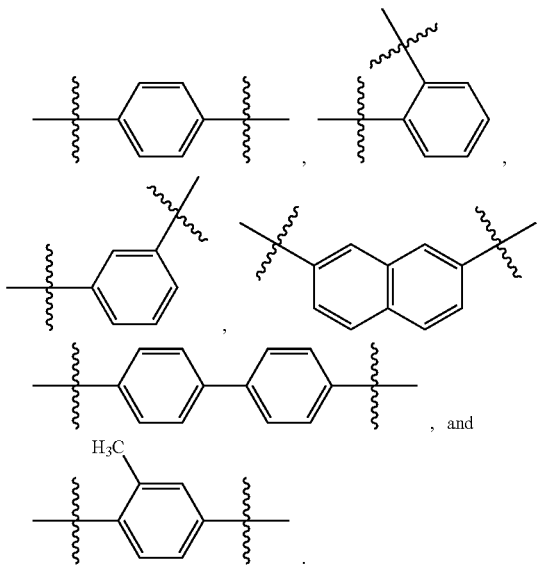

, and

An "arene" refers to the class of compounds having the formula HR, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group alkanediylaryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, the aromatic ring structures being one, two, three, or four ring structures each containing from three to nine ring atoms, and wherein the heteroaryl group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroaryl does not preclude the presence of one or more alkyl or aryl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroarenediyl does not preclude the presence of one or more alkyl or aryl groups (carbon number limitation permitting) attached to the aromatic ring or aromatic ring system. Non-limiting examples of heteroarenediyl groups include

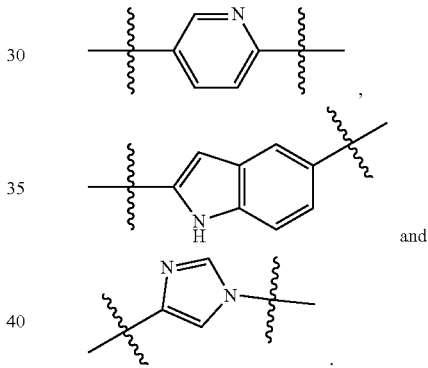

and

The term "N-heteroaryl" refers to a heteroaryl group with a nitrogen atom as the point of attachment. A "heteroarene" refers to the class of compounds having the formula HR, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heteroaralkyl" when used without the "substituted" modifier refers to the monovalent group alkanediylheteroaryl, in which the terms alkanediyl and heteroaryl are each used in a manner consistent with the definitions provided above. Non-limiting examples are: pyridinylmethyl and 2-quinolyl-ethyl. When the term aralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted heteroaralkyls are: (3-hydroxypyridinylmethyl, and 2-chloro-2-quinolyl-eth-1-yl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, the non-aromatic ring structures being one, two, three, or four ring structures each containing from three to nine ring atoms, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings are connected with a covalent bond. As used herein, the term heterocycloalkanediyl does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include

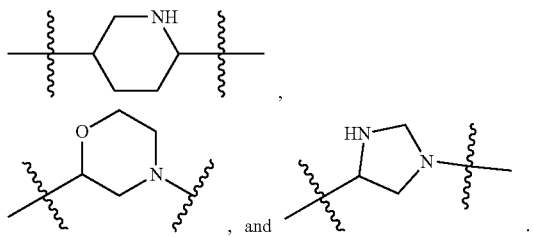

, and

The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

An "amino protecting group" is well understood in the art. An amino protecting group is a group which prevents the reactivity of the amine group during a reaction which modifies some other portion of the molecule and can be easily removed to generate the desired amine. Amino protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxy acetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxy carbonyl, 3,4,5-trimethoxybenzyloxycarbonyl, 1-(p-biphenylyl)-1-methylethoxy carbonyl, α,α-dimethyl-3,5-dimethoxy benzyloxy carbonyl, benzhydryloxycarbonyl, t-butyloxy carbonyl (Boc), diisopropylmethoxycarbonyl, isopropyloxy carbonyl, ethoxy carbonyl, methoxycarbonyl, allyloxy carbonyl (Alloc), 2,2,2-trichloroethoxycarbonyl, 2-trimethyl-silylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyl-oxycarbonyl, phenylthiocarbonyl and the like; aralkyl groups such as benzyl, triphenylmethyl, benzyloxymethyl and the like; and silyl groups such as trimethylsilyl and the like. Additionally, the "amino protecting group" can be a divalent protecting group such that both hydrogen atoms on a primary amine are replaced with a single protecting group. In such a situation the amino protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula PG$_{MA}$NH— or PG$_{DA}$N— wherein PG$_{MA}$ is a monovalent amine protecting group, which may also be described as a "monovalently protected amino group" and PG$_{DA}$ is a divalent amine protecting group as described above, which may also be described as a "divalently protected amino group".

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedrally substituted carbon centers), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its (R) form, (S) form, or as a mixture of the (R) and (S) forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

The inventors have developed a series of potent ERR ligands utilizing a structure-based drug design approach. Starting from a reported co-crystal structure of the ERRγ ligand binding domain with the agonist, GSK4716, they developed a docking model and designed a series of di-substituted heteroaromatic compounds. Once these compounds were prepared they were screened in a ERRγ thermal shift assay to determine if they bound directly to the receptor and altered its thermal stability. Compounds that dose-dependently affected the melting point of ERRγ to a greater or comparable degree than the standards were evaluated in a cell based assay of ERRγ activity. Using a Gal4-ERRγ ligand binding domain chimera cotransfection cell-based assay the activity of several of the hits identified in the thermal shift assay were confirmed to dose-dependently activate the transcriptional activity of ERRγ (FIG. 1).

Example 2

A. General Synthetic Procedure

Compounds of the present invention can be prepared following the general procedure outlined below. Starting from the appropriate bromo substituted heterocycle such as I with either an ester or acid moiety present synthesis of the compounds can proceed in either one of two ways. If R is an ester, then saponification followed by coupling of the resulting acid with a suitable amine using standard peptide coupling reagents, such as TBTU lead to the amide containing heterocyclic compound of type II. Conversion of II to the desired substituted heterocycles of type IV can be achieved via a cross-coupling reaction of the bromide and the desired aryl group. A standard procedure used was Suzuki type coupling between the bromide and appropriately substituted boronic acid. This step can be done either on the ester or acid. Alternatively, in some instances, the order can be reversed and the cross-coupling reaction can occur first followed by conversion to the amide.

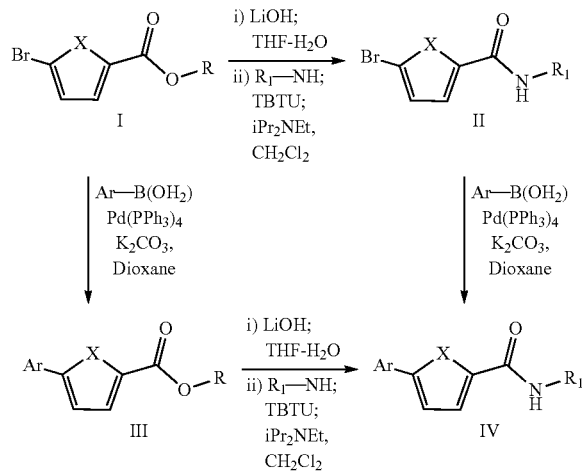

Scheme 1. General synthetic procedures for preparation of ERR analogs.

B. Experimental Details

Synthesis of 5-(3-cyanophenyl)-N-(pyridin-4-yl)thiophene-2-carboxamide (1)

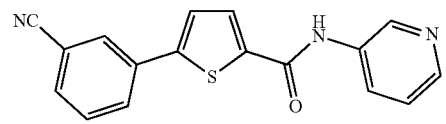

(1)

Step 1. Synthesis of 5-(3-cyanophenyl)thiophene-2-carboxylic Acid

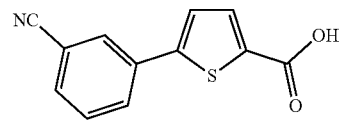 [SMILES: N#Cc1cccc(-c2ccc(C(=O)O)s2)c1]

Potassium carbonate (0.667 g, 4.830 mmol) and 3-cyanophenylboronic acid (0.3548 g, 2.415 mmol) were added to a 20 mL scintillation vial with DI water (1 mL) and absolute EtOH (8 mL). The vial was purged with argon. Next 5-bromo-2-thiophenecarboxylic acid (0.500 g, 2.415 mmol) was added, followed by Pd(PPh$_3$)$_4$ (0.100 g, 0.0865 mmol). The vial was purged with argon again then heated at reflux for 10 h. The reaction was cooled, acidified with 10% HCl, and extracted with EtOAc three times. The combined organic layers were washed with sat. aq. NaHCO$_3$ three times. The basic aqueous layer was then acidified with 10% HCl, resulting in precipitation of the product. The precipitate was removed by gravity filtration and dried overnight open to the atmosphere. Product was isolated as a tan solid in 98% yield (0.5424 g). $^1$H NMR (400 MHz, DMSO-d$_6$) δ 13.29 (broad s, 1H), 8.28 (s, 1H), 8.07 (d, J=8.0 Hz, 1H), 7.85 (d, J=7.8 Hz, 1H), 7.75 (dd, J=3.9 Hz, 5.8 Hz, 2H), 7.67 (t, J=7.8 Hz, 1H).

Step 2. Synthesis of 5-(3-cyanophenyl)-N-(pyridin-4-yl)thiophene-2-carboxamide (1)

To a solution of 5-(3-cyanophenyl)thiophene-2-carboxylic acid (0.1000 g, 0.4362 mmol) and TBTU (0.1400 g, 0.4362 mmol) in dry DMF (4.3 mL) was added DIPEA (0.190 mL, 1.0905 mmol). The reaction was stirred at room temperature for 20 min and then 4-aminopyridine (0.0492 g, 0.5234 mmol) was added. The reaction was stirred overnight at room temperature. The reaction was quenched with water to precipitate the product, compound 1. The mixture was filtered in a sintered funnel by vacuum suction. The solid was triturated with cold methanol, the solvent removed by vacuum suction, and the product dried. Product was isolated as a yellow-tan solid in 54% yield (0.0731 g). $^1$H NMR (400 MHz, DMSO-d$_6$) δ 10.61 (s, 1H), 8.50 (d, J=5.4 Hz, 2H), 8.30 (s, 1H), 8.11 (d, J=4.0 Hz, 1H), 8.08 (d, J=7.8 Hz, 2H), 7/86 (d, J=7.8 Hz, 1H), 7.83 (d, J=4.0 Hz, 1H), 7.75 (d, J=6.1 Hz, 2H), 7.68 (t, J=7.9 Hz, 1H).

Synthesis of N-benzyl-5-(4-chlorophenyl)thiophene-2-carboxamide (2)

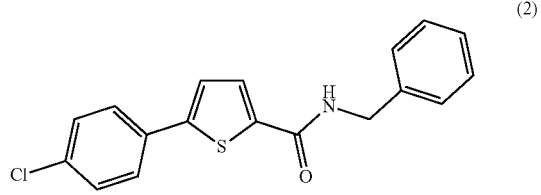 [SMILES: O=C(NCc1ccccc1)c1ccc(-c2ccc(Cl)cc2)s1]

(2)

To a solution of the commercially available 5-(4-chlorophenyl)thiophene-2-carboxylic acid (0.075 g, 0.3142 mmol) and TBTU (0.1009 g, 0.3142 mmol) in dry DMF (3.1 mL) was added DIPEA (0.014 mL, 0.7855 mmol). The reaction was stirred at room temperature for 20 min and then benzylamine (0.04 mL, 0.3770 mmol) was added. The reaction was stirred overnight at room temperature. The reaction was quenched with water and extracted with $CH_2Cl_2$. The combined organic layers were dried over anhydrous $Na_2SO_4$ and concentrated by rotary evaporation. The residue was purified by flash column chromatography (EA:Hex gradient). Product was isolated as a colorless solid in 82% yield (0.0842 g). $^1H$ NMR (400 MHz, $CDCl_3$) δ 7.46 (d, J=8.6 Hz, 2H), 7.38 (d, J=3.9 Hz, 1H), 7.32-7.27 (m, 6H), 7.27-7.21 (m, 1H), 7.16 (d, J=3.9 Hz, 1H), 6.17 (s, 1H), 4.57 (d, J=5.8 Hz, 2H).

Synthesis of N-benzyl-1-(5-(4-chlorophenyl)thiophen-2-yl)methanamine (3)

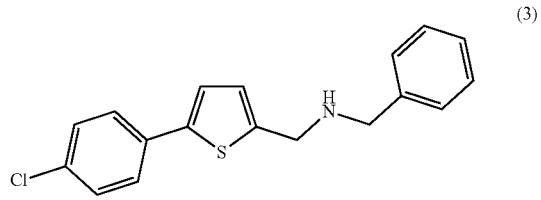 [SMILES: Clc1ccc(-c2ccc(CNCc3ccccc3)s2)cc1]

(3)

To a cooled solution of lithium aluminum hydride (0.0578 g, 1.525 mmol) in 2 mL dry THF under argon was added N-benzyl-5-(4-chlorophenyl)thiophene-2-carboxamide, 2, (0.050 g, 0.1525 mmol) from above in 1 mL dry THF. The reaction was stirred overnight, warming room temperature. The reaction was quenched by slowly pouring the reaction mixture into a mixture of water/$Na_2SO_4$. The solution was extracted with ethyl acetate, dried over $Na_2SO_4$, and concentrated by rotary evaporation. The crude material was purified by flash chromatography (30% EtOAc:Hex). Product was isolated in 39% yield (0.0190 g). $^1H$ NMR (400 MHz, $CDCl_3$) δ 7.62 (d, J=7.2 Hz, 2H), 7.42-7.36 (m, 5H), 7.32-7.26 (m, 2H), 7.19 (d, J=3.6 Hz, 1H), 6.92 (d, J=3.6 Hz, 1H); $^{13}C$ NMR (100 MHz, $CDCl_3$) δ 143.9, 143.3, 139.9, 134.6, 129.1, 128.8, 128.4, 128.2, 127.2, 127.0, 126.1, 125.8, 125.6, 122.5, 52.8, 47.8.

Synthesis of 2-(4-isopropylphenyl)-5-(phenoxymethyl)thiophene (4)

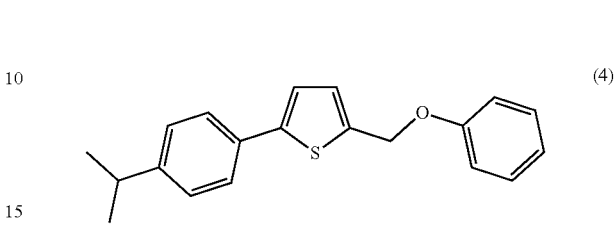

(4)

Phenol (0.0130 g, 0.1386 mmol) and triphenylphosphine (0.0727 g, 0.2772 mmol) were dissolved in 1 mL dry THF and cooled in an ice bath. An argon balloon was added and then (5-(4-isopropylphenyl)thiophen-2-yl)methanol (0.0322 g, 0.1386 mmol) was added in 0.5 mL of dry THF to the reaction vial. The reaction was stirred for 10 min then di-iso-propylazodicarboxylate (0.0561 g, 0.2772 mmol) was diluted in 1 mL dry THF and added dropwise to the reaction vial over 20 minutes. The reaction was stirred overnight, warming to room temperature. The reaction mixture was evaporated by rotary evaporation and the residue purified by flash chromatography (15% EtOAc:Hex).

Synthesis of 3-(4-hydroxyphenyl)-N-(4-isopropylphenyl)-1H-pyrazole-5-carboxamide (5)

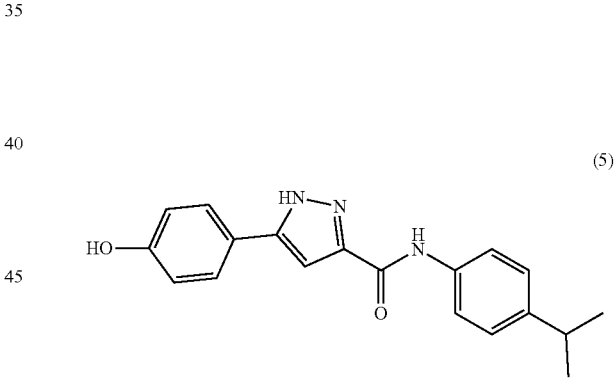

(5)

To a solution of 3-(4-hydroxyphenyl)-1H-pyrazole-5-carboxylic acid (0.100 g, 0.4898 mmol) and TBTU (0.1573 g, 0.4898 mmol) in dry DMF (4.9 mL) was added DIPEA (0.213 mL, 1.2245 mmol). The reaction was stirred at room temperature for 20 min and then 4-isopropylaniline (0.080 mL, 0.5877 mmol) was added. The reaction was stirred overnight at room temperature. The reaction was quenched with water and extracted with both dichloromethane and ethyl acetate. The combined organic layers were dried over anhydrous $Na_2SO_4$ and concentrated by rotary evaporation. The crude residue was purified by flash column chromatography (45-65% EA:Hex). Product was isolated in 48% yield (0.0754 g). $^1H$ NMR (400 MHz, DMSO-$d_6$) δ 13.51 (s, 1H), 9.90 (s, 1H), 9.76 (s, 1H), 7.72 (d, J=8.4 Hz, 2H), 7.69-7.60 (m, 3H), 7.20 (d, J=8.5 Hz, 2H), 7.00 (s, 1H), 6.86 (d, J=8.6 Hz, 2H), 2.86 (sept, J=6.9 Hz, 1H), 1.21 (d, J=6.9 Hz, 6H).

Synthesis of N-(4-hydroxyphenyl)-5-(3-isopropylphenyl)thiophene-2-carboxamide (6)

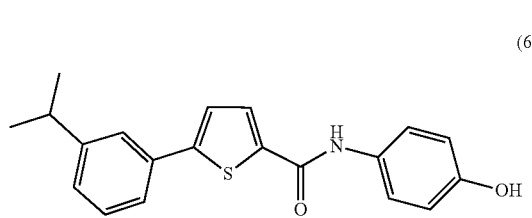

Step 1. Synthesis of 5-(3-isopropylphenyl)thiophene-2-carboxylic Acid

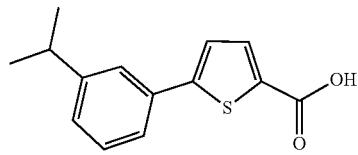 [SMILES: CC(C)c1cccc(-c2ccc(C(=O)O)s2)c1]

Potassium carbonate (0.667 g, 4.830 mmol) and (3-isopropylphenyl)boronic acid (0.3960 g, 2.415 mmol) were added to a 20 mL scintillation vial with DI water (1 mL) and absolute EtOH (8 mL). The vial was purged with argon. Next 5-bromo-2-thiophenecarboxylic acid (0.500 g, 2.415 mmol) was added, followed by Pd(PPh$_3$)$_4$ (0.139 g, 0.1207 mmol). The vial was purged with argon again then heated at reflux for 10 h. The reaction was cooled, acidified with 10% HCl, and extracted with EtOAc three times. The combined organic layers were washed with sat. aq. NaHCO$_3$ three times. The basic aqueous layer was then acidified with 10% HCl, resulting in precipitation of the product. The precipitate was removed by gravity filtration and dried overnight open to the atmosphere. Product was isolated as a pale yellow solid in 81% yield (0.4829 g). $^1$H NMR (400 MHz, DMSO-d$_6$) δ 13.08 (broad s, 1H), 7.72 (d, J=3.9 Hz, 1H), 7.60-7.57 (m, 2H), 7.54 (d, J=7.8 Hz, 1H), 7.38 (t, J=7.7 Hz, 1H), 7.29 (d, J=7.7 Hz, 1H), 2.96 (sept, J=6.9 Hz, 1H), 1.25 (d, J=6.9 Hz, 6H).

Step 2. Synthesis of N-(4-hydroxyphenyl)-5-(3-isopropylphenyl)thiophene-2-carboxamide (6)

To a solution of 5-(3-isopropylphenyl)thiophene-2-carboxylic acid (0.100 g, 0.4059 mmol) and TBTU (0.1303 g, 0.4059 mmol) in dry DMF (4.0 mL) was added DIPEA (0.176 mL, 1.0147 mmol). The reaction was stirred at room temperature for 20 min and then 4-aminophenol (0.0531 g, 0.4871 mmol) was added. The reaction was stirred overnight at room temperature. The reaction was quenched with water to precipitate the product. The mixture was filtered in a sintered funnel by vacuum suction. The solid was triturated with cold methanol, the solvent removed by vacuum suction, and the product dried. Product was isolated as a dark tan solid in 51% yield (0.0696 g). $^1$H NMR (400 MHz, DMSO-d$_6$) δ 9.96 (s, 1H), 9.22 (s, 1H), 7.89 (d, J=4.0 Hz, 1H), 7.46-7.44 (m, 2H), 7.47 (d, J=7.8 Hz, 1H), 0.42 (d, J=8.8 Hz, 2H), 7.31 (t, J=7.6 Hz, 1H), 7.20 (d, J=7.7 Hz, 1H), 6.68 (d, J=8.8 Hz, 2H), 2.89 (sept, J=6.9 Hz, 1H), 1.18 (d, J=6.9 Hz, 6H).

Synthesis of N-(3-fluorophenyl)-5-(4-hydroxyphenyl)thiophene-2-carboxamide (7)

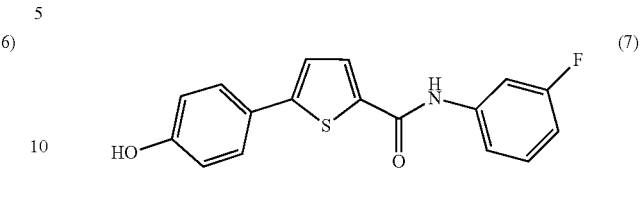

Step 1. Synthesis of 5-bromo-N-(3-fluorophenyl)thiophene-2-carboxamide

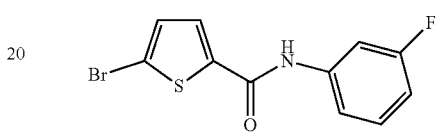

To a solution of 5-bromo-2-thiophenecarboxylic acid (0.100 g, 0.4830 mmol) and TBTU (0.1551 g, 0.4830 mmol) in dry DMF (4.8 mL) was added DIPEA (0.210 mL, 1.207 mmol). The reaction was stirred at room temperature for 20 min and then 3-fluoroaniline (0.0644 g, 0.5795 mmol) was added. The reaction was stirred overnight at room temperature. The reaction was quenched with water to precipitate the product. The mixture was filtered in a sintered funnel by vacuum suction. The solid was triturated with cold methanol, the solvent removed by vacuum suction, and the product dried. Product was isolated as a light brown solid in 36% yield (0.053 g). $^1$H NMR (400 MHz, DMSO-d$_6$) δ 10.44 (s, 1H), 7.87 (d, J=4.1 Hz, 1H), 7.67 (dt, J=11.7 Hz, 2.2 Hz, 1H), 7.49 (d, J=8.2 Hz, 1H), 7.44-7.37 (m, 2H), 6.96 (td, J=8.3 Hz, 2.5 Hz, 1H).

Step 2. Synthesis of N-(3-fluorophenyl)-5-(4-hydroxyphenyl)thiophene-2-carboxamide (7)

Potassium carbonate (0.0460 g, 0.3332 mmol) and (4-hydroxyphenyl)boronic acid (0.023 g, 0.1666 mmol) were added to a 20 mL scintillation vial with DI water (0.25 mL) and absolute EtOH (2 mL). The vial was purged with argon, then 5-bromo-2-thiophenecarboxylic acid (0.050 g, 0.1666 mmol) was added, followed by Pd(PPh$_3$)$_4$ (0.007 g, 0.0060 mmol). The vial was purged with argon again then heated at reflux for 10 h. The reaction was cooled, acidified with 10% HCl, and extracted with EtOAc three times. The combined organic layers were washed with sat. aq. NaHCO$_3$ three times. The organic layer was dried over anhydrous Na$_2$SO$_4$ and concentrated by rotary evaporation. The crude product was purified by flash chromatography (48% EtOAc:Hex). Product was isolated as a tan solid in 67% yield (0.0353 g). $^1$H NMR (400 MHz, DMSO-d$_6$) δ 10.34 (s, 1H), 9.84 (s, 1H), 7.98 (d, J=4.0 Hz, 1H), 7.71 (dt, J=11.7 Hz, 2.2 Hz, 1H), 7.58 (d, J=8.6 Hz, 2H), 7.52 (d, J=8.2 Hz, 1H), 7.44 (d, J=4.0 Hz, 1H), 7.40 (dt, J=6.9 Hz, 8.2 Hz, 1H), 6.93 (dt, J=2.0 Hz, 8.3 Hz, 1H), 6.85 (d, J=8.7 Hz, 2H); $^{13}$C NMR (100 MHz, DMSO-d$_6$) δ 160.5, 158.7, 150.2, 141.0, 137.0, 131.2, 130.8, 130.7, 127.8, 124.5, 123.0, 116.5, 116.3, 107.5, 107.2; $^{19}$F NMR (376 MHz, DMSO-d$_6$) δ −112.13; HRMS m/z calcd for (C$_{17}$H$_{12}$FN$_2$O$_2$S)Na$^+$ dimer 649.1038, found of spray dimer 649.1039.

Synthesis of (4-(5-((3-fluorophenyl)carbamoyl)thiophen-2-yl)phenyl)boronic acid (8)

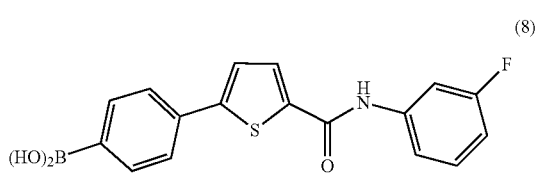 [SMILES: O=C(Nc1cccc(F)c1)c1ccc(-c2ccc(B(O)O)cc2)s1]

(8)

A mixture of 5-bromo-N-(3-fluorophenyl)thiophene-2-carboxamide (0.040 g, 0.1333 mmol) potassium carbonate (0.1842 g, 1.333 mmol), 1,4-phenylenediboronic acid (0.0663 g, 0.3998 mmol), and Pd(PPh$_3$)$_4$ (0.0031 g, 0.0027 mmol) were added to a 2 dram scintillation vial with DI water (0.66 mL) and dioxane (2.6 mL). The vial was purged with argon then heated at 80° C. for 3 h. The reaction was cooled, diluted with water, and filtered in a sintered funnel. The solid was washed with saturated aqueous NaHCO$_3$ and the solvent removed by vacuum aspiration. The crude solid was purified by flash chromatography (2% MeOH:DCM). Product was isolated as a tan solid in 28% yield (0.0128 g). $^1$H NMR (400 MHz, DMSO-d$_6$) δ 10.46 (s, 1H), 8.15 (s, 2H), 8.08 (d, J=4.0 Hz, 1H), 7.88 (d, J=8.1 Hz, 2H), 7.76-7.70 (m, 3H), 7.69 (d, J=4.0 Hz, 1H), 7.55 (d, J=8.2 Hz, 1H), 7.40 (dt, J=7.0 Hz, 8.2 Hz, 1H), 6.95 (td, J=8.4 Hz, 2.4 Hz, 1H); HRMS m/z calcd for (C$_{17}$H$_{13}$BFNO$_3$S)—H 320.0620, found 320.0621.

Synthesis of 5-(3-aminophenyl)-N-(3-fluorophenyl)thiophene-2-carboxamide (9)

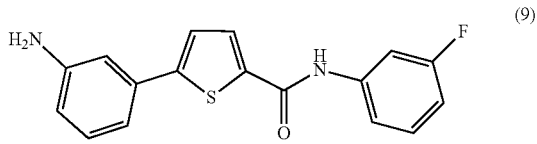 [SMILES: Nc1cccc(-c2ccc(C(=O)Nc3cccc(F)c3)s2)c1]

(9)

Potassium carbonate (0.0460 g, 0.3332 mmol) and (3-aminophenyl)boronic acid (0.0228 g, 0.1666 mmol) were added to a 2 dram scintillation vial with DI water (0.25 mL) and absolute EtOH (2 mL). The vial was purged with argon. Next 5-bromo-N-(3-fluorophenyl)thiophene-2-carboxamide (0.050 g, 0.1666 mmol) was added, followed by Pd(PPh$_3$)$_4$ (0.0069 g, 0.0060 mmol). The vial was purged with argon again then heated at reflux for 10 h. The reaction was cooled and diluted with water. The precipitate was filtered in a sintered funnel and the solid was washed with saturated aqueous NaHCO$_3$. The solvent was removed by vacuum aspiration. The crude solid was purified by flash chromatography (53% EtOAc:Hex). Product was isolated as a red semi-solid in quantitative yield. $^1$H NMR (400 MHz, DMSO-d$_6$) δ 10.38 (s, 1H), 8.00 (d, J=4.0 Hz, 1H), 7.71 (dt, J=11.8 Hz, 2.2 Hz, 1H), 7.52 (d, J=8.2 Hz, 1H), 7.47 (d, J=4.0 Hz, 1H), 7.40 (dt, J=6.9 Hz, 1H), 8.2 Hz, 1H), 7.10 (t, J=7.8 Hz, 1H), 6.98-6.86 (m, 3H), 6.59 (dd, J=1.3 Hz, 8.0 Hz, 1H), 5.29 (s, 2H); HRMS m/z calcd for (C$_{17}$H$_{13}$FN$_2$OS)H$^+$ 313.0805, found 313.0804.

Synthesis of N-(4-hydroxyphenyl)-2-(thiophen-3-yl)oxazole-4-carboxamide (10)

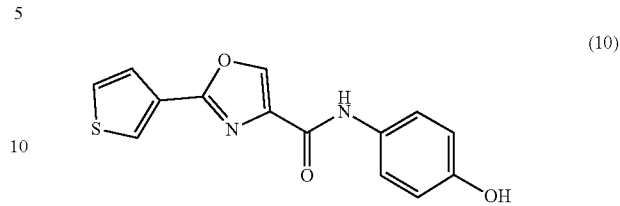

(10)

Step 1. Synthesis of ethyl 2-(thiophen-3-yl)oxazole-4-carboxylate

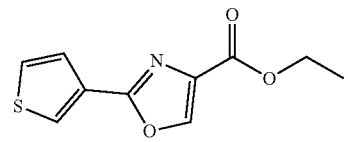

To a degassed solution of the oxazole (0.175 g, 1 mmol), boronic acid (0.134 g, 1.05 mmol) and potassium carbonate (0.278 g, 2 mmol) in dimethoxyethane (4 mL) was added Pd(PPH$_3$)$_4$ (0.058 g, 0.005 mmol). The resulting mixture was heated to 90° C. for 12 h. The reaction was then cooled to rt and the reaction mixture was diluted with ethyl acetate and filtered through a pad of celite. The celite was washed with additional ethyl acetate. The resulting organics were combined, dried over sodium sulfate and concentrated under vacuum. The crude product was then purified by flash chromatography (1:1 to 1:2 Hex:EtOAc). Product was isolated a pink solid in 32% yield (0.075 mg). LC-MS m/z calcd for (C$_{10}$H$_9$NO$_3$S)H$^+$ 224.2, found 224.2.

Step 2. Synthesis of 2-(thiophen-3-yl)oxazole-4-carboxylic Acid

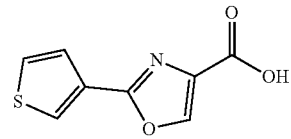 [SMILES: O=C(O)c1coc(-c2ccsc2)n1]

To a solution of the above ester (0.075 g, 0.336 mmol) in THF (1.5 mL) was added 1.0N LiOH—H$_2$O (0.5 mL). The resulting solution was stirred at rt for 1 h after which the reaction was judged complete by HPLC. The reaction was acidified by addition of 1.0N HCl and the product was extracted with EtOAc (3×). The combined organics were dried over sodium sulfate and concentrated in vacuo. The resulting product was isolated as an off-white solid (0.061 g) with sufficient purity to use as is in the next step. LC-MS m/z calcd for (C$_8$H$_5$NO$_3$S)H$^+$ 196.05, found 196.1

Step 3. N-(4-hydroxyphenyl)-2-(thiophen-3-yl)oxazole-4-carboxamide (10)

To a solution of the above acid (0.030 g, 0.154 mmol) and N,N-diisopropylethylamine (0.069 mL, 0.385 mmol) in DMF (2 mL) was added TBTU (0.053 g, 0.161 mmol) and the resulting mixture was stirred at rt for 30 min. To this mixture was then added 4-aminophenol (0.020 g, 0.185 mmol) and the reaction was allowed to stir at rt overnight. The reaction was quenched by addition of water which resulted in a precipitate which was washed with water and dried. Product was isolated as a tan solid in 68% yield (0.030 g). $^1$H NMR (400 MHz, DMSO-$d_6$) δ 9.87 (s, 1H), 9.29 (s, 1H), 8.74 (s, 1H), 8.31-8.30 (m, 1H), 7.80-7.78 (m, 1H), 7.68-7.66 (m, 1H), 7.50 (d, J=8.8 Hz, 2H), 6.73 (d, J=8.8 Hz, 2H); LC-MS m/z calcd for ($C_{14}H_{10}N_2O_3S$)H$^+$ 287.1, found 287.0

Synthesis of N-(3-fluorophenyl)-5-(4-hydroxyphenyl)thiazole-2-carboxamide (11)

(11)

Step 1: Synthesis of 5-bromo-N-(3-fluorophenyl)thiazole-2-carboxamide

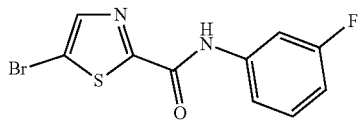 [SMILES: O=C(Nc1cccc(F)c1)c1ncc(Br)s1]

To a solution of lithium 4-bromothiazole-2-carboxylate (0.214 g, 1.0 mmol) and 3-fluoroaniline (0.122 g, 1.1 mmol) in DMF (5 ml), which had been cooled to 0° C., was slowly added HATU (0.399 g, 1.05 mmol). The reaction was maintained at 0° C. for 2 h and then allowed to slowly warm to rt overnight. Water was added to the reaction and precipitate formed. The reaction was allowed to stir for an additional 30 min and then filtered through a fritted funnel. The product was collected and dried to give a cream colored solid in 93% yield (0.278 g). $^1$H NMR (400 MHz, DMSO-$d_6$) δ 11.04 (s, 1H), 8.24 (s, 1H), 7.75 (d, J=11.2 Hz, 1H), 7.46 (d, J=8.4 Hz, 1H), 7.41 (q, J=8.0 Hz, 1H), 6.96 (t, J=4.8 Hz, 1H); LC-MS m/z calcd for ($C_{10}H_6BrFN_2OS$)H$^+$ 301.0 & 303.0, found 300.9 & 302.9.

Step 2: Synthesis of N-(3-fluorophenyl)-5-(4-(methoxymethoxy)phenyl)thiazole-2-carboxamide

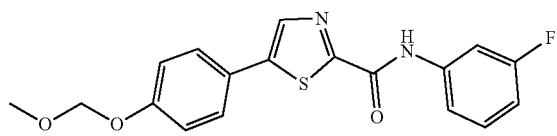 [SMILES: COCOc1ccc(-c2cnc(C(=O)Nc3cccc(F)c3)s2)cc1]

A mixture of (4-(methoxymethoxy)phenyl)boronic acid (0.044 g, 0.24 mmol), the bromide from above (0.060 g, 0.2 mmol) and potassium carbonate (0.055 g, 0.4 mmol) in DME (2 mL) was purged of air and back filled with argon. To this mixture was added PdCl$_2$(PPh$_3$)$_2$ (0.007 g, 0.01 mmol) and then heated to 80° C. overnight. The reaction was then diluted with CH$_2$Cl$_2$ and filtered through a pad of celite with additional washing with methanol and water. The layers were separated and the aqueous layer was washed with additional CH$_2$Cl$_2$. The organics were combined, dried with sodium sulfate and concentrated in vacuo. The crude material was purified using flash chromatography (100:0 to 1:1; Hex:EtOAc). Product was isolated as a pale-yellow solid in 71% yield (0.051 g). LC-MS m/z calcd for ($C_{18}H_{15}FN_2O_3S$) H$^+$ 359.1, found 359.1

Step 3. Synthesis of Preparation of N-(3-fluorophenyl)-5-(4-hydroxyphenyl)thiazole-2-carboxamide (11)

To a solution of the above mom-ether compound (0.051 g, 0.142 mmol) in CH$_2$Cl$_2$ (1 mL), cooled to 0° C., was added trifluoroacetic acid (0.016 mL, 0.213 mmol). The reaction was allowed gradually allowed to warm to rt and stir overnight. When the reaction was judged to be complete water was added and the layers were separated. The aqueous layer was extracted with CH$_2$Cl$_2$ (3×). The organics were combined, dried over sodium sulfate and concentrated in vacuo. The resulting crude product was purified on flash chromatography (100:0 to 1:1; Hex:EtOAc). Product was isolated as a pale-yellow solid in 67% yield (0.030 g). $^1$H NMR (400 MHz, DMSO-$d_6$) δ 10.94 (s, 1H), 9.58 (s, 1H), 8.33 (S, 1H), 7.82-7.79 (m, 1H), 7.73-7.71 (m, 1H), 7.65-7.63 (m, 2H), 7.40 (q, J=8.0 Hz, 1H), 6.99-6.97 (m, 1H), 6.95-9.94 (m, 2H); LC-MS m/z calcd for ($C_{16}H_{11}FN_2OS$)H$^+$ 315.1, found 315.0)

Synthesis of N-(2-fluorophenyl)-5-(-(2,2,2-trifluoroacetyl)phenyl)thiophene-2-carboxamide (12)

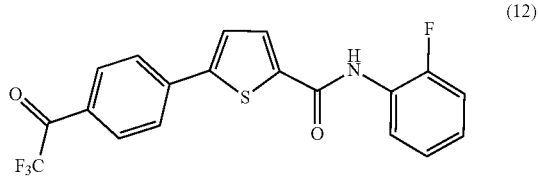 [SMILES: O=C(Nc1ccccc1F)c1ccc(-c2ccc(C(=O)C(F)(F)F)cc2)s1]

(12)

Step 1. Preparation of N-(2-fluorophenyl)-5-(4-formylphenyl)thiophene-2-carboxamide

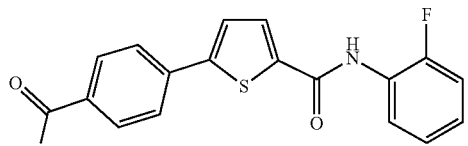

To a solution of 5-bromo-N-(2-fluorophenyl)thiophene-2-carboxamide (0.180 g, 0.300 mmol), which was prepared as outlined in example 7, (4-formylphenyl)boronic acid (0.108 g, 0.720 mmol) and potassium carbonate (0.168 g, 1.2 mmol) in DMF (10 mL) was added Pd(PPh$_3$)$_4$ (0.035 g, 0.030 mmol). The solution was purged of atmosphere and back filled with argon and then heated to 90° C. for 1 h. The reaction was judged done by HPLC and allowed to cool to rt. The reaction was then filtered through a small pad of celite and rinsed with a small amount of DMF. The filtrate was then treated with water and precipitate formed which was filtered through a fritted funnel. The solid was rinsed with water and then hexane and allowed to dry to give the desired product as a green solid in 80% yield (0.173 g). LC-MS m/z calcd for $(C_{18}H_{12}FNO_2S)H^+$ 326.1, found 326.0

Step 2. Synthesis of N-(2-fluorophenyl)-5-(4-(2,2,2-trifluoro-1-hydroxyethyl)phenyl)thiophene-2-carboxamide

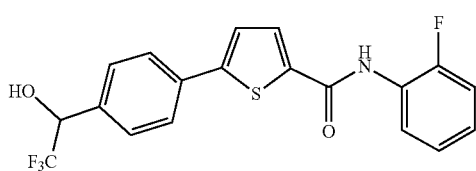 [SMILES: O=C(Nc1ccccc1F)c1ccc(-c2ccc(C(O)C(F)(F)F)cc2)s1]

To a solution of the above aldehyde (0.065 g, 0.2 mmol) in anhydrous THF (1 mL) was added a 2.0M trimethyl (trifluoromethyl)silane-THF solution (0.120 mL, 0.240 mmol) and the reaction was cooled to 0° C. To the cooled mixture was added 1.0M TBAF-THF solution (0.019 mL, 0.019 mmol) and the resulting reaction mixture was stirred 0° C. for 3 h. The reaction progress was slow so additional 2.0M silane (0.114 mL, 0.229 mmol) was added and the reaction was allowed to warm to rt and stir overnight. After 24 h, additional 2.0M silane (0.300 mL, 0.6 mmol) and 1.0M TBAF-THF (0.050 mL, 0.05 mmol) was added and the rxn stirred for an additional 24 h. To this mixture was added a 1.0N HCl solution (10 mL) and the stirred for 5 h. The rxn mixture was concentrated by passing air over the reaction vessel and then diluted with ethyl acetate and water. The layers were separated, and the aqueous layer was extracted with ethyl acetate (3×). The organics were combined, dried over sodium sulfate and concentrated in vacuo. The crude material was purified by flash chromatography (100:0 to 1:1; Hex:EtOAc). Product was isolated as a pale yellow solid. LC-MS m/z calcd for $(C_{19}H_{13}F_4NO_2S)H^+$ 396.1, found 396.0

Step 3. Synthesis of N-(2-fluorophenyl)-5-(4-(2,2,2-trifluoroacetyl)phenyl)thiophene-2-carboxamide (12)

To an ice-cold suspension of the above alcohol (0.050 g, 0.126 mmol) in $CH_2Cl_2$ was added Dess-Martin periodinane (0.056 g, 0.133 mmol) in one portion. The reaction was allowed to slowly warm to rt and stir overnight. The reaction was diluted with diethyl ether and the contents were poured into a flask containing an aqueous solution of $Na_2S_2O_3$ (2 mL) and a sat. solution of sodium bicarbonate (2 mL). The resulting mixture was stirred at rt for 30 min. The layers were separated and the ether layer was washed with brine and then concentrated down. The residue was taken up in a small amount of DMSO and purified with reverse phase chromatography to give the desired product as cream colored solid in 28% yield (0.014 g). $^1$H NMR (400 MHz, DMSO-$d_6$) δ 10.31 (s, 1H), 8.12-8.05 (m, 5H), 7.90 (m, 1H), 7.40 (t, J=8.0 Hz, 1H), 7.36-7.22 (m, 3H), 6.95-9.94 (m, 2H); LC-MS m/z calcd for $(C_{19}H_{11}F_4NO_2S)H^+$ 393.0, found 393.9)

The remaining compounds were synthesized using analogous procedures to those described above. The relevant m/z values are shown in Table 2 below.

TABLE 2

Additional Compounds with m/z Values Found by LC-MS

| Compound # | Structure | m/z [M + H] |
|---|---|---|
| 13 | 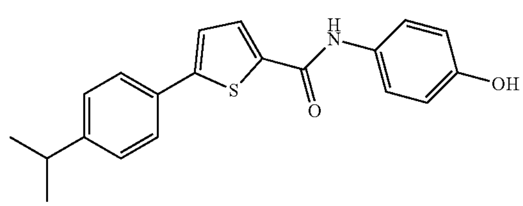 [SMILES: CC(C)c1ccc(-c2ccc(C(=O)Nc3ccc(O)cc3)s2)cc1] | 338.4 |
| 14 | 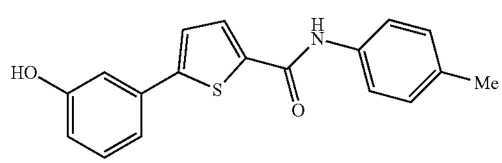 [SMILES: Cc1ccc(NC(=O)c2ccc(-c3cccc(O)c3)s2)cc1] | 310.0 |
| 15 | 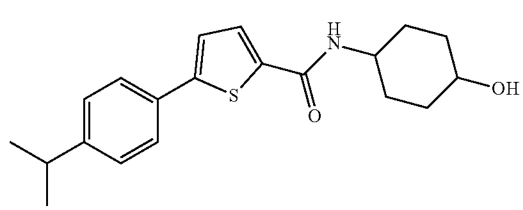 [SMILES: CC(C)c1ccc(-c2ccc(C(=O)NC3CCC(O)CC3)s2)cc1] | 338.4 |

TABLE 2-continued

Additional Compounds with m/z Values Found by LC-MS

| Compound # | Structure | m/z [M + H] |
|---|---|---|
| 16 | 5-(3-hydroxyphenyl)-N-(4-fluorophenyl)thiophene-2-carboxamide | 314.0 |
| 17 | 5-(4-boronophenyl)-N-(4-fluorophenyl)thiophene-2-carboxamide | 342.0 |
| 18 | 5-(4-aminophenyl)-N-(4-methoxyphenyl)thiophene-2-carboxamide | 325.1 |
| 19 | 5-(4-hydroxyphenyl)-N-(3-methylphenyl)thiophene-2-carboxamide | 310.0 |
| 20 | 5-(3-fluorophenyl)-N-(3-hydroxyphenyl)thiophene-2-carboxamide | 314.0 |
| 21 | 5-(3-hydroxyphenyl)-N-(3-fluorophenyl)thiazole-2-carboxamide | 315.0 |
| 22 | 5-(3-hydroxyphenyl)-N-(4-cyanophenyl)thiophene-2-carboxamide | 321.0 |
| 23 | 5-(3-hydroxyphenyl)-N-benzylthiophene-2-carboxamide | 310.1 |
| 24 | 5-(4-hydroxyphenyl)-N-benzylthiophene-2-carboxamide | 310.1 |

TABLE 2-continued

Additional Compounds with m/z Values Found by LC-MS

| Compound # | Structure | m/z [M + H] |
|---|---|---|
| 25 | 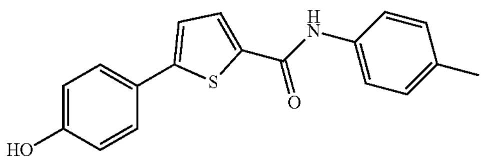 [SMILES: Cc1ccc(NC(=O)c2ccc(-c3ccc(O)cc3)s2)cc1] | 310.1 |
| 26 | 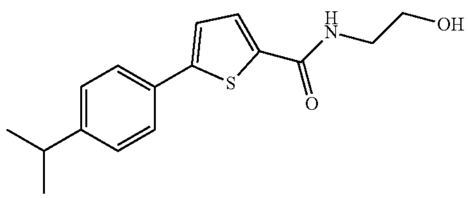 [SMILES: CC(C)c1ccc(-c2ccc(C(=O)NCCO)s2)cc1] | 290.2 |
| 27 | 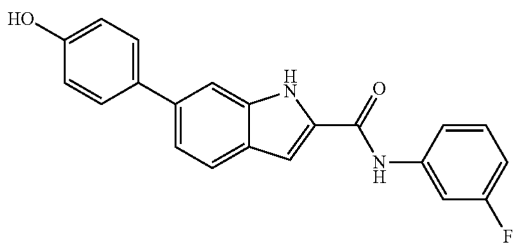 [SMILES: O=C(Nc1cccc(F)c1)c1cc2ccc(-c3ccc(O)cc3)cc2[nH]1] | 347.2 |
| 28 | 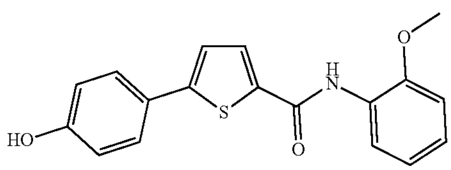 [SMILES: COc1ccccc1NC(=O)c1ccc(-c2ccc(O)cc2)s1] | 326.0 |
| 29 | 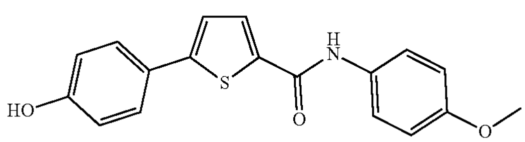 [SMILES: COc1ccc(NC(=O)c2ccc(-c3ccc(O)cc3)s2)cc1] | 326.0 |
| 30 | 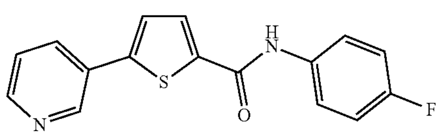 [SMILES: O=C(Nc1ccc(F)cc1)c1ccc(-c2cccnc2)s1] | 299.1 |
| 31 | 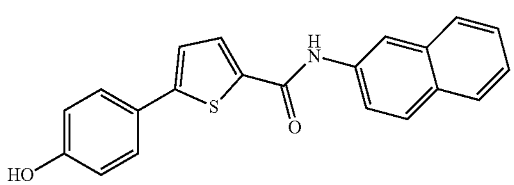 [SMILES: O=C(Nc1ccc2ccccc2c1)c1ccc(-c2ccc(O)cc2)s1] | 346.1 |
| 32 | 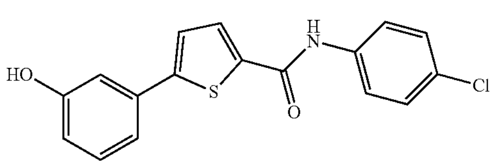 [SMILES: O=C(Nc1ccc(Cl)cc1)c1ccc(-c2cccc(O)c2)s1] | 330.0 |

TABLE 2-continued

Additional Compounds with m/z Values Found by LC-MS

| Compound # | Structure | m/z [M + H] |
|---|---|---|
| 33 | 5-(4-hydroxyphenyl)-N-(4-chlorophenyl)thiophene-2-carboxamide | 330.0 |
| 34 | 5-(3-(hydroxymethyl)phenyl)-N-(3-fluorophenyl)thiophene-2-carboxamide | 328.0 |
| 35 | 5-(4-(hydroxymethyl)phenyl)-N-(3-fluorophenyl)thiophene-2-carboxamide | 328.0 |
| 36 | 5-(4-aminophenyl)-N-(3-fluorobenzyl)furan-2-carboxamide | 311.1 |
| 37 | 5-(thiophen-3-yl)-N-(4-boronophenyl)thiophene-2-carboxamide | 330.0 |
| 38 | 5-(3-fluorophenyl)-N-(4-boronophenyl)thiophene-2-carboxamide | 342.1 |
| 39 | 5-(4-fluorophenyl)-N-(4-boronophenyl)thiophene-2-carboxamide | 342.1 |
| 40 | 5-(2-fluorophenyl)-N-(4-boronophenyl)thiophene-2-carboxamide | 342.1 |
| 41 | N-(benzothiazol-6-yl)-5-(4-hydroxyphenyl)furan-2-carboxamide | 337.0 |

TABLE 2-continued

Additional Compounds with m/z Values Found by LC-MS

| Compound # | Structure | m/z [M + H] |
|---|---|---|
| 42 | benzothiazol-6-yl-NH-C(O)-furan-2-yl-(3-hydroxyphenyl) | 337.0 |
| 43 | (4-hydroxyphenyl)-furan-2-yl-C(O)-NH-CH2-(4-chlorophenyl) | 328.0 |
| 44 | (2-fluorophenyl)-thiophen-2-yl-C(O)-NH-(3-B(OH)2-phenyl) | 342.0 |
| 45 | (3-aminophenyl)-thiophen-2-yl-C(O)-NH-phenyl | 336.1 |
| 46 | (3-aminophenyl)-furan-2-yl-C(O)-NH-benzothiazol-6-yl | 295.0 |
| 47 | (3-carboxyphenyl)-thiophen-2-yl-C(O)-NH-(4-fluorophenyl) | 342.0 |
| 48 | (4-carboxyphenyl)-thiophen-2-yl-C(O)-NH-(4-fluorophenyl) | 342.0 |
| 49 | (4-hydroxyphenyl)-thiophen-2-yl-C(O)-NH-cyclohexyl | 302.1 |
| 50 | (3-fluorophenyl)-thiophen-2-yl-C(O)-NH-(3-B(OH)2-phenyl) | 342.1 |

TABLE 2-continued

Additional Compounds with m/z Values Found by LC-MS

| Compound # | Structure | m/z [M + H] |
|---|---|---|
| 51 | 3-aminophenyl-thiophene-2-carboxamide-N-(4-ethoxyphenyl) | 339.1 |
| 52 | 3-hydroxyphenyl-thiophene-2-carboxamide-N-(4-ethoxyphenyl) | 340.1 |
| 53 | 3-hydroxyphenyl-thiophene-2-carboxamide-N-(2-naphthyl) | 346.1 |
| 54 | 3-aminophenyl-thiophene-2-carboxamide-N-(2-naphthyl) | 345.1 |
| 55 | 4-hydroxyphenyl-thiophene-2-carboxamide-N-phenyl | 296.0 |
| 56 | 3-hydroxyphenyl-thiophene-2-carboxamide-N-(3-thienyl) | 302.0 |
| 57 | 3-thienyl-thiophene-2-carboxamide-N-(3-boronic acid phenyl) | 330.0 |
| 58 | 2-hydroxypyrimidin-5-yl-thiophene-2-carboxamide-N-(3-fluorophenyl) | 316.0 |
| 59 | 3-boronic acid phenyl-thiophene-2-carboxamide-N-(2-fluorophenyl) | 342.0 |
| 60 | 3-chloro-4-hydroxyphenyl-thiophene-2-carboxamide-N-(3-fluorophenyl) | 348.0 |

TABLE 2-continued
Additional Compounds with m/z Values Found by LC-MS
| Compound # | Structure | m/z [M + H] |
|---|---|---|
| 61 | 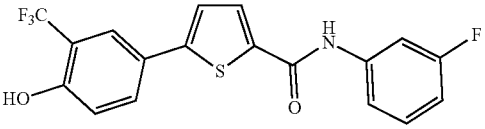 [SMILES: O=C(Nc1cccc(F)c1)c1ccc(-c2ccc(O)c(C(F)(F)F)c2)s1] | 382.0 |
| 62 | 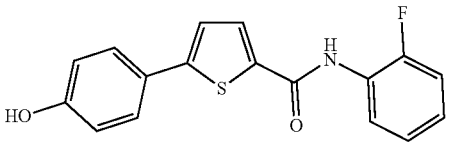 [SMILES: O=C(Nc1ccccc1F)c1ccc(-c2ccc(O)cc2)s1] | 314.1 |
| 63 | 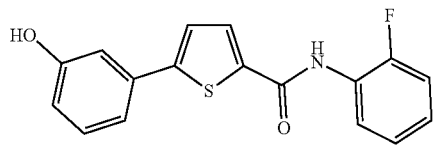 [SMILES: O=C(Nc1ccccc1F)c1ccc(-c2cccc(O)c2)s1] | 314.1 |
| 64 | 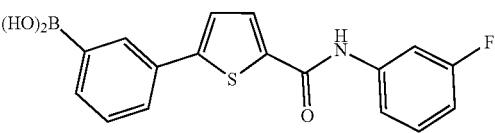 [SMILES: O=C(Nc1cccc(F)c1)c1ccc(-c2cccc(B(O)O)c2)s1] | 342.0 |
| 65 | 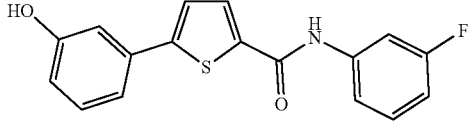 [SMILES: O=C(Nc1cccc(F)c1)c1ccc(-c2cccc(O)c2)s1] | 314.1 |
| 66 | 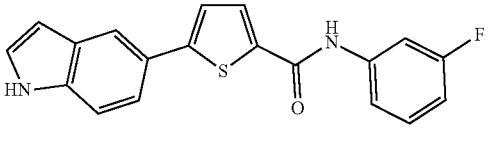 [SMILES: O=C(Nc1cccc(F)c1)c1ccc(-c2ccc3[nH]ccc3c2)s1] | 337.1 |
| 67 | 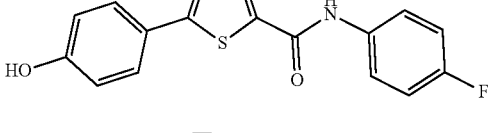 | 314.1 |
| 68 | 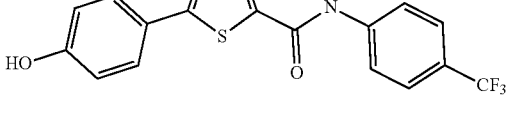 | 364.0 |
| 69 | 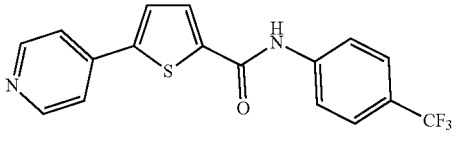 [SMILES: O=C(Nc1ccc(C(F)(F)F)cc1)c1ccc(-c2ccncc2)s1] | 349.1 |
| 70 | 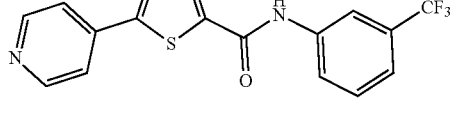 | 349.1 |

TABLE 2-continued
Additional Compounds with m/z Values Found by LC-MS
| Compound # | Structure | m/z [M + H] |
|---|---|---|
| 71 | 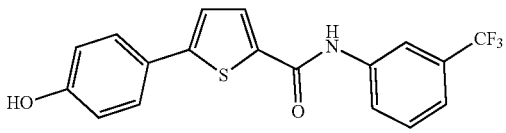 [SMILES: O=C(Nc1cccc(C(F)(F)F)c1)c1ccc(-c2ccc(O)cc2)s1] | 364.0 |
| 72 | 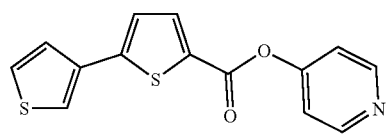 [SMILES: O=C(Oc1ccncc1)c1ccc(-c2ccsc2)s1] | 288.0 |
| 73 | 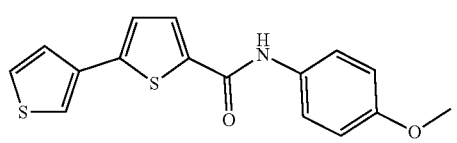 [SMILES: COc1ccc(NC(=O)c2ccc(-c3ccsc3)s2)cc1] | 316.1 |
| 74 | 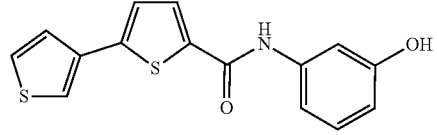 [SMILES: O=C(Nc1cccc(O)c1)c1ccc(-c2ccsc2)s1] | 302.2 |
| 75 | 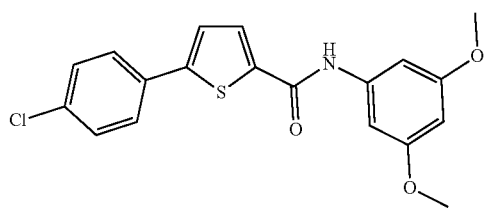 [SMILES: COc1cc(NC(=O)c2ccc(-c3ccc(Cl)cc3)s2)cc(OC)c1] | 374.1 |
| 76 | 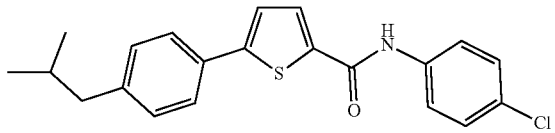 [SMILES: CC(C)Cc1ccc(-c2ccc(C(=O)Nc3ccc(Cl)cc3)s2)cc1] | 370.1 |
| 77 | 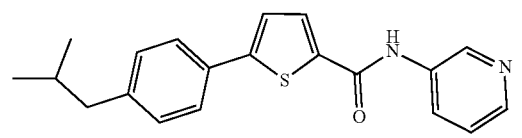 [SMILES: CC(C)Cc1ccc(-c2ccc(C(=O)Nc3cccnc3)s2)cc1] | 337.1 |
| 78 | 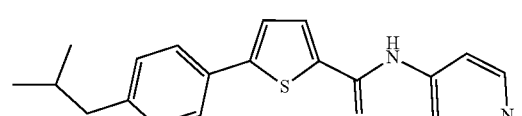 | 337.1 |
| 79 | 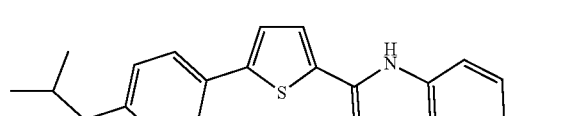 | 352.1 |
| 80 | 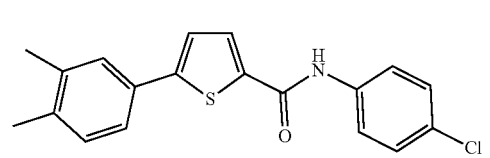 [SMILES: Cc1ccc(-c2ccc(C(=O)Nc3ccc(Cl)cc3)s2)cc1C] | 342.0 |

TABLE 2-continued

Additional Compounds with m/z Values Found by LC-MS

| Compound # | Structure | m/z [M + H] |
|---|---|---|
| 81 | 5-(3,4-dimethylphenyl)-N-(pyridin-3-yl)thiophene-2-carboxamide | 309.1 |
| 82 | 5-(3,4-dimethylphenyl)-N-(pyridin-4-yl)thiophene-2-carboxamide | 309.1 |
| 83 | 5-(3,4-dimethylphenyl)-N-(4-hydroxyphenyl)thiophene-2-carboxamide | 324.1 |
| 84 | N-(4-chlorophenyl)-5-(2-fluorophenyl)thiophene-2-carboxamide | 332.0 |
| 85 | 5-(2-fluorophenyl)-N-(pyridin-3-yl)thiophene-2-carboxamide | 299.0 |
| 86 | 5-(2-fluorophenyl)-N-(pyridin-4-yl)thiophene-2-carboxamide | 299.0 |
| 87 | 5-(2-fluorophenyl)-N-(4-hydroxyphenyl)thiophene-2-carboxamide | 314.1 |
| 88 | 5-(4-chlorophenyl)-N-(3-fluorophenyl)thiophene-2-carboxamide | 332.0 |
| 89 | 5-(3-fluorophenyl)-N-(pyridin-3-yl)thiophene-2-carboxamide | 299.0 |
| 90 | 5-(3-fluorophenyl)-N-(pyridin-4-yl)thiophene-2-carboxamide | 299.0 |

TABLE 2-continued

Additional Compounds with m/z Values Found by LC-MS

| Compound # | Structure | m/z [M + H] |
|---|---|---|
| 91 | 3-F-C6H4-thiophene-C(O)NH-C6H4-4-OH | 314.0 |
| 92 | 4-F-C6H4-thiophene-C(O)NH-C6H4-4-Cl | 332.0 |
| 93 | 4-F-C6H4-thiophene-C(O)NH-(pyridin-3-yl) | 299.0 |
| 94 | 4-F-C6H4-thiophene-C(O)NH-(pyridin-4-yl) | 299.0 |
| 95 | 4-F-C6H4-thiophene-C(O)NH-C6H4-4-OH | 314.1 |
| 96 | 3-NC-C6H4-thiophene-C(O)NH-C6H4-4-Cl | 339.0 |
| 97 | 3-NC-C6H4-thiophene-C(O)NH-(pyridin-3-yl) | 306.0 |
| 98 | 3-NC-C6H4-thiophene-C(O)NH-C6H4-4-OH | 321.0 |
| 99 | 4-NC-C6H4-thiophene-C(O)NH-C6H4-4-Cl | 339.1 |
| 100 | 4-NC-C6H4-thiophene-C(O)NH-(pyridin-3-yl) | 306.0 |
| 101 | 4-NC-C6H4-thiophene-C(O)NH-(pyridin-4-yl) | 306.0 |

TABLE 2-continued

Additional Compounds with m/z Values Found by LC-MS

| Compound # | Structure | m/z [M + H] |
|---|---|---|
| 102 | 4-cyanophenyl-thiophene-2-carboxamide-N-(4-hydroxyphenyl) | 321.1 |
| 103 | 3-thienyl-thiophene-2-carboxamide-N-(pyridin-3-yl) | 287.0 |
| 104 | 3-thienyl-thiophene-2-carboxamide-N-(pyridin-4-yl) | 287.0 |
| 105 | 3-thienyl-thiophene-2-carboxamide-N-(4-hydroxyphenyl) | 302.2 |
| 106 | 2-naphthyl-thiophene-2-carboxamide-N-(pyridin-3-yl) | 331.1 |
| 107 | 3-(trifluoromethyl)phenyl-thiophene-2-carboxamide-N-(4-chlorophenyl) | 382.0 |
| 108 | 3-(trifluoromethyl)phenyl-thiophene-2-carboxamide-N-(pyridin-3-yl) | 349.0 |
| 109 | 3-(trifluoromethyl)phenyl-thiophene-2-carboxamide-N-(pyridin-4-yl) | 349.0 |
| 110 | 3-(trifluoromethyl)phenyl-thiophene-2-carboxamide-N-(4-hydroxyphenyl) | 364.0 |
| 111 | 4-(trifluoromethyl)phenyl-thiophene-2-carboxamide-N-(4-chlorophenyl) | 382.0 |
| 112 | 4-(trifluoromethyl)phenyl-thiophene-2-carboxamide-N-(pyridin-3-yl) | 349.0 |

TABLE 2-continued

Additional Compounds with m/z Values Found by LC-MS

| Compound # | Structure | m/z [M + H] |
|---|---|---|
| 113 | 4-(trifluoromethyl)phenyl-thiophene-2-carboxamide-N-(pyridin-4-yl) | 349.0 |
| 114 | 4-(trifluoromethyl)phenyl-thiophene-2-carboxamide-N-(4-hydroxyphenyl) | 364.0 |
| 115 | 4-isopropoxyphenyl-thiophene-2-carboxamide-N-(pyridin-3-yl) | 339.1 |
| 116 | 4-isopropoxyphenyl-thiophene-2-carboxamide-N-(pyridin-4-yl) | 339.1 |
| 117 | 3-isopropylphenyl-thiophene-2-carboxamide-N-(4-chlorophenyl) | 356.1 |
| 118 | 3-isopropylphenyl-thiophene-2-carboxamide-N-(pyridin-3-yl) | 323.1 |
| 119 | 3-isopropylphenyl-thiophene-2-carboxamide-N-(pyridin-4-yl) | 323.1 |
| 120 | naphthalen-2-yl-thiophene-2-carboxamide-N-(pyridin-4-yl) | 331.1 |
| 121 | naphthalen-2-yl-thiophene-2-carboxamide-N-(4-hydroxyphenyl) | 346.1 |
| 122 | 5-(4-hydroxyphenyl)-1H-pyrazole-3-carboxamide-N-(naphthalen-2-yl) | 330.1 |

TABLE 2-continued
Additional Compounds with m/z Values Found by LC-MS
| Compound # | Structure | m/z [M + H] |
|---|---|---|
| 123 | 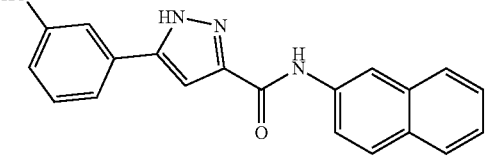 | 330.1 |
| 124 | 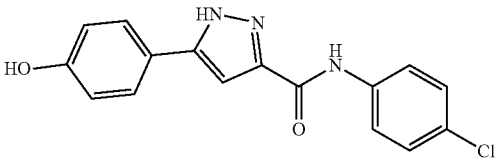 [SMILES: O=C(Nc1ccc(Cl)cc1)c1cc(-c2ccc(O)cc2)[nH]n1] | 314.0 |
| 125 | 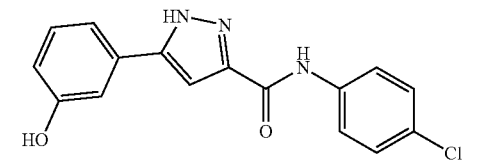 [SMILES: O=C(Nc1ccc(Cl)cc1)c1cc(-c2cccc(O)c2)[nH]n1] | 314.0 |
| 126 | 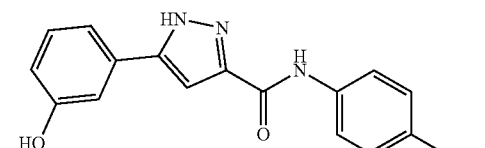 | 294.1 |
| 127 | 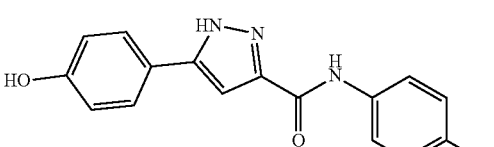 | 294.1 |
| 128 | 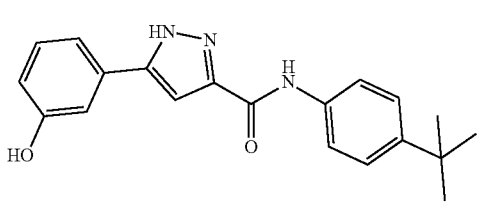 [SMILES: CC(C)(C)c1ccc(NC(=O)c2cc(-c3cccc(O)c3)[nH]n2)cc1] | 336.2 |
| 129 | 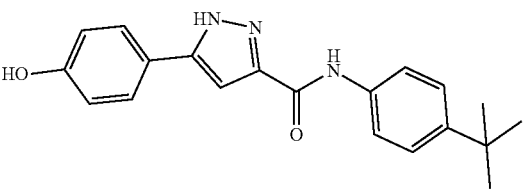 [SMILES: CC(C)(C)c1ccc(NC(=O)c2cc(-c3ccc(O)cc3)[nH]n2)cc1] | 336.2 |
| 130 | 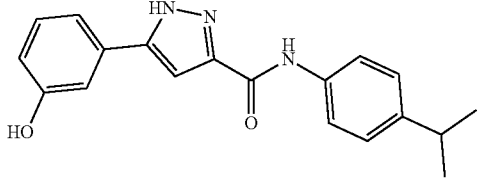 [SMILES: CC(C)c1ccc(NC(=O)c2cc(-c3cccc(O)c3)[nH]n2)cc1] | 322.1 |

TABLE 2-continued

Additional Compounds with m/z Values Found by LC-MS

| Compound # | Structure | m/z [M + H] |
|---|---|---|
| 131 | 5-(4-hydroxyphenyl)-N-(4-hydroxyphenyl)-1H-pyrazole-3-carboxamide | 296.1 |
| 132 | 5-(4-chlorophenyl)-N-(3-aminophenyl)thiophene-2-carboxamide | 329.0 |
| 133 | 5-(4-tert-butylphenyl)-N-(4-hydroxyphenyl)furan-2-carboxamide | 336.1 |
| 134 | 5-(3-hydroxyphenyl)-N-(4-hydroxyphenyl)-1H-pyrazole-3-carboxamide | 296.1 |
| 135 | 5-phenyl-N-(4-hydroxycyclohexyl)furan-2-carboxamide | 286.1 |
| 136 | 5-(3-hydroxyphenyl)-N-(4-chlorobenzyl)furan-2-carboxamide | 327.1 |
| 137 | 5-(4-isopropylphenyl)-N-(pyridin-2-yl)thiophene-2-carboxamide | 323.1 |
| 138 | 5-(4-isopropylphenyl)-N-(pyridin-3-yl)thiophene-2-carboxamide | 323.1 |
| 139 | 5-(4-isopropylphenyl)-N-(pyridin-4-yl)thiophene-2-carboxamide | 323.1 |
| 140 | 5-(4-isopropylphenyl)-N-(3-hydroxyphenyl)thiophene-2-carboxamide | 338.2 |

TABLE 2-continued
Additional Compounds with m/z Values Found by LC-MS
| Compound # | Structure | m/z [M + H] |
|---|---|---|
| 141 | 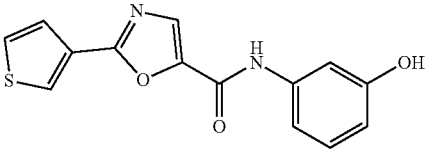 [SMILES: O=C(Nc1cccc(O)c1)c1cnc(-c2ccsc2)o1] | 287.0 |
| 142 | 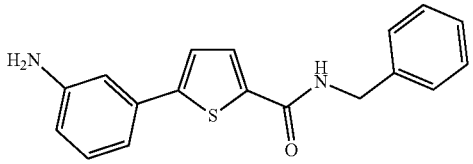 [SMILES: Nc1cccc(-c2ccc(C(=O)NCc3ccccc3)s2)c1] | 309.1 |
| 143 | 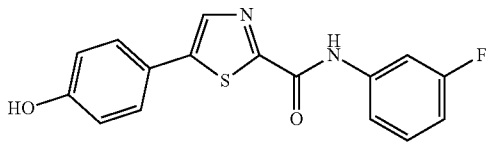 [SMILES: O=C(Nc1cccc(F)c1)c1ncc(-c2ccc(O)cc2)s1] | 299.1 |
| 144 | 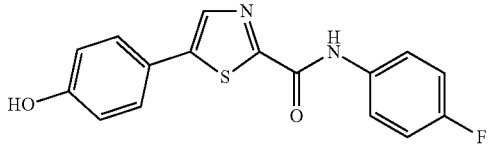 [SMILES: O=C(Nc1ccc(F)cc1)c1ncc(-c2ccc(O)cc2)s1] | 315.0 |
| 145 | 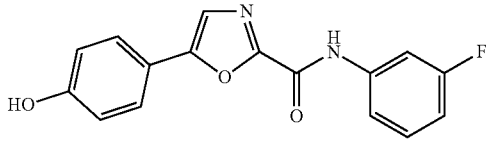 [SMILES: O=C(Nc1cccc(F)c1)c1ncc(-c2ccc(O)cc2)o1] | 299.1 |
| 146 | 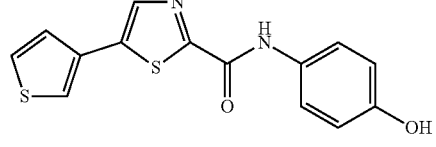 | 303.0 |
| 147 | 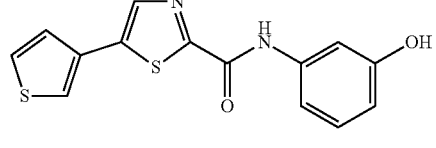 | 303.0 |
| 148 | 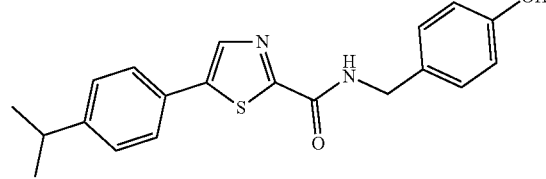 | |
| 149 | 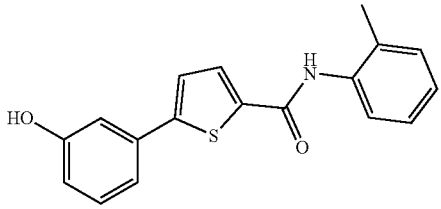 [SMILES: Cc1ccccc1NC(=O)c1ccc(-c2cccc(O)c2)s1] | 310.1 |

US 11,795,162 B2
TABLE 2-continued
Additional Compounds with m/z Values Found by LC-MS
| Compound # | Structure | m/z [M + H] |
|---|---|---|
| 150 | 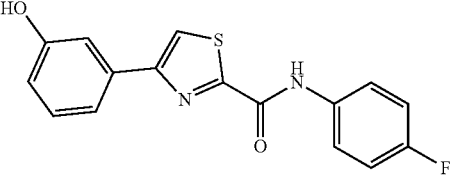 [SMILES: O=C(Nc1ccc(F)cc1)c1nc(-c2cccc(O)c2)cs1] | 315.0 |
| 151 | 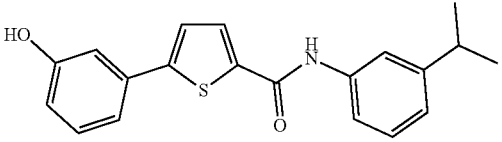 [SMILES: CC(C)c1cccc(NC(=O)c2ccc(-c3cccc(O)c3)s2)c1] | 338.1 |
| 152 | 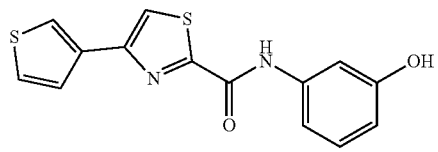 [SMILES: O=C(Nc1cccc(O)c1)c1nc(-c2ccsc2)cs1] | 303.0 |
| 153 | 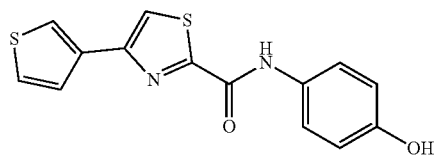 [SMILES: O=C(Nc1ccc(O)cc1)c1nc(-c2ccsc2)cs1] | 303.0 |
| 154 | 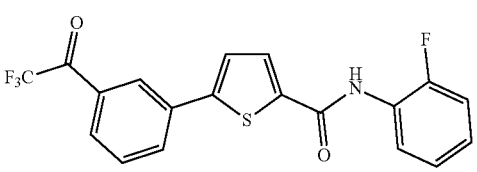 [SMILES: O=C(Nc1ccccc1F)c1ccc(-c2cccc(C(=O)C(F)(F)F)c2)s1] | 412.0 |
| 155 | 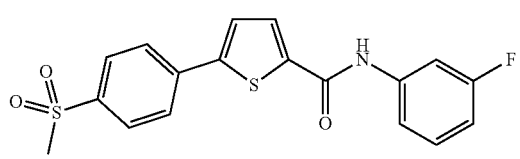 [SMILES: CS(=O)(=O)c1ccc(-c2ccc(C(=O)Nc3cccc(F)c3)s2)cc1] | 376.0 |
| 156 | 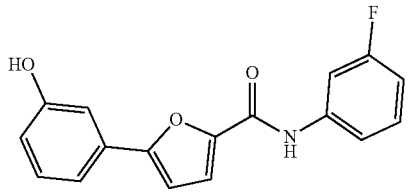 [SMILES: O=C(Nc1cccc(F)c1)c1ccc(-c2cccc(O)c2)o1] | 298.1 |
| 157 | 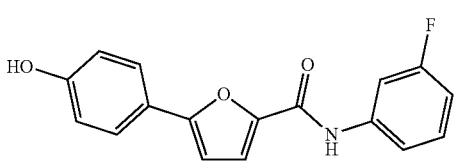 [SMILES: O=C(Nc1cccc(F)c1)c1ccc(-c2ccc(O)cc2)o1] | 298.1 |
| 158 | 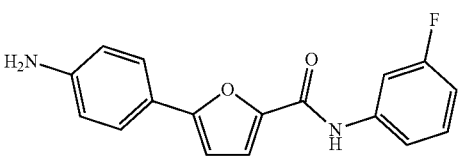 [SMILES: Nc1ccc(-c2ccc(C(=O)Nc3cccc(F)c3)o2)cc1] | 297.1 |

TABLE 2-continued

Additional Compounds with m/z Values Found by LC-MS

| Compound # | Structure | m/z [M + H] |
|---|---|---|
| 159 | 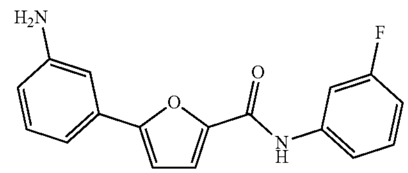 [SMILES: Nc1cccc(-c2ccc(C(=O)Nc3cccc(F)c3)o2)c1] | 297.1 |

C. Testing Data

Luciferase Assay. HEK293 cells were maintained in Dulbecco's modified Eagles medium (DMEM) supplemented with 10% fetal bovine serum at 37° C. under 5% $CO_2$. Cells were plated in 96-well plates at a density of $2.5 \times 10^4$ cells/well and transiently transfected using Lipofectamine™ 2000 (Invitrogen) according to manufacturer's instructions. Cells were transfected with ERRE reporter construct and pcDNA3.1 ERRγ. 24 hour post-transfection, the cells were treated with vehicle or compound for 24 hours. Luciferase activity was measured using the One-Glo Tox™ luciferase reporter assay system (Promega) and are shown in Table 3 below. The values indicated represent the means±S.E. from four independently transfected wells.

TABLE 3

Data for selected compounds in the full-length luciferase assay

| Compound # | ERRγ EC50 (μM) |
|---|---|
| 8 | 0.089 |
| 9 | 0.273 |
| 46 | 0.125 |
| 50 | 0.563 |
| 74 | 1.01 |
| 114 | 2.675 |
| 122 | 0.734 |
| 125 | >25.0 |
| 135 | 3.5 |
| 157 | 3.4 |

Protein Thermal Shift Assay.

ERR gamma protein was diluted in a buffer containing 25 mM HEPES pH 7.5, 300 mM NaCl, 10 mM DTT, 1 mM EDTA at a final concentration of 0.1 mg/mL and mixed with 5×SYPRO-Orange dye (Life technologies S6650). Ligands were diluted at final concentrations of 20 uM, 10 uM, 5 uM and 2.5 uM. Six replicate reactions were set up and run in Applied Biosystems Quantstudio 7 Real-Time PCR system. Data were collected at a ramp rate of 0.05° C./s from 24° C. through 95° C. and analyzed using Protein Thermal Shift Software 1.3.

Activity ranges for compounds tested in the thermal shift assay at 20 μM are indicated below:

Compounds exhibiting T.S. range from 0-2° C.: 3, 4, 6, 10, 12, 13, 15, 18, 19, 22, 29, 31, 33, 35, 36, 42, 48, 58, 59, 62, 63, 67-71, 73, 75-77, 80-83, 85, 86, 89, 92-94, 96, 97, 99-101, 103, 107, 108, 111-113, 115-119, 121, 126, 128-130, 134, 136-138, 140-143, 147-154, 155

Compounds exhibiting T.S. range between 2-4° C.: 1, 2, 5, 14, 17, 20, 25, 32, 34, 41, 44, 46, 49, 50, 52, 54, 56, 60 65, 66, 78, 79, 84, 87, 90, 91, 95, 98, 102, 105, 106, 109, 110, 114, 120, 122-125, 127, 131, 139, 144-146

Compounds exhibiting a T.S. range of >4° C.: 7, 9, 11, 16, 21, 51, 53, 55, 57, 61, 131, 132

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference:

Mangelsdorf, D. J. et al. The Nuclear Receptor Superfamily—the 2nd Decade. Cell 83, 835-839 (1995).

Evans, R. M. The steroid and thyroid hormone receptor superfamily. Science 240, 889-895 (1988).

Kliewer, S. A., Lehmann, J. M. & Willson, T. M. Orphan nuclear receptors: Shifting endocrinology into reverse. Science 284, 757-760 (1999).

Giguere, V. Orphan nuclear receptors: From gene to function. Endocrine Reviews 20, 689-725 (1999).

Mangelsdorf, D. J. & Evans, R. M. The Rxr Heterodimers and Orphan Receptors. Cell 83, 841-850 (1995).

Omalley, B. W. & Conneely, 0. M. ORPHAN RECEPTORS—IN SEARCH OF A UNIFYING HYPOTHESIS FOR ACTIVATION. Molecular Endocrinology 6, 1359-1361 (1992).

Giguere, V. Transcriptional control of energy homeostasis by the estrogen-related receptors. Endocrine Reviews 29, 677-696, doi:10.1210/er.2008-0017 (2008).

Giguere, V., Yang, N., Segui, P. & Evans, R. M. Identification of a new class of steroid hormone receptors. Nature 331, 91-94, doi:10.1038/331091a0 (1988).

Chen, F. et al. Identification of two $hERR_2$-related novel nuclear receptors utilizing bioinformatics and inverse PCR. Gene 228, 101-109 (1999).

Sladek, R., Bader, J. A. & Giguere, V. The orphan nuclear receptor estrogen-related receptor alpha is a transcriptional regulator of the human medium-chain acyl coenzyme A dehydrogenase gene. *Molecular and Cellular Biology* 17, 5400-5409 (1997).

Matsakas, A., Yadav, V., Lorca, S. & Narkar, V. Muscle ERRgamma mitigates Duchenne muscular dystrophy via metabolic and angiogenic reprogramming. *Faseb J* 27, 4004-4016, doi:10.1096/fj.13-228296 (2013).

Narkar, V. A. et al. Exercise and PGC-1 alpha-independent synchronization of type I muscle metabolism and vasculature by ERRgamma. *Cell Metabolism* 13, 283-293, doi:10.1016/j.cmet.2011.01.019 (2011).

Rangwala, S. M. et al. Estrogen-related receptor gamma is a key regulator of muscle mitochondrial activity and oxidative capacity. *The Journal of biological chemistry* 285, 22619-22629, doi:10.1074/jbc.M110.125401 (2010).

Tremblay, G. B. et al. Diethylstilbestrol regulates trophoblast stem cell differentiation as a ligand of orphan nuclear receptor ERR beta. *Genes & development* 15, 833-838, doi:10.1101/gad.873401 (2001a).

Coward, P., Lee, D., Hull, M. V. & Lehmann, J. M. 4-Hydroxytamoxifen binds to and deactivates the estrogen-related receptor gamma. *Proceedings of the National Academy of Sciences of the United States of America* 98, 8880-8884 (2001).

Tremblay, G. B., Bergeron, D. & Giguere, V. 4-Hydroxytamoxifen is an isoform-specific inhibitor of orphan estrogen-receptor-related (ERR) nuclear receptors beta and gamma. *Endocrinology* 142, 4572-4575 (2001b).

Busch, B. B. et al. Identification of a selective inverse agonist for the orphan nuclear receptor estrogen-related receptor alpha. *Journal of Medicinal Chemistry* 47, 5593-5596, doi:10.1021/jm049334f (2004).

Zuercher, W. J. et al. Identification and structure-activity relationship of phenolic acyl hydrazones as selective agonists for the estrogen-related orphan nuclear receptors ERRbeta and ERRgamma. *Journal of Medicinal Chemistry* 48, 3107-3109, doi:10.1021/jm050161j (2005).

What is claimed:

1. A compound of the formula:

$$X_1\text{-}Y_1\text{-}L\text{-}A\text{-}R_1 \quad (I)$$

wherein:

$X_1$ is $aryl_{(C\leq12)}$ or a substituted version of this group; or -arenediyl$_{(C\leq12)}$-$R_2$ or a substituted version thereof, wherein:

$R_2$ is -B(OR')(OR''), —NR$_3$R$_4$, —C(O)OR$_5$, —C(O)NR$_6$R$_7$; wherein:

$R_3$, $R_4$, $R_6$, and $R_7$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or $R_3$ and $R_4$ or $R_6$ and $R_7$ are taken together and are a divalent amino protecting group;

R' and R'' are hydrogen, alkyl$_{(C\leq12)}$, cycloalkyl$_{(C\leq12)}$, aryl$_{(C\leq12)}$, aralkyl$_{(C\leq12)}$, or a substituted version of any of these groups; and $R_5$ is alkyl$_{(C\leq12)}$, cycloalkyl$_{(C\leq12)}$, aryl$_{(C\leq12)}$, aralkyl$_{(C\leq12)}$, or a substituted version of any of these groups; or $R_2$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;

$Y_1$ is thiophene or substituted thiophene;

L is —C(O)—;

A is -NR$_8$—, wherein:

$R_8$ is hydrogen, alkyl$_{(C\leq8)}$, or substituted alkyl$_{(C\leq8)}$;

$R_1$ is alkyl$_{(C\leq12)}$, cycloalkyl$_{(C\leq12)}$, aryl$_{(C\leq18)}$, heteroaryl$_{(C\leq18)}$, aralkyl$_{(C\leq18)}$, or a substituted version of any of these groups; or aryl$_{(C\leq12)}$ or substituted aryl$_{(C\leq12)}$, wherein two hydrogen atoms have been replaced with —NR$_a$C(O)NR$_b$—;

wherein:

$R_a$ and $R_b$ are each independently hydrogen, alkyl$_{(C\leq6)}$, or substituted alkyl$_{(C\leq6)}$; or $R_1$ is -arenediyl$_{(C\leq12)}$-$R_9$, -heteroarenediyl$_{(C\leq12)}$-$R_9$, or a substituted version thereof, wherein:

$R_9$ is -B(OR''')(OR''''), -NR$_{10}$R$_{11}$, —C(O)OR$_{12}$, —C(O)NR$_{13}$R$_{14}$; wherein:

$R_{10}$, $R_{11}$, $R_{13}$, and $R_{14}$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or $R_{10}$ and $R_{11}$ or $R_{13}$ and $R_{14}$ are taken together and are a divalent amino protecting group;

R''' and R'''' are hydrogen, alkyl$_{(C\leq12)}$, cycloalkyl$_{(C\leq12)}$, aryl$_{(C\leq12)}$, aralkyl$_{(C\leq12)}$, or a substituted version of any of these groups; and $R_{12}$ is alkyl$_{(C\leq12)}$, cycloalkyl$_{(C\leq12)}$, aryl$_{(C\leq12)}$, aralkyl$_{(C\leq12)}$, or a substituted version of any of these groups; or $R_9$ is alkyl$_{(C\leq12)}$, cycloalkyl$_{(C\leq12)}$, aryl$_{(C\leq12)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;

or a pharmaceutically acceptable salt thereof.

2. A compound of the formula:

$$X_1\text{-}Y_1\text{-}L\text{-}A\text{-}R_1 \quad (I)$$

wherein:

$X_1$ is aryl$_{(C\leq12)}$ or a substituted version of this group; or -arenediyl$_{(C\leq12)}$-$R_2$ or a substituted version thereof, wherein:

$R_2$ is -B(OR')(OR''), —NR$_3$R$_4$, —C(O)OR$_5$, —C(O)NR$_6$R$_7$, —C(O)R$_{15}$, —SO$_2$R$_{16}$; wherein:

$R_3$, $R_4$, $R_6$, and $R_7$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or $R_3$ and $R_4$ or $R_6$ and $R_7$ are taken together and are a divalent amino protecting group;

R' and R'' are hydrogen, alkyl$_{(C\leq12)}$, cycloalkyl$_{(C\leq12)}$, aryl$_{(C\leq12)}$, aralkyl$_{(C\leq12)}$, or a substituted version of any of these groups; and $R_5$, $R_{15}$, and $R_{16}$ are each independently alkyl$_{(C\leq12)}$, cycloalkyl$_{(C\leq12)}$, aryl$_{(C\leq12)}$, aralkyl$_{(C\leq12)}$, or a substituted version of any of these groups; or $R_2$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;

Y$_1$ is thiophene or substituted thiophene;

L is —C(O)—;

A is -NR$_8$—, wherein:

R$_8$ is hydrogen, alkyl$_{(C\leq8)}$, or substituted alkyl$_{(C\leq8)}$;

R$_1$ is alkyl$_{(C\leq12)}$, cycloalkyl$_{(C\leq12)}$, aryl$_{(C\leq18)}$, heteroaryl$_{(C\leq18)}$, aralkyl$_{(C\leq18)}$, or a substituted version of any of these groups; or aryl$_{(C\leq12)}$ or substituted aryl$_{(C\leq12)}$, wherein two hydrogen atoms have been replaced with —NR$_a$C(O)NR$_b$—; wherein:

R$_a$ and R$_b$ are each independently hydrogen, alkyl$_{(C\leq6)}$, or substituted alkyl$_{(C\leq6)}$; or R$_1$ is -arenediyl$_{(C\leq12)}$-R$_9$, -heteroarenediyl$_{(C\leq12)}$-R$_9$, or a substituted version thereof, wherein:

R$_9$ is -B(OR''')(OR''''), -NR$_{10}$R$_{11}$, —C(O)OR$_{12}$, —C(O)NR$_{13}$R$_{14}$; wherein:

R$_{10}$, R$_{11}$, R$_{13}$, and R$_{14}$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or R$_{10}$ and R$_{11}$ or R$_{13}$ and R$_{14}$ are taken together and are a divalent amino protecting group;

R''' and R'''' are hydrogen, alkyl$_{(C\leq12)}$, cycloalkyl$_{(C\leq12)}$, aryl$_{(C\leq12)}$, aralkyl$_{(C\leq12)}$, or a substituted version of any of these groups; and R$_{12}$ is alkyl$_{(C\leq12)}$, cycloalkyl$_{(C\leq12)}$, aryl$_{(C\leq12)}$, aralkyl$_{(C\leq12)}$, or a substituted version of any of these groups; or R$_9$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;

or a pharmaceutically acceptable salt thereof.

3. The compound of claim 1 further defined as:

$$X_1\text{-}Y_1\text{-}C(O)\text{-}A\text{-}R_1 \quad (I)$$

wherein:

X$_1$ is aryl$_{(C\leq12)}$ or a substituted version of this group; or -arenediyl$_{(C\leq12)}$-R$_2$ or a substituted version thereof, wherein:

R$_2$ is -B(OR')(OR''), —NR$_3$R$_4$, —C(O)OR$_5$, —C(O)NR$_6$R$_7$; wherein:

R$_3$, R$_4$, R$_6$, and R$_7$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or R$_3$ and R$_4$ or R$_6$ and R$_7$ are taken together and are a divalent amino protecting group;

R' and R'' are hydrogen, alkyl$_{(C\leq12)}$, cycloalkyl$_{(C\leq12)}$, aryl$_{(C\leq12)}$, aralkyl(c≤12), or a substituted version of any of these groups; and R$_5$ is alkyl$_{(C\leq12)}$, cycloalkyl$_{(C\leq12)}$, aryl$_{(C\leq12)}$, aralkyl$_{(C\leq12)}$, or a substituted version of any of these groups; or R$_2$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;

Y$_1$ is thiophene or substituted thiophene;

A is -NR$_8$—, wherein:

R$_8$ is hydrogen, alkyl$_{(C\leq8)}$, substituted alkyl$_{(C\leq8)}$;

R$_1$ is alkyl$_{(C\leq12)}$, cycloalkyl$_{(C\leq12)}$, aryl$_{(C\leq18)}$, heteroaryl$_{(C\leq18)}$, aralkyl$_{(C\leq18)}$, or a substituted version of any of these groups; or aryl$_{(C\leq12)}$ or substituted aryl$_{(C\leq12)}$, wherein two hydrogen atoms have been replaced with —NR$_a$C(O)NR$_b$—; wherein:

R$_a$ and R$_b$ are each independently hydrogen, alkyl$_{(C\leq6)}$, or substituted alkyl$_{(C\leq6)}$; or R$_1$ is -arenediyl$_{(C\leq12)}$-R$_9$, -heteroarenediyl$_{(C\leq12)}$-R$_9$, or a substituted version thereof, wherein:

R$_9$ is -B(OR''')(OR''''), -NR$_{10}$R$_{11}$, —C(O)OR$_{12}$, —C(O)NR$_{13}$R$_{14}$; wherein:

R$_{10}$, R$_{11}$, R$_{13}$, and R$_{14}$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or R$_{10}$ and R$_{11}$ or R$_{13}$ and R$_{14}$ are taken together and are a divalent amino protecting group;

R''' and R'''' are hydrogen, alkyl$_{(C\leq12)}$, cycloalkyl$_{(C\leq12)}$, aryl$_{(C\leq12)}$, aralkyl$_{(C\leq12)}$, or a substituted version of any of these groups; and R$_{12}$ is alkyl$_{(C\leq12)}$, cycloalkyl$_{(C\leq12)}$, aryl$_{(C\leq12)}$, aralkyl$_{(C\leq12)}$, or a substituted version of any of these groups; or R$_9$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;

or a pharmaceutically acceptable salt thereof.

4. The compound of claim 1 further defined as:

$$X_1\text{-}Y_1\text{-}C(O)\text{-}A\text{-}R_1 \quad (I)$$

wherein:

X$_1$ is aryl$_{(C\leq12)}$ or a substituted version of this group; or -arenediyl$_{(C\leq12)}$-R$_2$ or a substituted version thereof, wherein:

R$_2$ is -B(OR')(OR''), —NR$_3$R$_4$, —C(O)OR$_5$, —C(O)NR$_6$R$_7$; wherein:

R$_3$, R$_4$, R$_6$, and R$_7$ are each independently hydrogen, alkyl$_{(C\leq12)}$, cycloalkyl$_{(C\leq12)}$, aryl$_{(C\leq12)}$, aralkyl$_{(C\leq12)}$, acyl$_{(C\leq12)}$, or a substituted version of any of these groups, or a monovalent amino protecting group; or R$_3$ and R$_4$ or R$_6$ and R$_7$ are taken together and are a divalent amino protecting group;

R' and R'' are hydrogen, alkyl$_{(C\leq12)}$, cycloalkyl$_{(C\leq12)}$, aryl$_{(C\leq12)}$, aralkyl$_{(C\leq12)}$, or a substituted version of any of these groups; and R$_5$ is alkyl$_{(C\leq12)}$, cycloalkyl$_{(C\leq12)}$, aryl$_{(C\leq12)}$, aralkyl$_{(C\leq12)}$, or a substituted version of any of these groups; or R$_2$ is alkyl$_{(C\leq12)}$, cycloalkyl$_{(C\leq12)}$, aryl$_{(C\leq18)}$, heteroaryl$_{(C\leq18)}$, heterocycloalkyl$_{(C\leq12)}$, aralkyl$_{(C\leq18)}$, heteroaralkyl$_{(C\leq18)}$, alkoxy$_{(C\leq12)}$, cycloalkoxy$_{(C\leq12)}$, aryloxy$_{(C\leq12)}$, aralkoxy$_{(C\leq12)}$, or a substituted version of any of these eleven groups;

Y$_1$ is thiophene or substituted thiophene;

A is -NR$_8$—, wherein:

R$_8$ is hydrogen, alkyl$_{(C\leq8)}$, or substituted alkyl$_{(C\leq8)}$;

R$_1$ is aryl$_{(C\leq18)}$, heteroaryl$_{(C\leq18)}$, aralkyl$_{(C\leq18)}$, or a substituted version of any of these groups;

or a pharmaceutically acceptable salt thereof.

5. The compound of claim 1 further defined as:

$$X_1\text{-}Y_1\text{-}C(O)\text{-}A\text{-}R_1 \qquad (I)$$

wherein:
X$_1$ is aryl$_{(C\leq12)}$ or a substituted version of this group;
Y$_1$ is thiophene or substituted thiophene;
A is -NR$_8$—, wherein:
R$_8$ is hydrogen, alkyl$_{(C\leq8)}$, substituted alkyl$_{(C\leq8)}$;
R$_1$ is aryl$_{(C\leq18)}$, heteroaryl$_{(C\leq18)}$, or a substituted version of any of these groups;
or a pharmaceutically acceptable salt thereof.

6. The compound of claim 1, wherein Y$_1$ is thiophene.

7. The compound of claim 1, wherein X$_1$ is aryl$_{(C\leq12)}$ or substituted aryl$_{(C\leq12)}$.

8. The compound of claim 7, wherein X$_1$ is aryl$_{(C\leq12)}$.

9. The compound of claim 7, wherein X$_1$ is substituted aryl$_{(C\leq12)}$.

10. The compound of claim 1, wherein X$_1$ is -arenediyl$_{(C\leq12)}$-R$_2$.

11. The compound of claim 1, wherein R$_1$ is aryl$_{(C\leq12)}$ or substituted aryl$_{(C\leq12)}$.

12. The compound of claim 1, wherein R$_1$ is heteroaryl$_{(C\leq12)}$ or substituted heteroaryl$_{(C\leq12)}$.

13. The compound of claim 1, wherein R$_1$ is -arenediyl$_{(C\leq12)}$-R$_9$.

14. The compound of claim 1 further defined as:

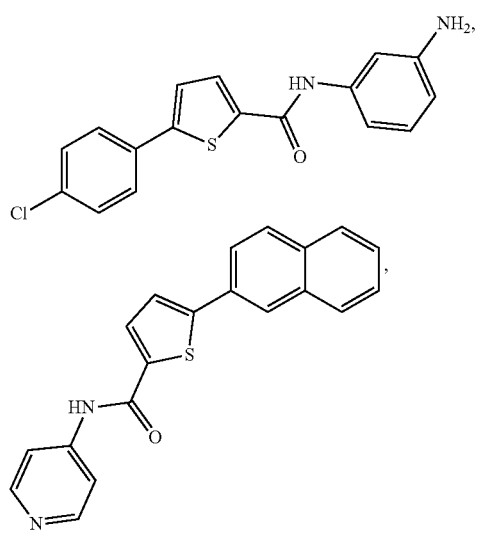

-continued

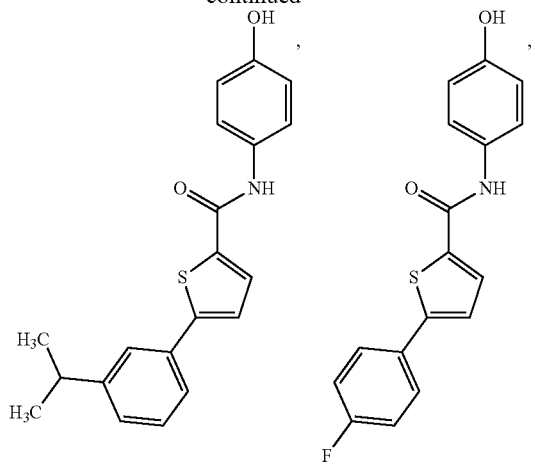

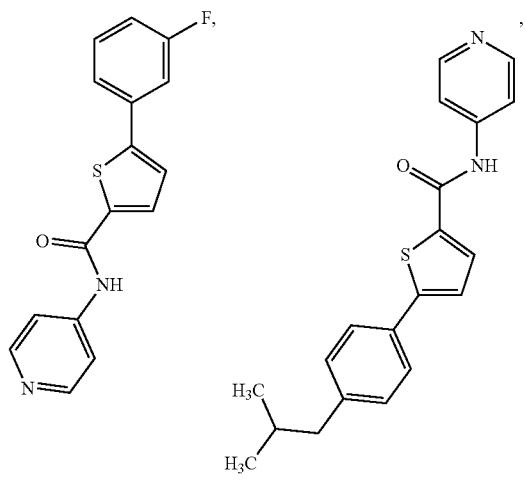

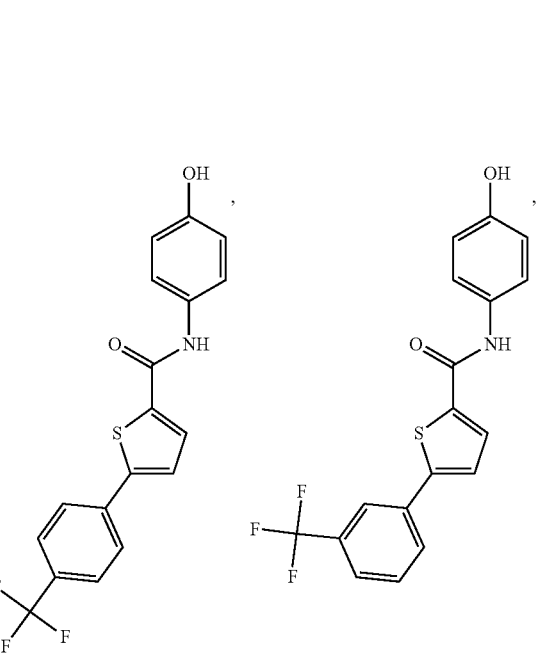

117
-continued
118
-continued
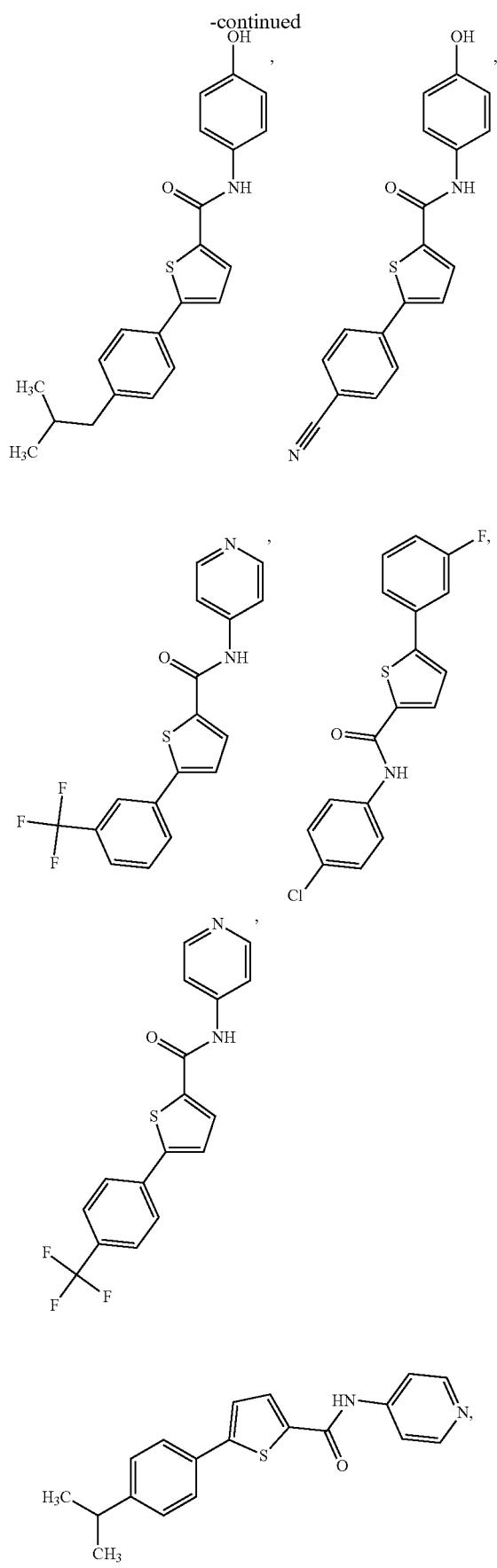
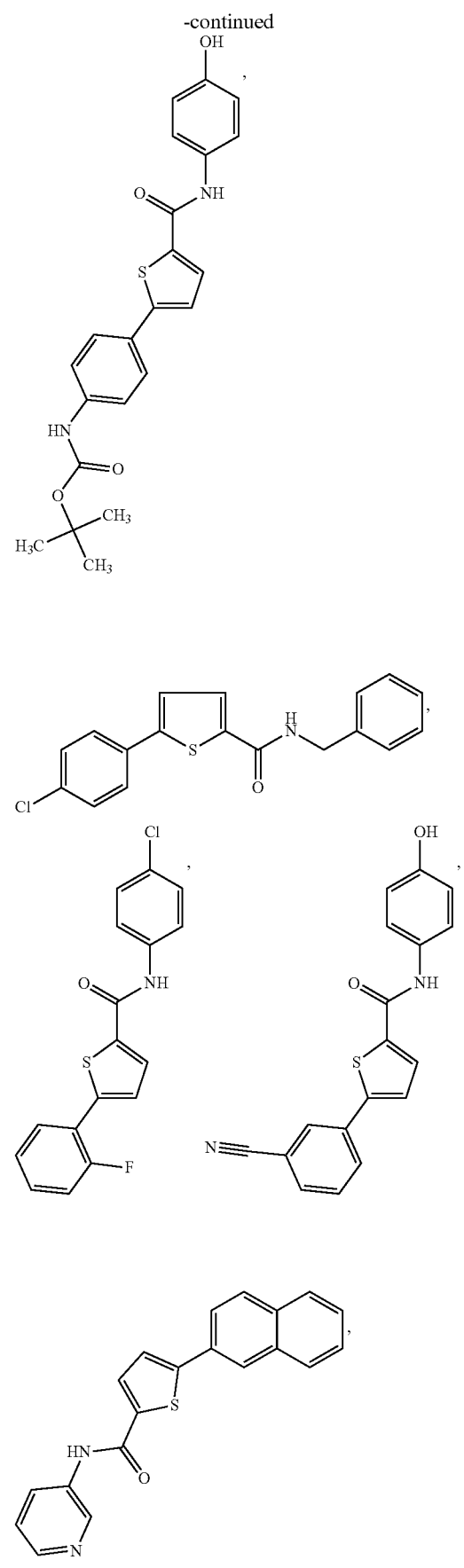

119
-continued
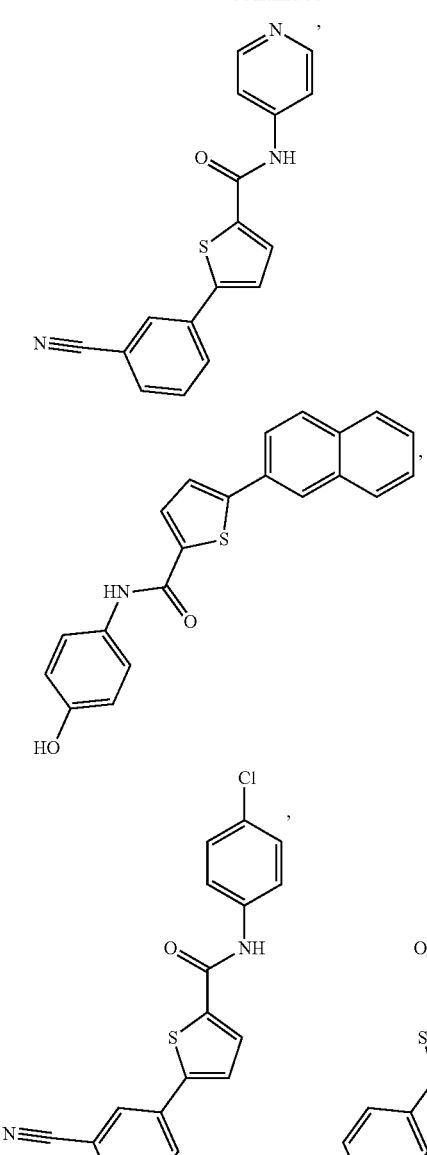
120
-continued
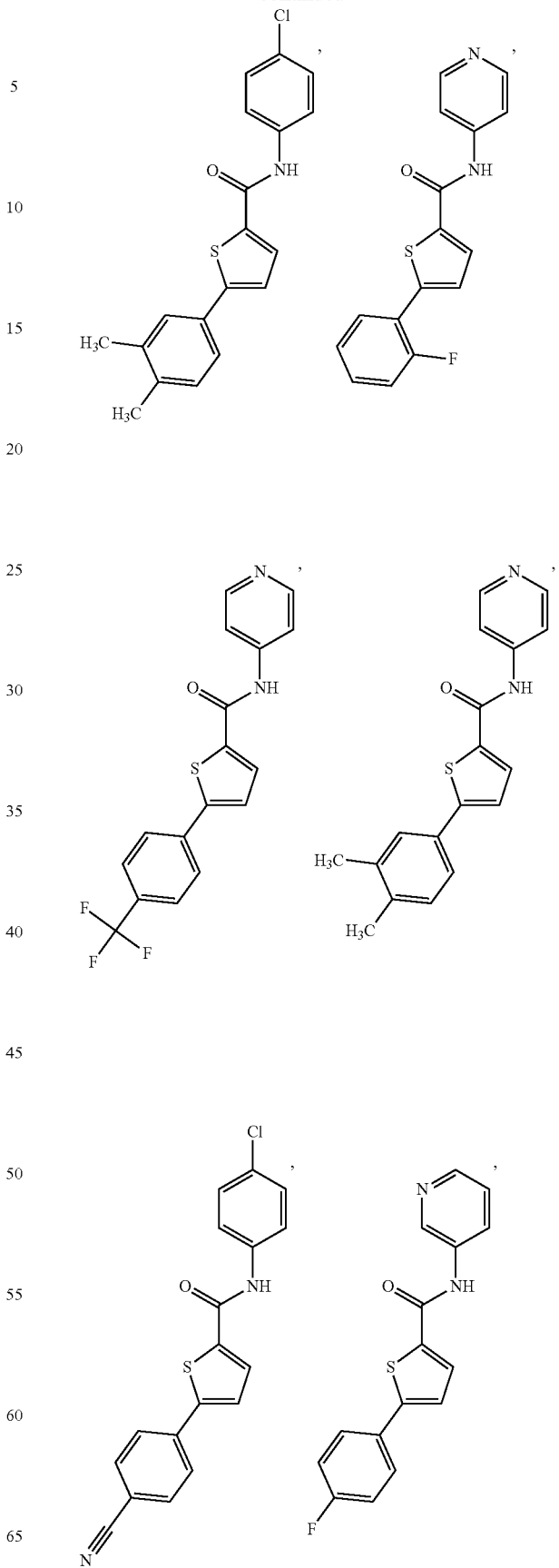

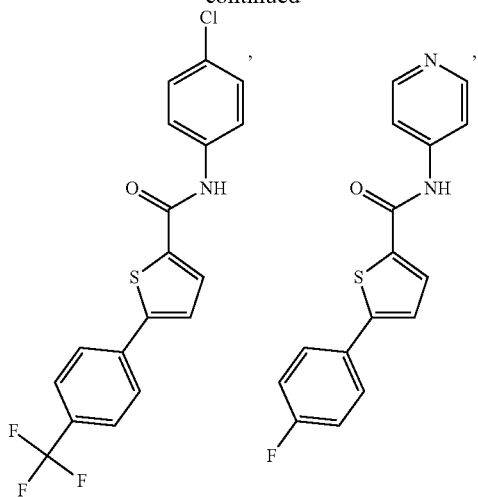
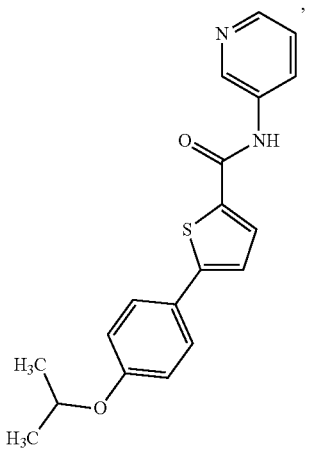
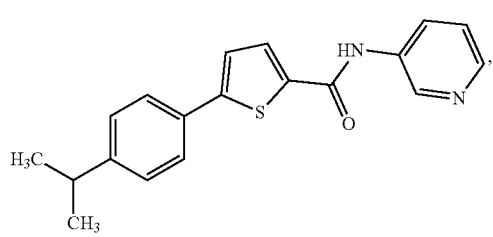
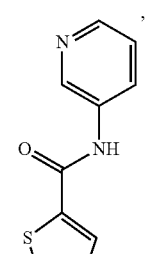
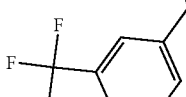
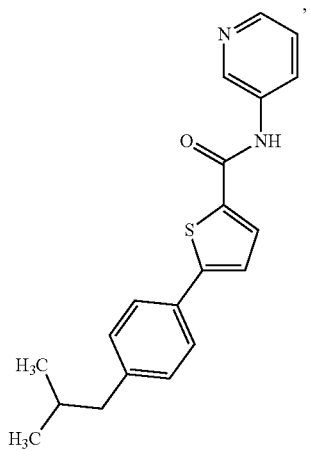
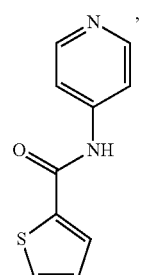
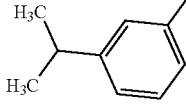
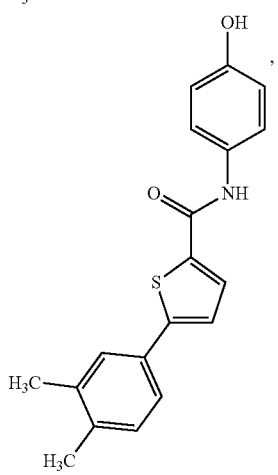
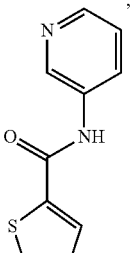
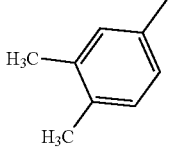

123
-continued
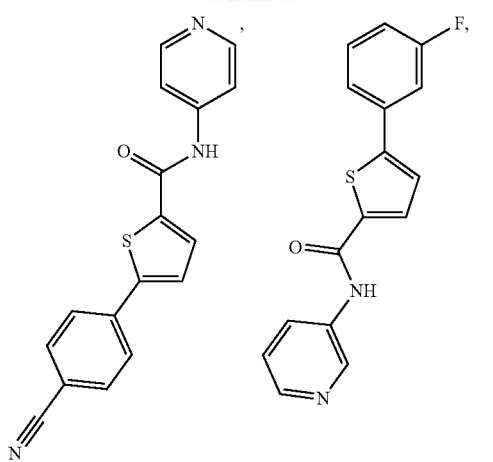
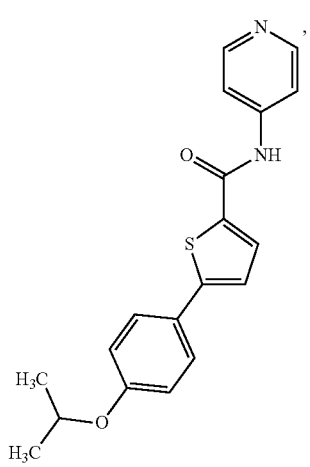
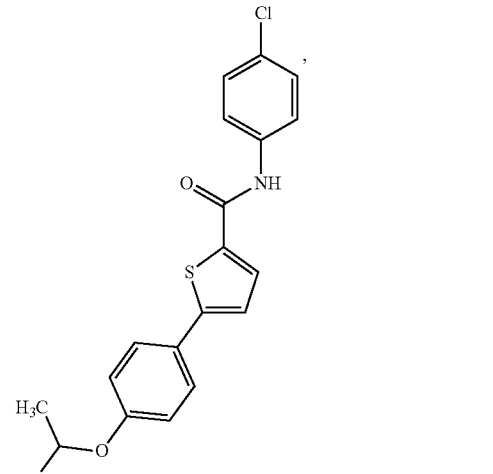
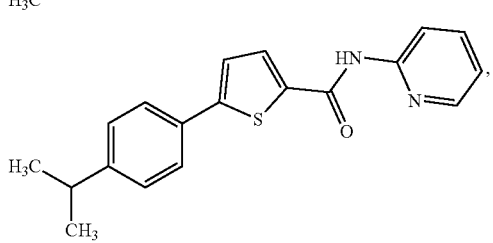
124
-continued
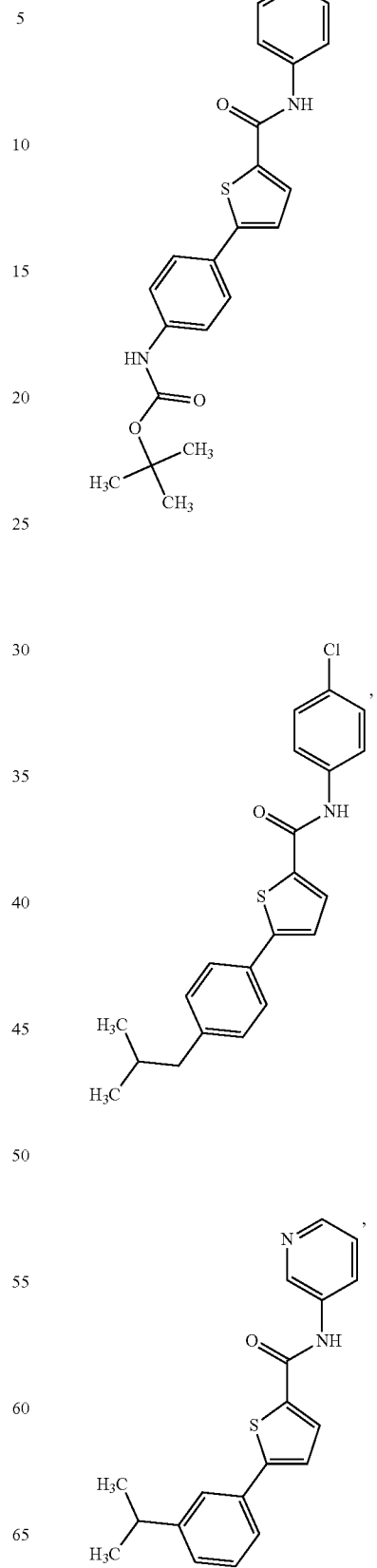

125
-continued
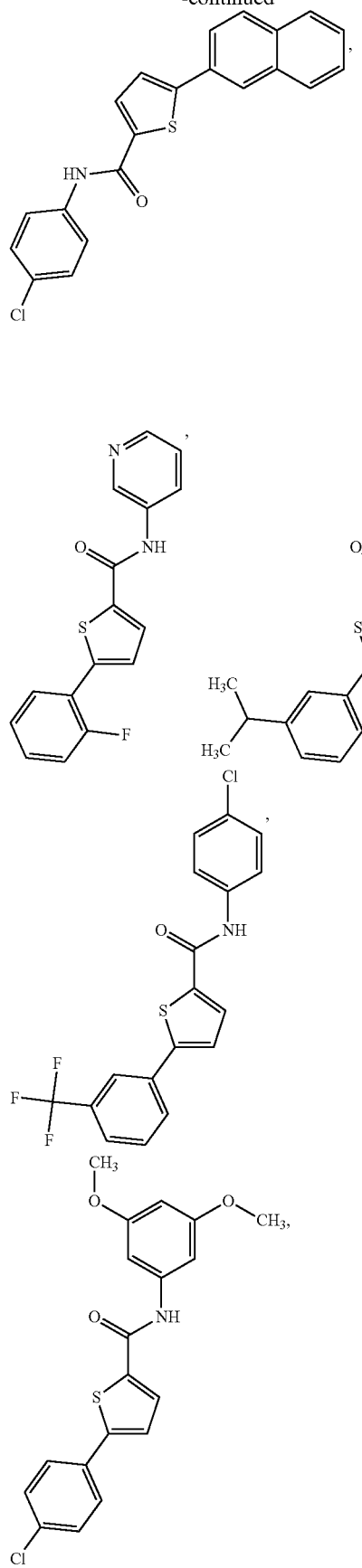
126
-continued
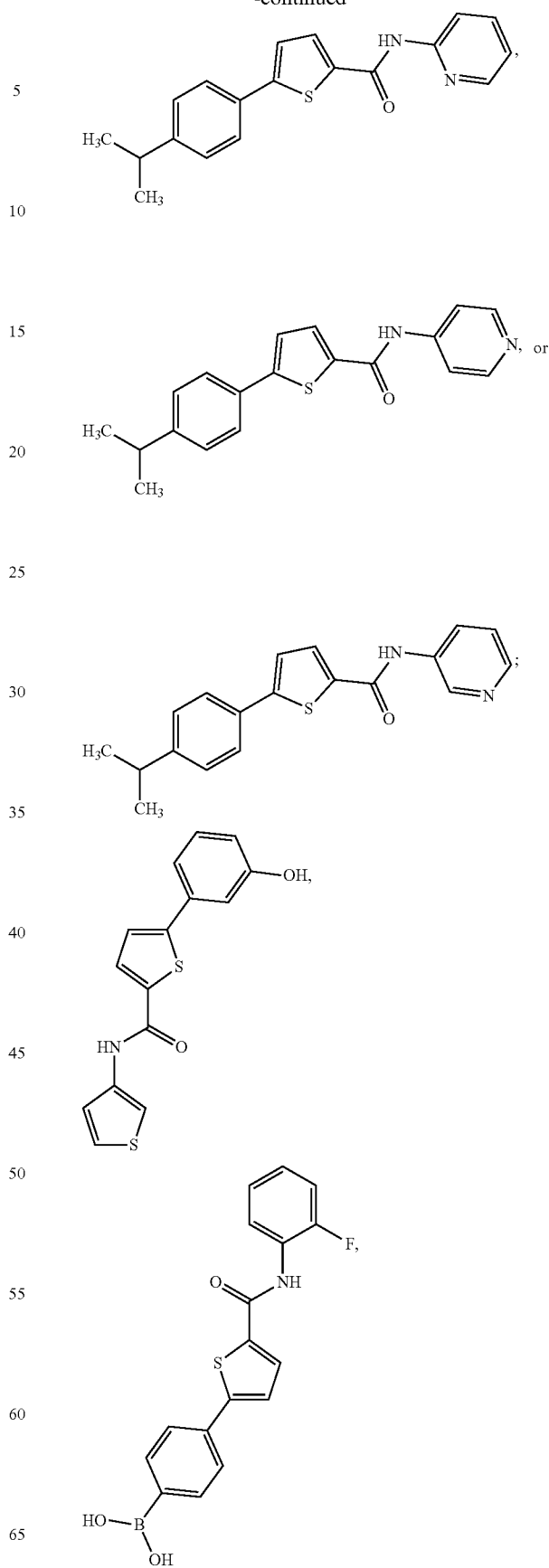

127
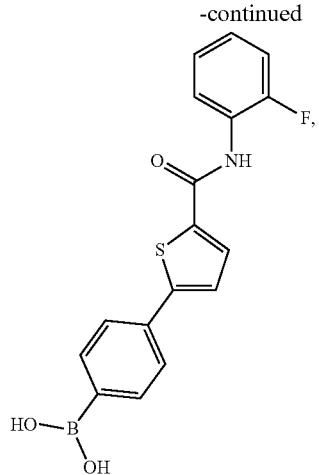
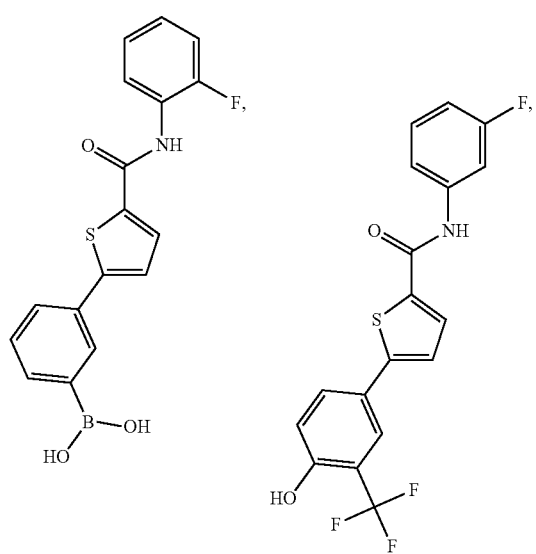
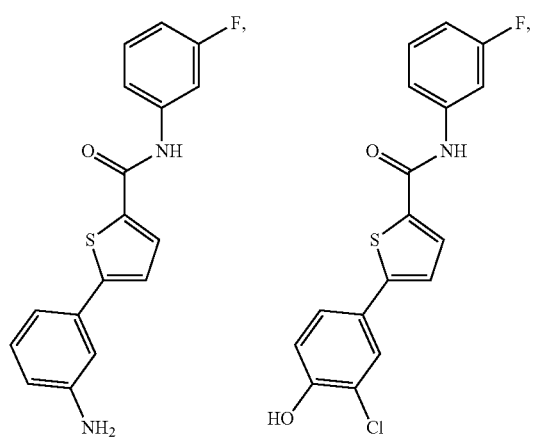
128
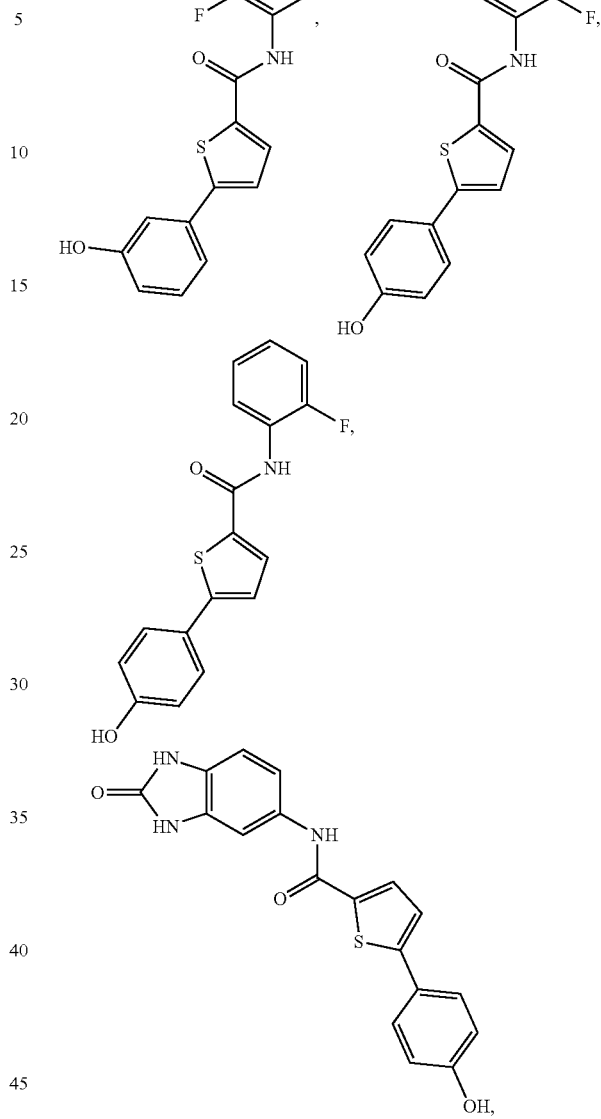
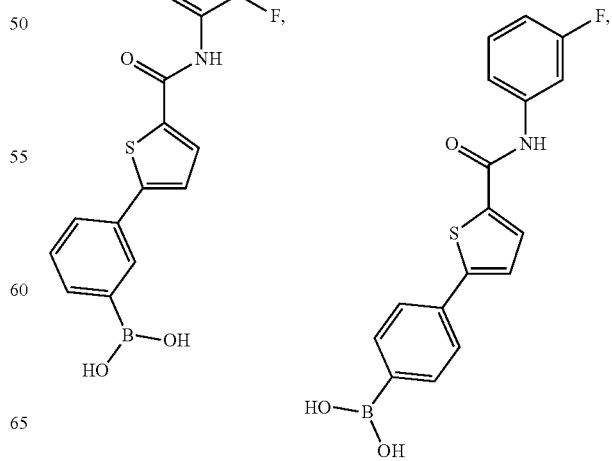

129
-continued
130
-continued
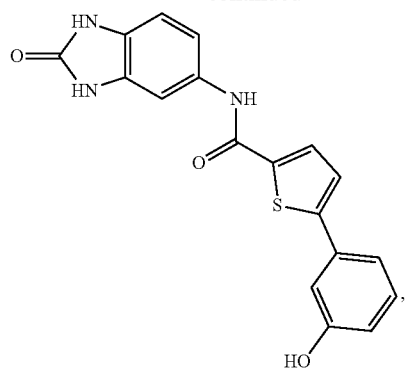
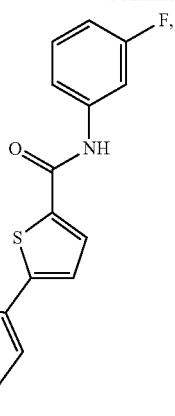
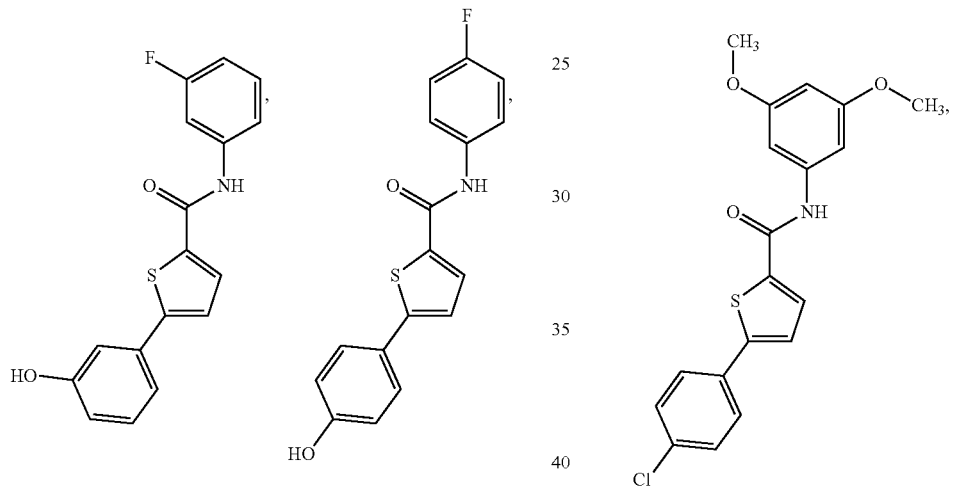
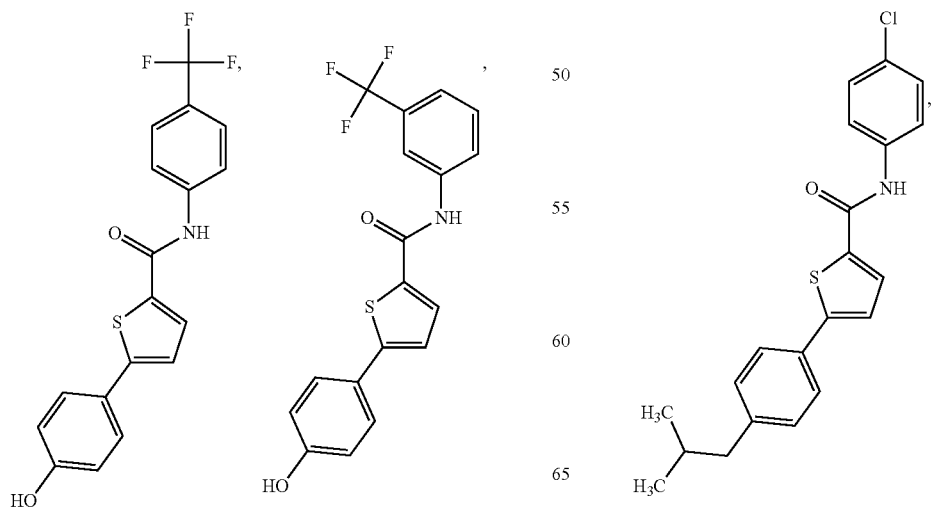

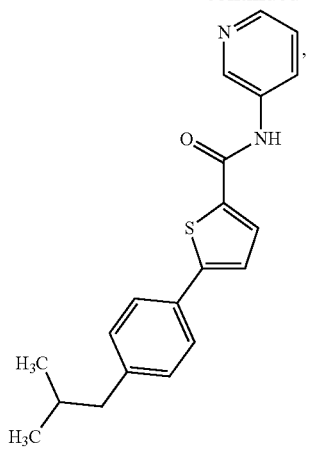
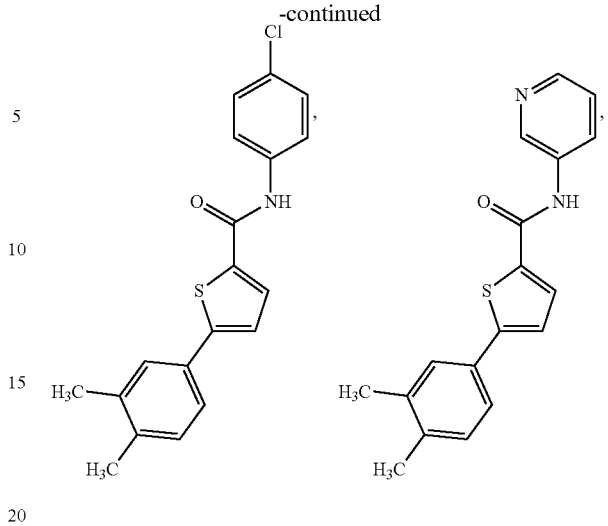
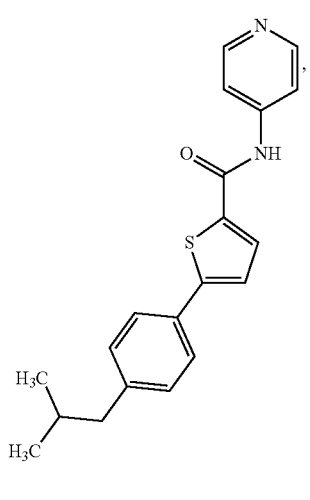
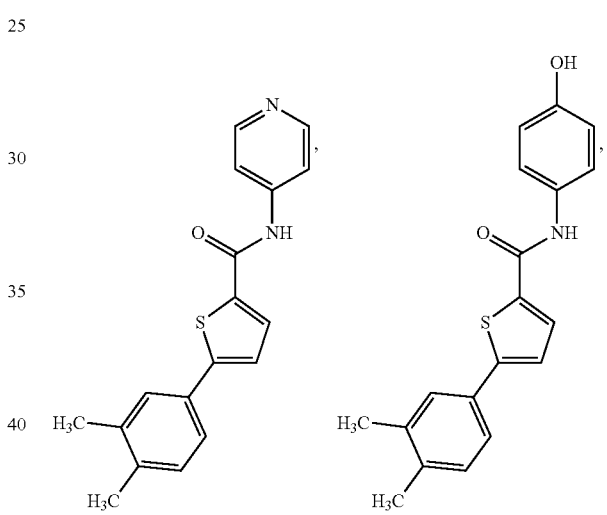
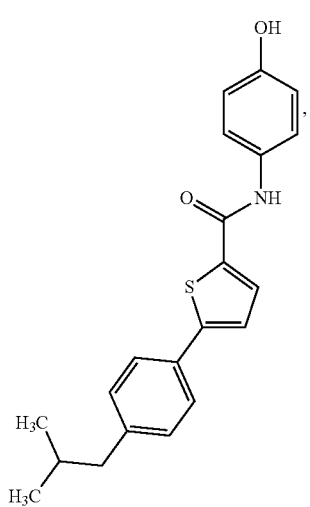
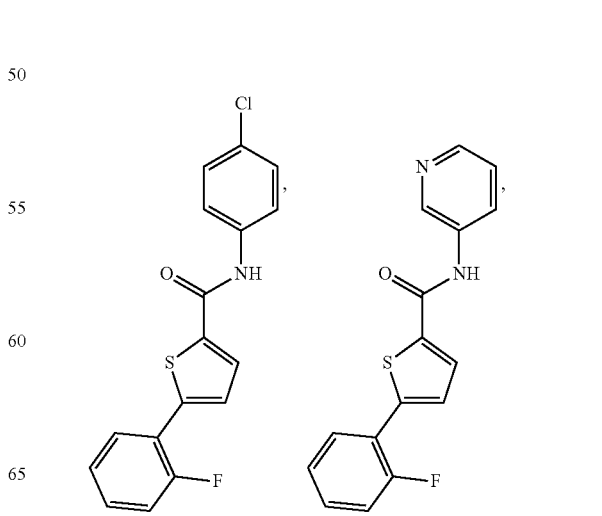

133
-continued
134
-continued
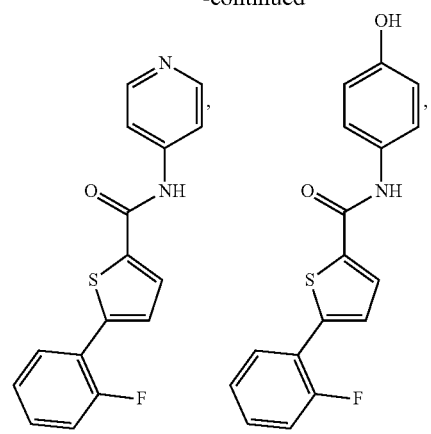
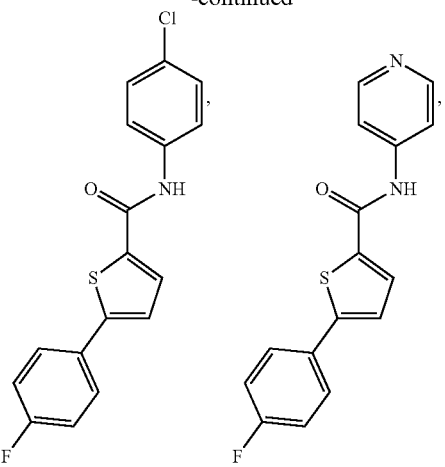

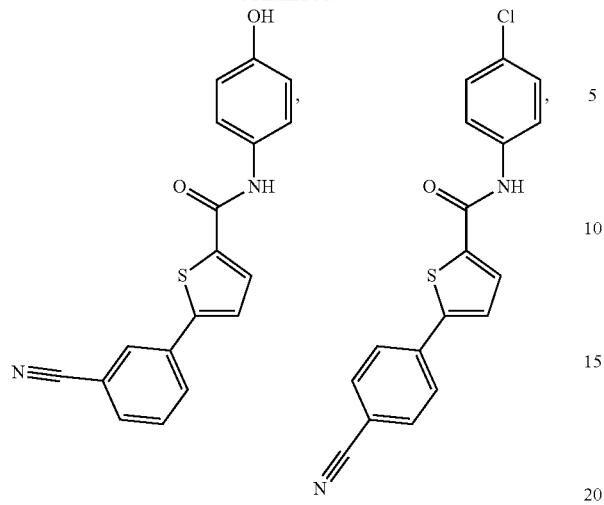
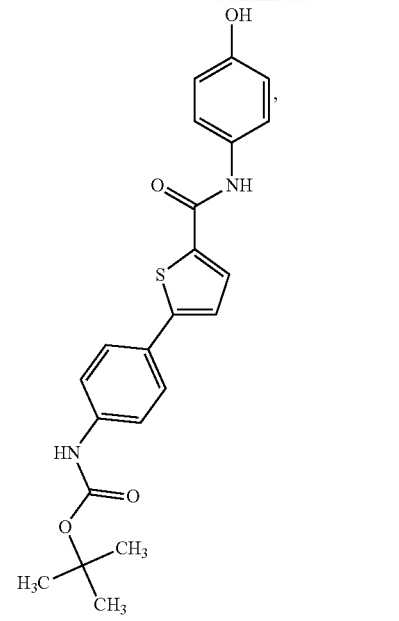
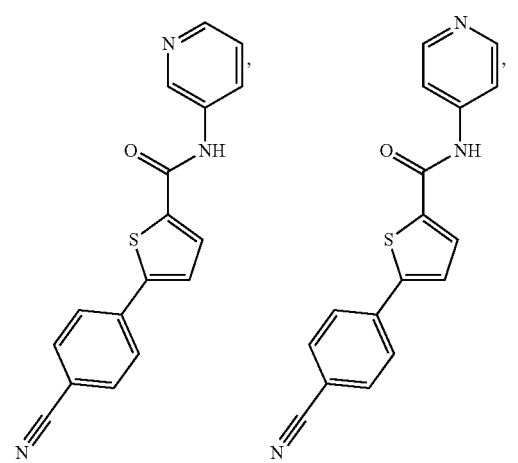
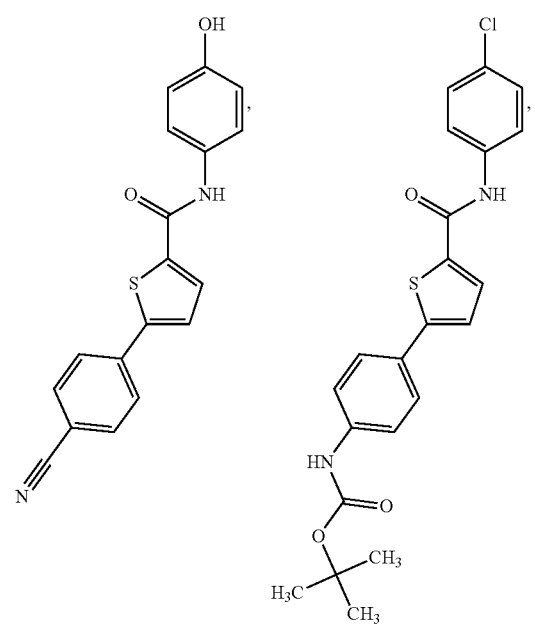
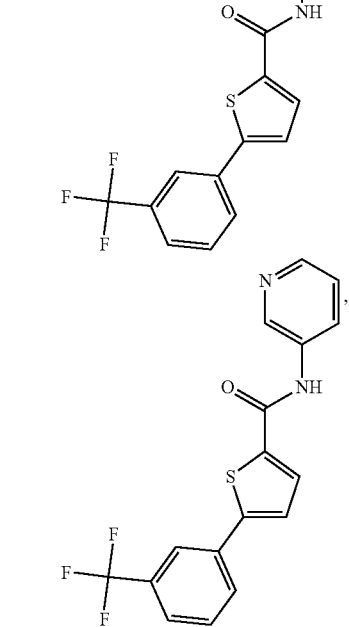

-continued
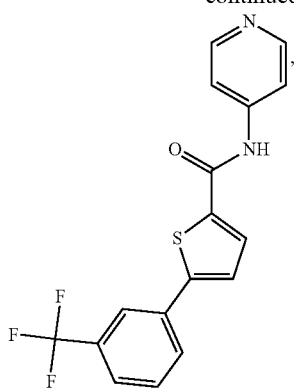
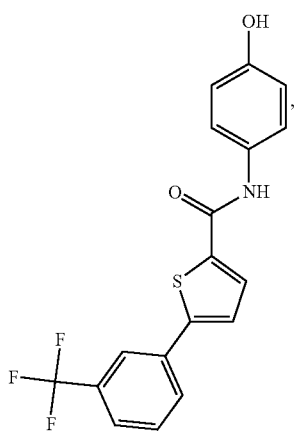
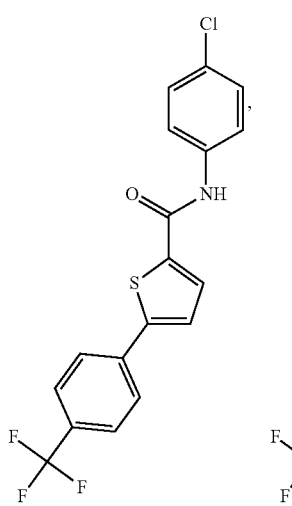
-continued
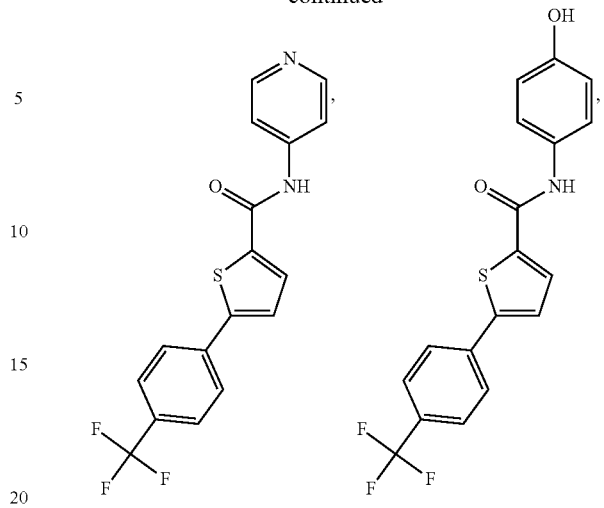
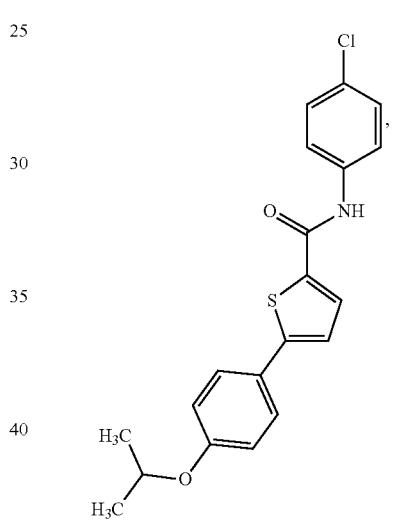
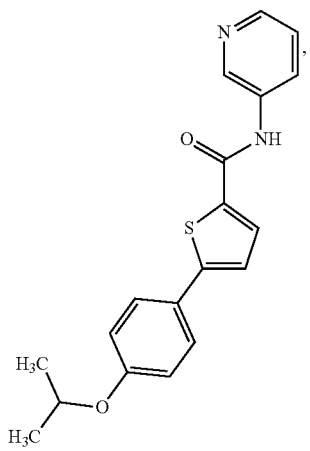

139                                           140
-continued                                    -continued
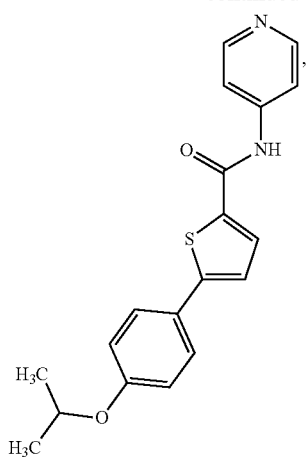
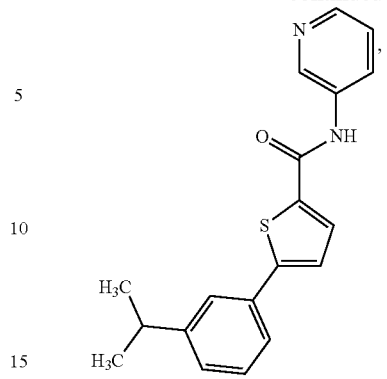
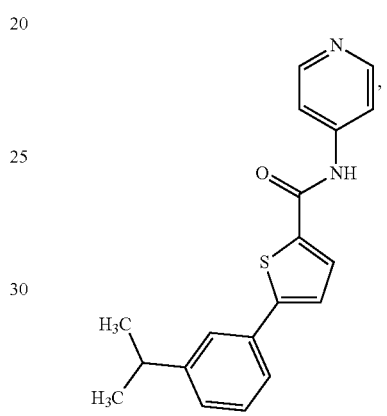
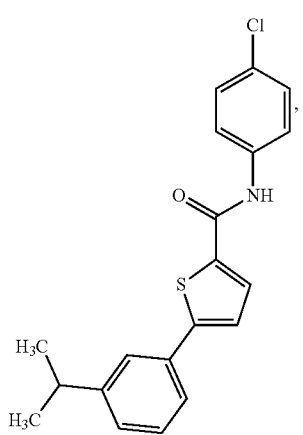
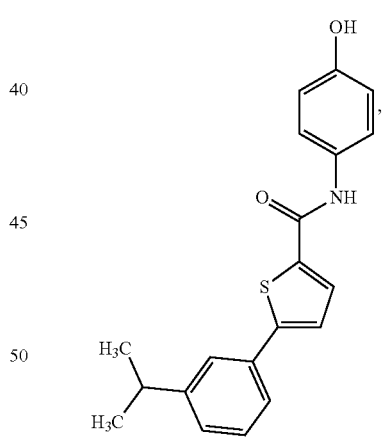
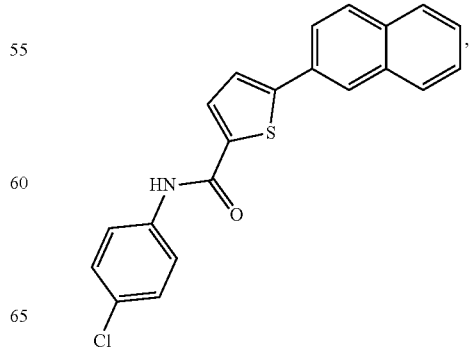

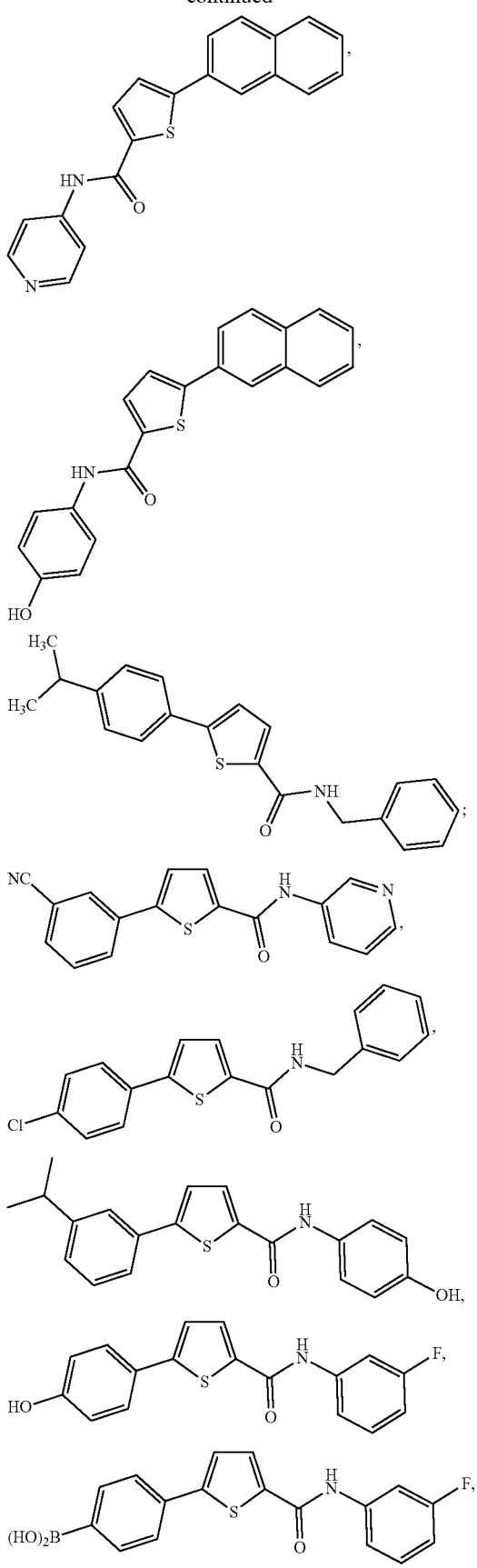
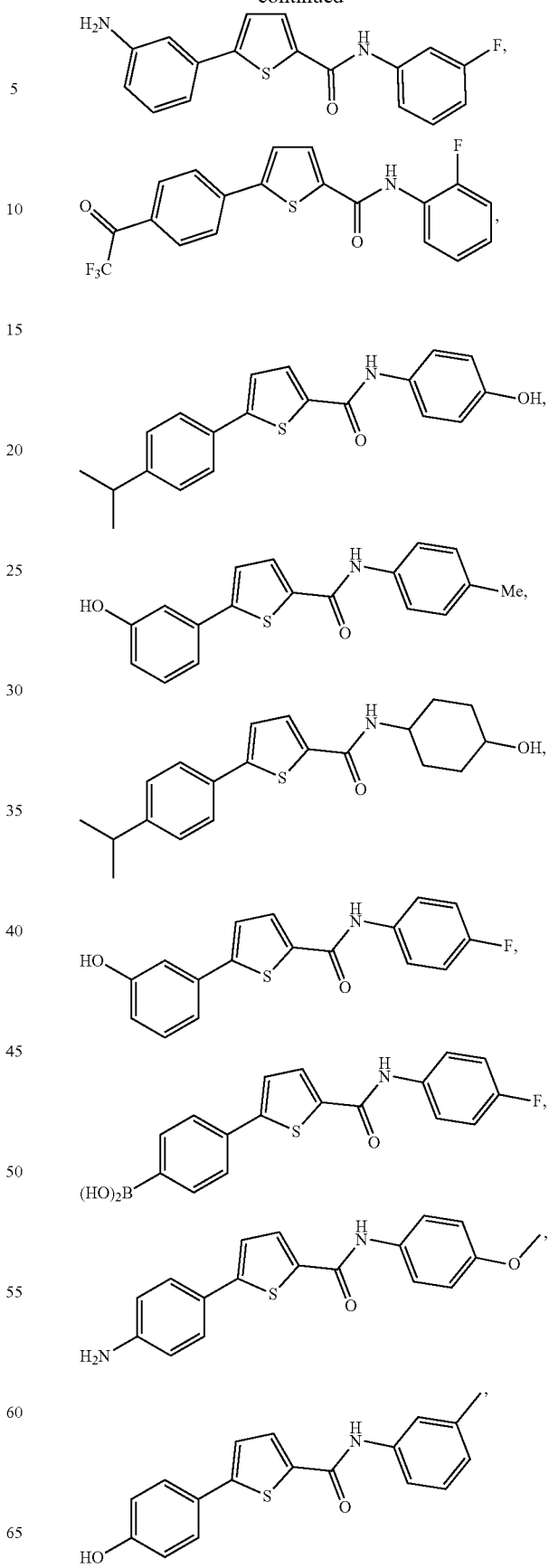

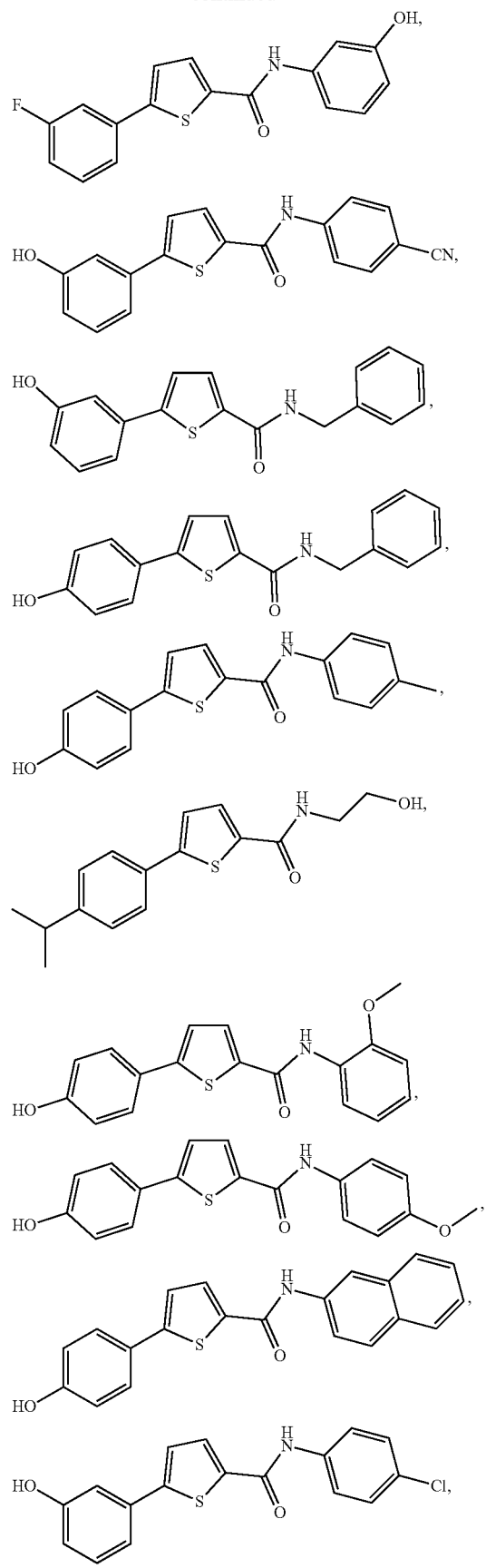
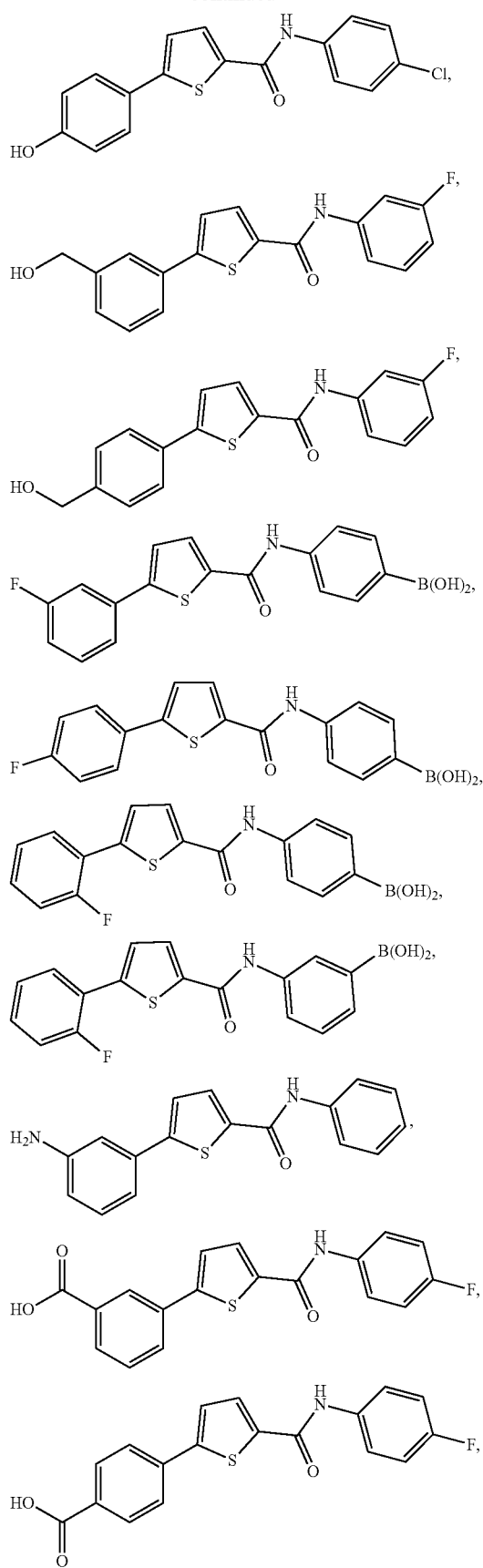

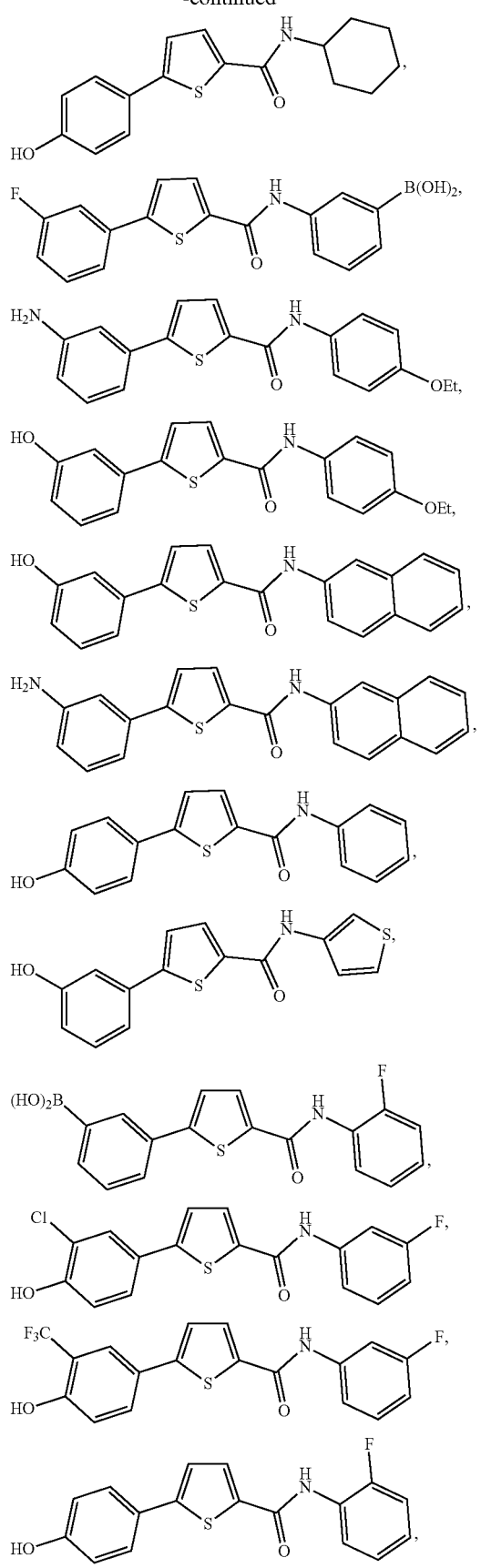
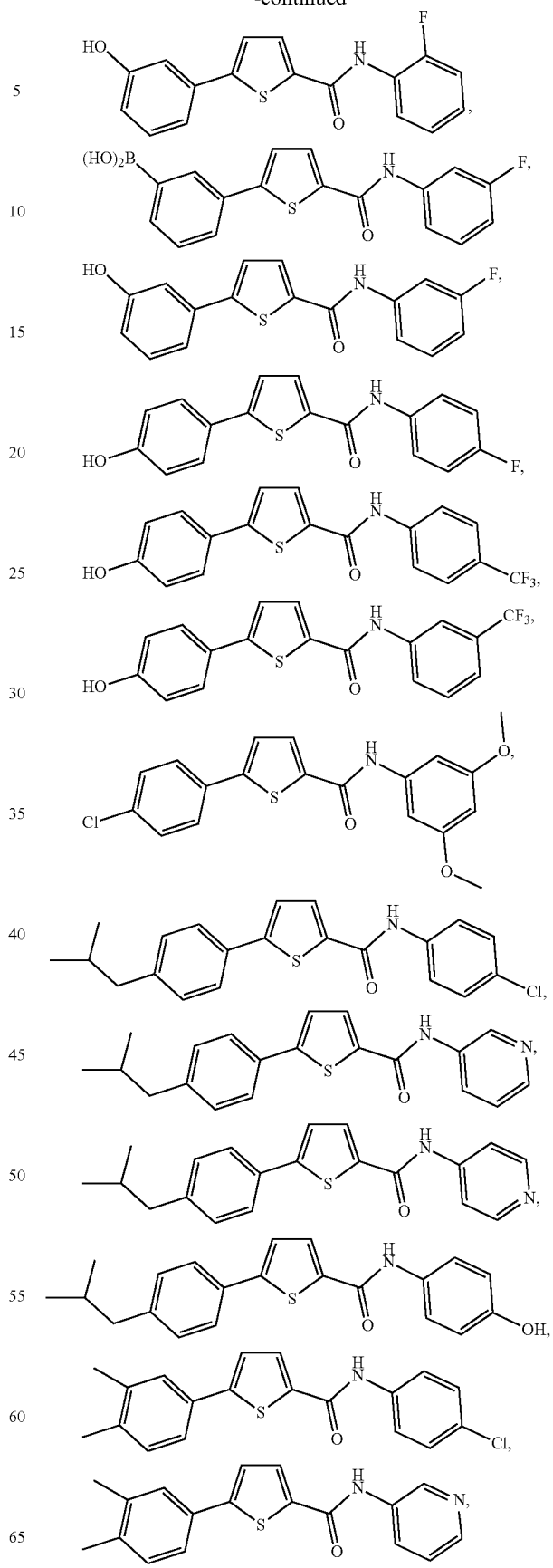

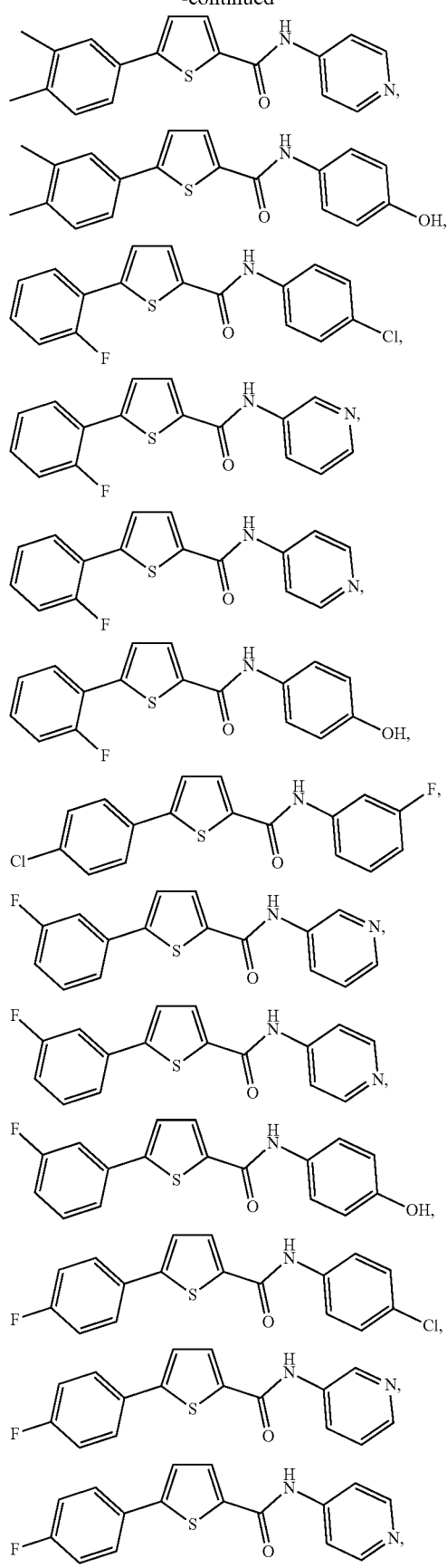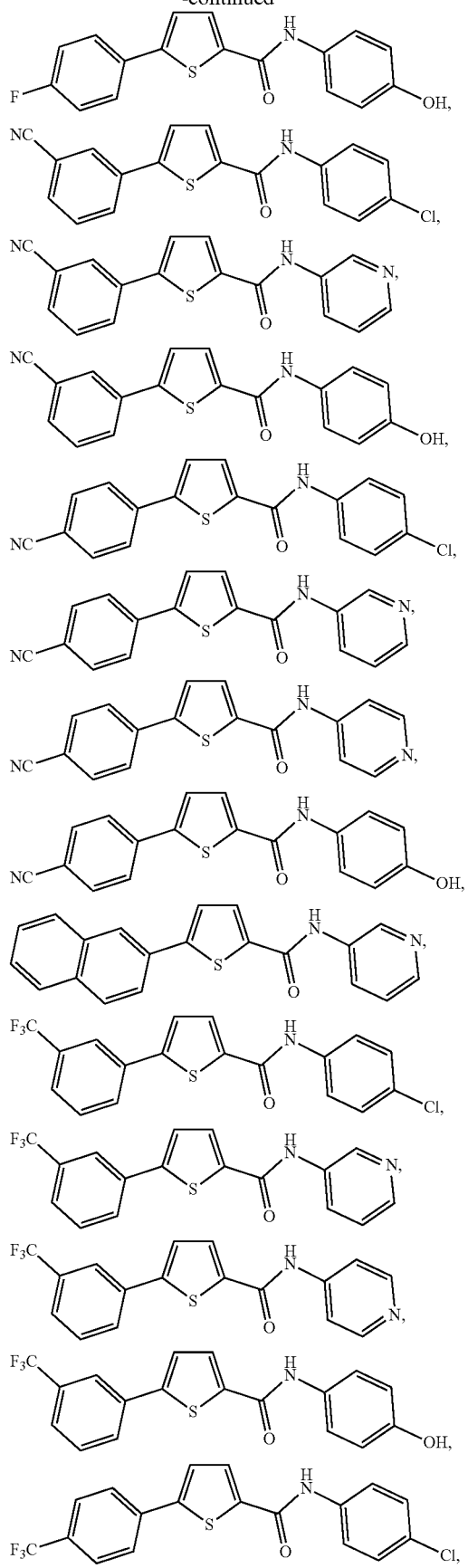

149
-continued

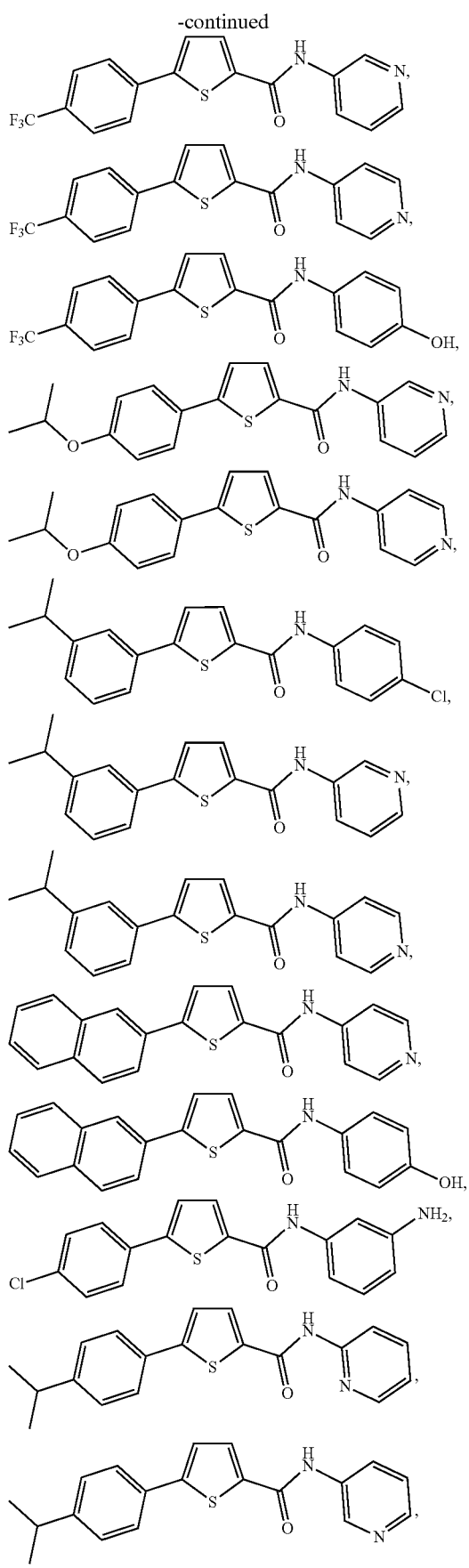

150
-continued

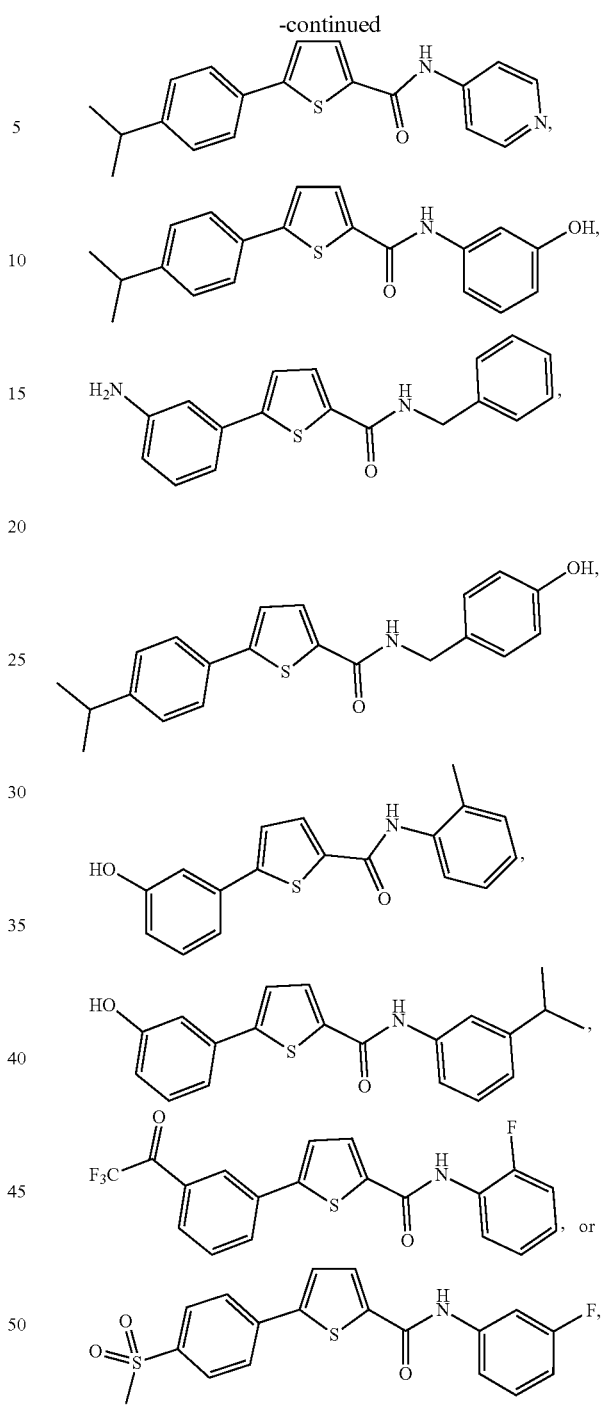

15. A pharmaceutical composition comprising:
 (A) a compound of claim 1; and
 (B) an excipient.

16. A method of treating obesity, diabetes, non-alcoholic fatty liver disease, muscular dystrophy, or a neurological disease or disorder, wherein the neurological disorder is selected from dementia, Alzheimer's disease, amyotrophic lateral sclerosis, or Parkinson's Disease in a patient comprising administering to the patient in need thereof a therapeutically effective amount of a compound or composition of claim 1.

17. The method of claim 16, wherein the disease or disorder is obesity, diabetes, or non-alcoholic fatty liver disease.

18. The method of claim 16, wherein the disease or disorder is a muscular dystrophy or a neurological disease or disorder, wherein the neurological disorder is selected from dementia, Alzheimer's disease, amyotrophic lateral sclerosis, or Parkinson's disease.

* * * * *

UNITED STATES PATENT AND TRADEMARK OFFICE
CERTIFICATE OF CORRECTION

PATENT NO. : 11,795,162 B2  
APPLICATION NO. : 16/639807  
DATED : October 24, 2023  
INVENTOR(S) : Thomas Burris et al.

Page 1 of 1

It is certified that error appears in the above-identified patent and that said Letters Patent is hereby corrected as shown below:

In the Claims

Column 133, Lines 25-40, Claim 14, delete:

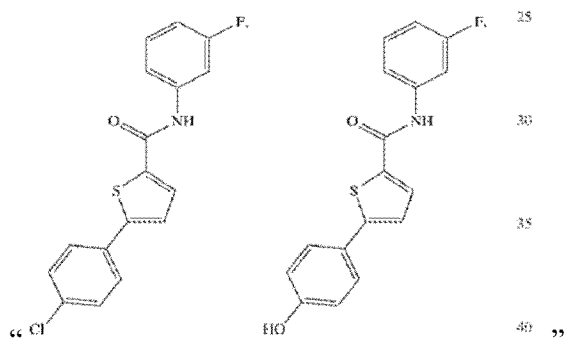

And insert therefore:

Column 150, Line 54, at the end of the Claim 14, insert --or a pharmaceutically acceptable salt thereof.--.

Signed and Sealed this  
Twenty-sixth Day of December, 2023

*Katherine Kelly Vidal*

Katherine Kelly Vidal  
*Director of the United States Patent and Trademark Office*